(12) United States Patent
Watabe et al.

(10) Patent No.: US 8,253,578 B2
(45) Date of Patent: Aug. 28, 2012

(54) SMOKE SENSOR OF THE SOUND WAVE TYPE INCLUDING A SMOKE DENSITY ESTIMATION UNIT

(75) Inventors: Yoshifumi Watabe, Tondabayashi (JP); Yoshiaki Honda, Seika-cho (JP); Tomizo Terasawa, Suita (JP); Yuji Takada, Kyoto (JP); Takayuki Nishikawa, Osaka (JP)

(73) Assignee: Panasonic Corporation, Osaka (JP)

( * ) Notice: Subject to any disclaimer, the term of this patent is extended or adjusted under 35 U.S.C. 154(b) by 680 days.

(21) Appl. No.: 12/300,332

(22) PCT Filed: May 1, 2007

(86) PCT No.: PCT/JP2007/059313
§ 371 (c)(1),
(2), (4) Date: Nov. 10, 2008

(87) PCT Pub. No.: WO2007/132671
PCT Pub. Date: Nov. 22, 2007

(65) Prior Publication Data
US 2009/0184830 A1 Jul. 23, 2009

(30) Foreign Application Priority Data

| | | |
|---|---|---|
| May 12, 2006 | (JP) | 2006-134289 |
| Mar. 16, 2007 | (JP) | 2007-069087 |
| Mar. 16, 2007 | (JP) | 2007-069088 |
| Mar. 16, 2007 | (JP) | 2007-069089 |
| Mar. 16, 2007 | (JP) | 2007-069090 |
| Mar. 16, 2007 | (JP) | 2007-069091 |
| Mar. 16, 2007 | (JP) | 2007-069092 |

(51) Int. Cl.
*G08B 21/00* (2006.01)
(52) U.S. Cl. .................................. 340/628; 73/865.5

(58) Field of Classification Search .......... 340/628–630; 73/865.5, 28.01, 61.75
See application file for complete search history.

(56) References Cited

U.S. PATENT DOCUMENTS 3,802,271 A 4/1974 Bertelson
(Continued)

FOREIGN PATENT DOCUMENTS

CN 1698400 A 11/2005
(Continued)

OTHER PUBLICATIONS

The First Office Action for the Application No. 200780017260.8 from State Intellectual Property Office of People's Republic of China dated Mar. 26, 2010.

(Continued)

*Primary Examiner* — Jeffery Hofsass
(74) *Attorney, Agent, or Firm* — Cheng Law Group, PLLC

(57) ABSTRACT

The present invention provides a smoke sensor of sound wave type that excels in responsiveness and has a low probability of false detection. The smoke sensor has a sound wave generating unit that provides an ultrasound wave to a monitoring space, a sound wave receiving unit that receives the ultrasound wave from the sound wave generating unit via the monitoring space, and a signal processing unit that detects an abnormality of the monitoring space by using an output of the sound wave receiving unit. The signal processing unit includes a smoke density estimation unit that estimates a smoke density in the monitoring space on the basis of a difference between the output of the sound wave receiving unit and a standard value, and a smoke density determination unit that determines the abnormality of the monitoring space by comparing the smoke density estimated by the smoke density estimation unit with a predetermined threshold.

33 Claims, 25 Drawing Sheets

U.S. PATENT DOCUMENTS

| | | | |
|---|---|---|---|
| 4,701,625 A | 10/1987 | Kimura | |
| 4,706,509 A | 11/1987 | Riebel | |
| 2005/0035685 A1 | 2/2005 | Tanaka et al. | |
| 2005/0201575 A1 | 9/2005 | Koshida et al. | |
| 2005/0262927 A1 | 12/2005 | Scott | |

FOREIGN PATENT DOCUMENTS

| | | | |
|---|---|---|---|
| JP | 49-064398 A | 6/1974 | |
| JP | 58-135956 A | 8/1983 | |
| JP | 61-033595 A | 2/1986 | |
| JP | 61-180390 U | 11/1986 | |
| JP | 62-052699 A | 3/1987 | |
| JP | 63-255800 A | 10/1988 | |
| JP | 9-243445 A | 9/1997 | |
| JP | 10-56679 A | 2/1998 | |
| JP | 2001-034862 A | 2/2001 | |
| JP | 2004-163262 A | 6/2004 | |
| JP | 2005-20315 A | 1/2005 | |
| JP | 2005-258747 A | 9/2005 | |
| JP | 2005-269745 A | 9/2005 | |
| TW | 35337 | 2/1981 | |
| TW | 497135 | 8/2002 | |
| TW | 200508998 | 3/2005 | |

OTHER PUBLICATIONS

Supplementary European Search Report for the Application No. EP 07 74 2748 dated Apr. 15, 2011.

Notification of Reasons for Refusal for the Application No. JP 2008-515484 from Japan Patent Office mailed Dec. 7, 2010.

Taiwanese Office Action for the Application No. 096116448 from Taiwan Patent Office mailed Feb. 22, 2010.

International Search Report for the Application No. PCT/JP2007/059313 mailed Jul. 31,2007.

European Office Action for the Application No. 07 742 748.2 dated Jan. 27, 2012.

Fig. 3
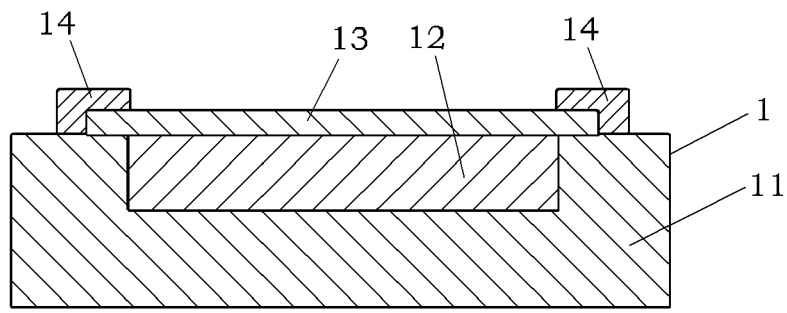
Fig. 4
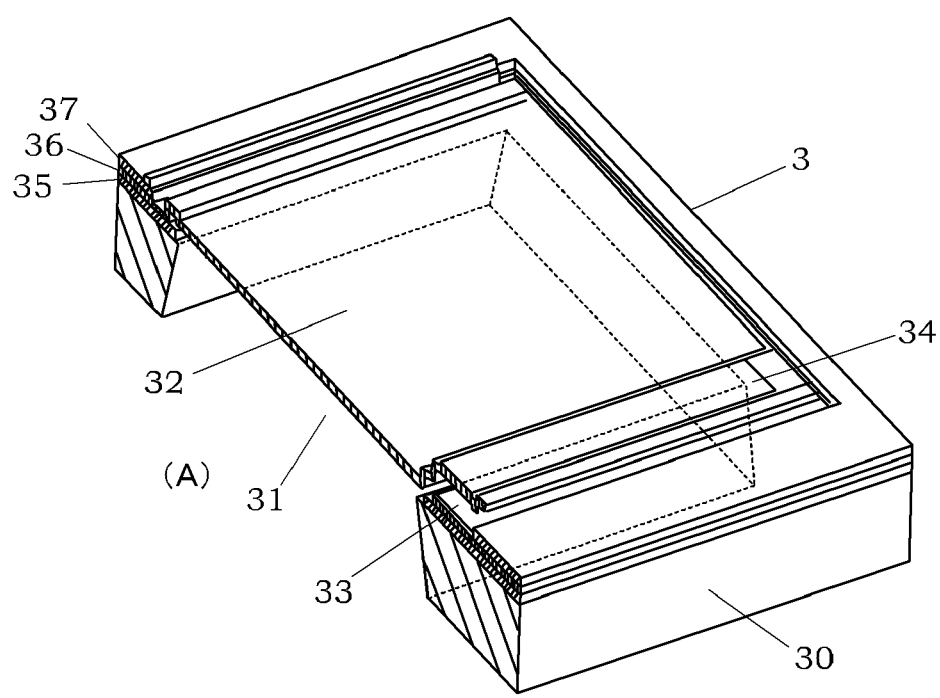
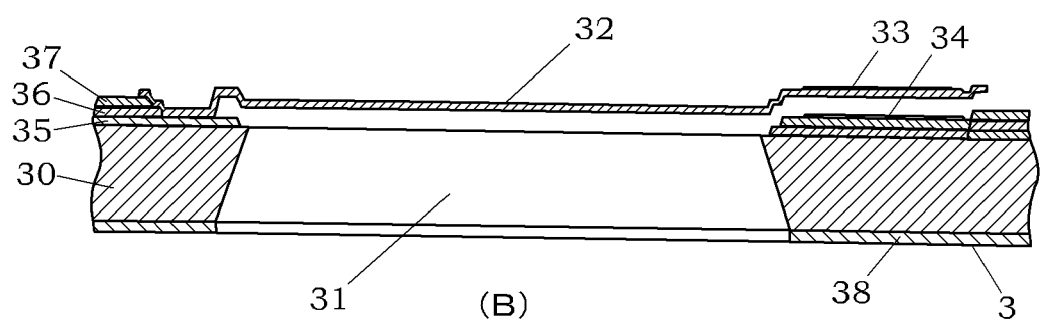

Fig.8

S11
> Ultrasound wave generating unit is successively driven
> at each frequency (for example, 20 kHz, 82 kHz)
> and output of wave receiving element is measured S12
> Attenuation at each frequency is calculated
> from the measured output at each frequency
> and standard output stored in storage unit S13
> Attenuation at standard frequency (Here, 82 kHz)
> is taken as 1 and ratio with attenuation
> at another frequency (here 20kHz) is calculated S14
> Calculated attenuation ratio is compared with attenuation ratio
> of each smoke particle stored in storage unit
> and type of smoke particle is estimated S15
> Smoke density is estimated with smoke density estimation unit
> when smoke particle is a smoke particle that has been determined
> in advance as monitoring object S16
> Smoke density is calculated from unit attenuation ratio
> corresponding to the type of smoke particle estimated
> at specific frequency (here 82kHz) stored in storage unit S17
> Result is compared with stored predetermined threshold (here, 10%/M)
> and when the threshold is exceeded,
> it is determined that fire has occurred

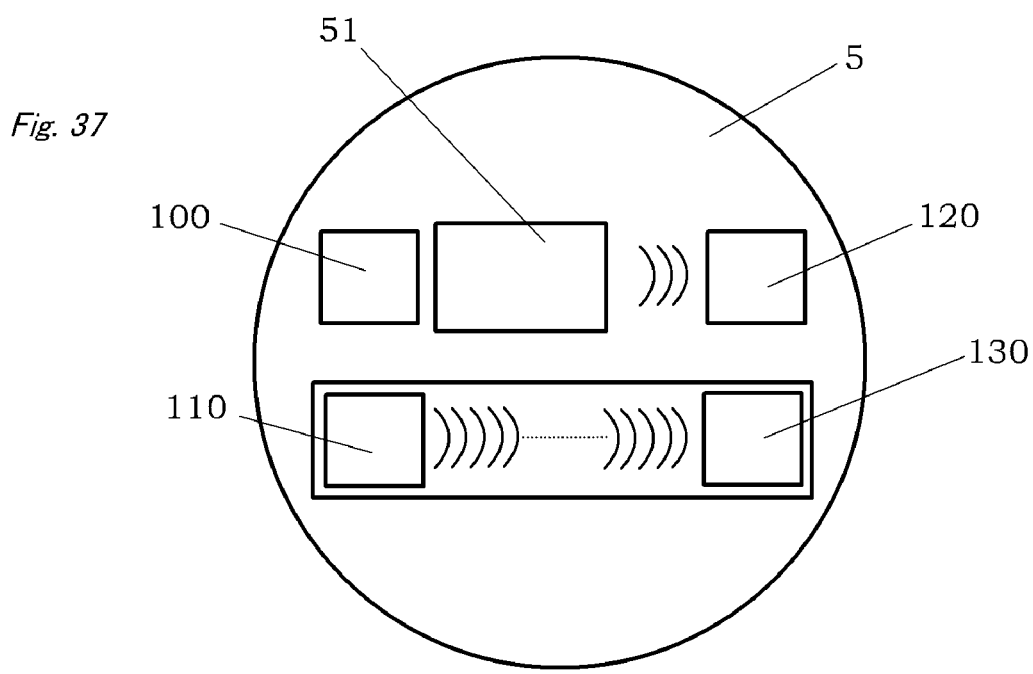
Fig. 37
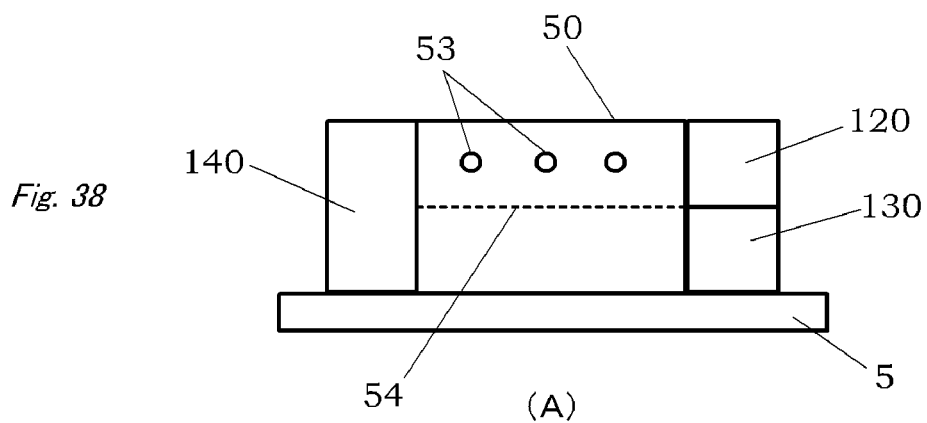
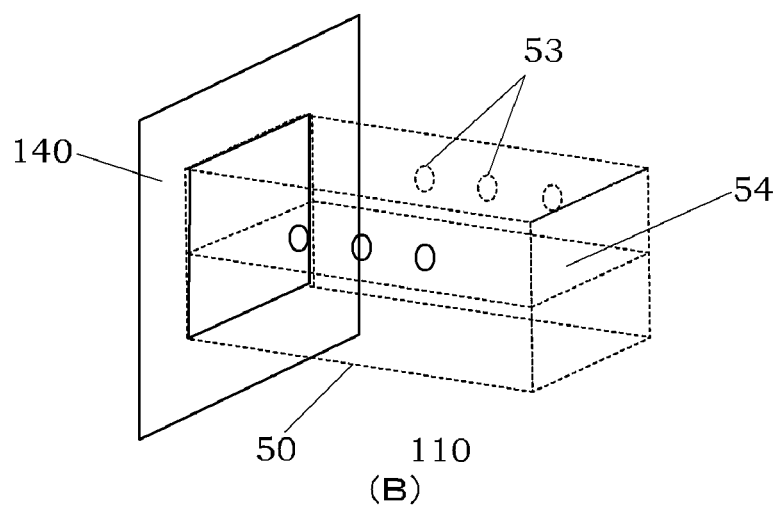
Fig. 38

Fig. 45
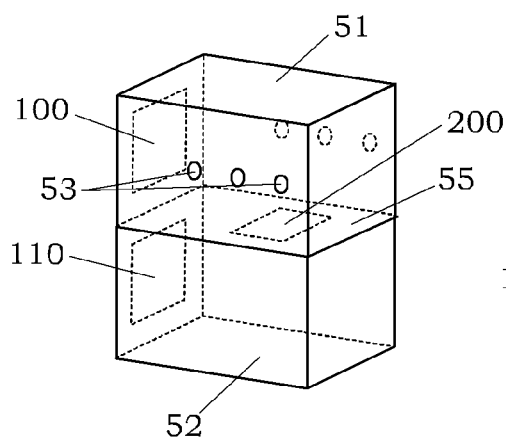
Fig. 46
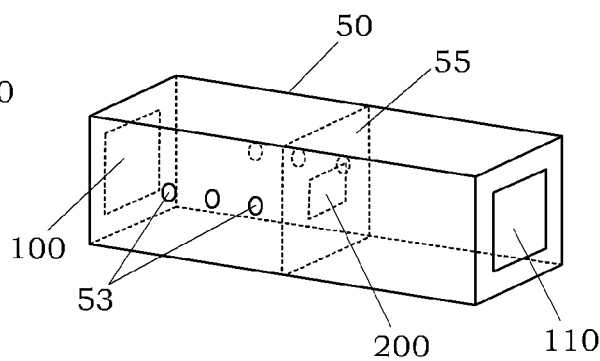
Fig. 47
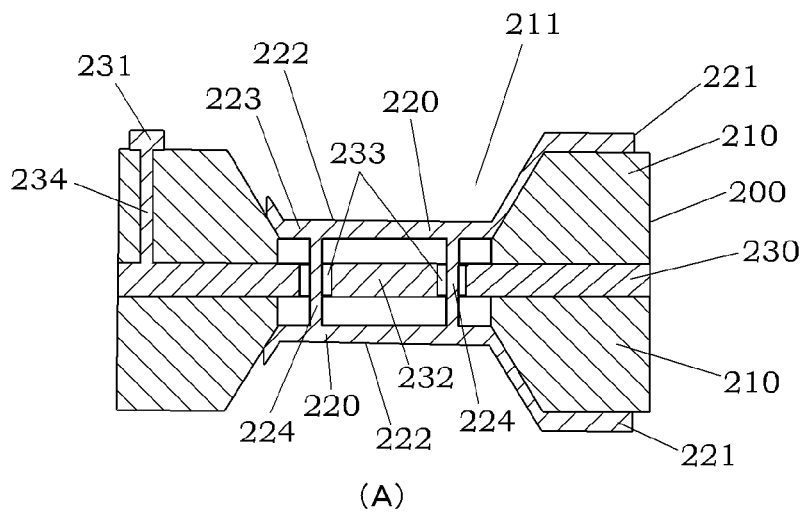
(A)
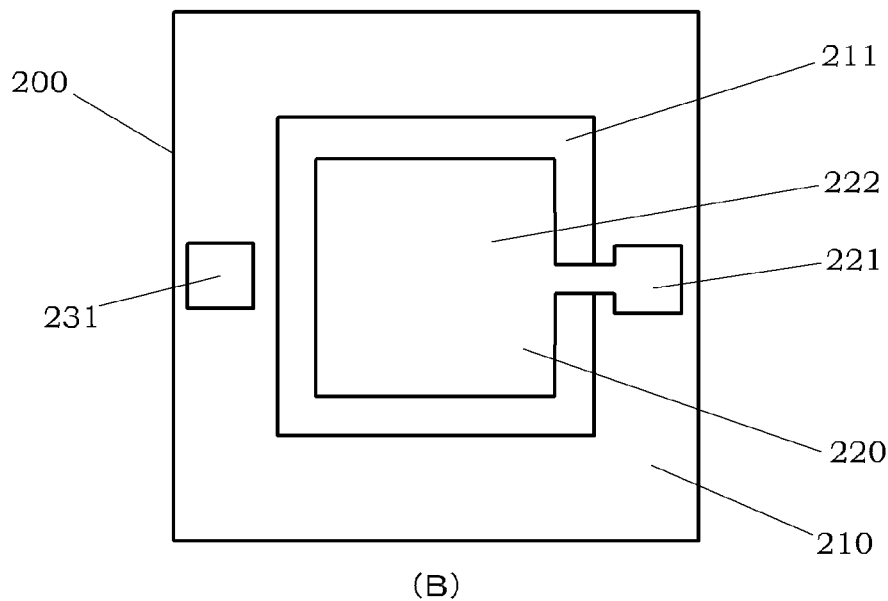
(B)

(A)

(B)

(A)

(B)

SMOKE SENSOR OF THE SOUND WAVE TYPE INCLUDING A SMOKE DENSITY ESTIMATION UNIT

TECHNICAL FIELD

The present invention relates to a smoke sensor using sound waves or ultrasound waves.

BACKGROUND

Smoke sensors have been widely used as fire sensors that detect smoke generated during fire or the like and produce fire alarm. A smoke sensor of a light scattering type is described in Japanese Patent Application Laid Open No. 2001-34862 and a smoke sensor of a light dimming type is described in Japanese Patent Application No. 61-33595.

The smoke sensor of a light scattering type is so configured that scattered light produced when light irradiated by a projection element composed of a light-emitting diode element into a monitoring space is scattered on smoke particles is received by a light receiving element composed of a photodiode. Where smoke particles are present in the monitoring space, the produced scattered light increases the amount of light received by the light receiving element. Therefore, the presence of smoke particles can be detected based on the increase in the amount of light received by the light receiving element. However, because a labyrinth body has to be provided as a measure against stray light, when the flow of air is small, a long time is required for the smoke particles to penetrate into the monitoring space when fire occurs and problems are associated with responsiveness of the sensor.

The smoke sensor of a light dimming type is configured so that light irradiated from a projection element is directly received by a light receiving element, and where smoke particles are present in a monitoring space between the projection element and light receiving element, the amount of light received by the light receiving element decreases and the presence of smoke particle can be detected based on the decrease in the amount of light received by the light receiving element. However, in such sensor, a false alarm (false detection) can be generated under the effect of background light even when no fire has occurred. Furthermore, when a smoke sensor of a light dimming type has a detachable configuration, optical axes of the projection element and light receiving element have to be aligned with high accuracy and problems are associated with time and efforts required for installation.

Furthermore, in the smoke sensors of light scattering type and light dimming type, an alarm can be falsely generated when steam, rather than smoke, penetrates into the monitoring space. Therefore such sensors are not suitable for use in kitchens and bathrooms. Thus, there is also space for improvement in this area.

DISCLOSURE OF THE INVENTION

Accordingly, in view of the above-described problems, it is an object of the present invention to provide a highly reliably smoke sensor that excels in responsiveness and has a reduced probability of false detection.

Thus, the smoke sensor in accordance with the present invention includes a sound wave generating unit that provides a sound wave to a monitoring space; a control unit that controls the sound wave generating unit; a sound wave receiving unit that receives the sound wave from the sound wave generating unit via the monitoring space; and a signal processing unit that detects an abnormality of the monitoring space by using an output of the sound wave receiving unit, wherein the signal processing unit includes a smoke density estimation unit that estimates a smoke density in the monitoring space on the basis of a difference between the output of the sound wave receiving unit and a standard value, and a smoke density determination unit that determines the abnormality on the basis of a result obtained by comparing the smoke density found by the smoke density estimation unit with a predetermined threshold.

With the smoke sensor in accordance with the present invention, the effect of background light that creates a problem in the smoke sensor of a light dimming type is avoided, smoke detection sensitivity is increased, a labyrinth body that is required in the smoke sensor of a light scattering type becomes unnecessary, the diffusion of smoke particles into the monitoring space is facilitated, and responsiveness is improved.

The sound wave generated by the sound wave generating unit is not particularly limited, provided that the above-described effect of smoke sensor can be attained, but a sound wave with a frequency, for example, equal to or higher than 1 kHz is preferred. Further, for the reasons described hereinabove, it is even more preferred that ultrasound waves with a frequency equal to or higher than 20 kHz be used. Thus, when ultrasound waves are used, the attenuation amount of ultrasound waves passing through the monitoring space that is caused by increased smoke density therein is high. Therefore, smoke detection sensitivity increases. Furthermore, such sound waves are not heard by people around the smoke sensor when smoke is detected, the waves have high straight propagation ability, and disturbance ultrasound waves can be easily shielded.

In the smoke sensor of the preferred embodiment of the present invention, the sound wave generating unit has a function of providing a plurality of sound waves that have different frequencies; the signal processing unit has a storage unit that stores data representing a relationship between the output of the sound wave receiving unit and a frequency of the sound wave provided by the sound wave generating unit that has been examined in advance under a plurality of test conditions that differ in a type of smoke present in the monitoring space and a smoke density, and a smoke particle determination unit that determines the type of smoke particles present in the monitoring space by using the data of the storage unit and the output of the sound wave receiving unit obtained by providing each of the plurality of sound waves to an actual monitoring space; and the smoke density estimation unit estimates the smoke density in the monitoring space when smoke particles determined by the smoke particle determination unit are identical to particles determined in advance as a monitoring object. In this case, by estimating the type of particles present in the monitoring space in the particle determination unit, it is possible to distinguish smoke particles, for example, from steam. Therefore, smoke can be detected more accurately than in the smoke sensor of a light scattering type or the smoke sensor of a light dimming type and it is possible to provide a smoke sensor suitable for use even in kitchens and bathrooms. Furthermore, because smoke density in the monitoring space is estimated when the smoke particles detected in the monitoring space are smoke particles determined in advance as a monitoring object, the computation processing necessary for subsequent estimation of smoke density can be omitted when the particles are not the monitoring object. Moreover, detailed properties of fire can be distinguished, for example, a case in which liquid particles of high viscosity, such as tar-like black smoke generated by fire in a fuel system, are generated can be discriminated from that of black smoke of typical fire. In addition, smoke density in the monitoring space can be estimated based on the variation amount of the output of the sound wave receiving unit from a standard value when an ultrasound wave of a specific frequency is provided to the monitoring space.

The data stored in the storage unit preferably include a relationship between a frequency of the sound wave provided by the sound wave generating unit and an output variation amount defined as a difference between an output of the sound wave receiving unit in the case the sound wave is received via the monitoring space in a standard state and an output of the sound wave receiving unit in the case the sound wave is received via the actual monitoring space, or a relationship between an output variation ratio obtained by dividing the output variation amount by a predetermined standard value and a frequency of the sound wave provided by the sound wave generating unit. Where the output variation ratio is used, even if the standard value of the output of the sound wave receiving unit fluctuates in response to the output frequency of the sound wave generating unit, the fluctuations of standard value can be prevented from affecting the estimation of the type of particles present in the monitoring space.

It is preferred that the sound wave generating unit include a single sound wave generating element having a function of providing a plurality of sound waves having different frequencies and that the control unit control the sound wave generating element so that the plurality of sound waves are provided successively to the monitoring space. In this case the sound wave generating unit can be reduced in size and cost by comparison with the configuration in which a plurality of sound wave generating elements capable of generating respective sound waves are provided.

It is preferred that the sound wave generating unit periodically provide a sound wave of a predetermined frequency to the monitoring space and that the signal processing unit change at least one from among a control condition of the sound wave generating unit and a signal processing condition of the output of the sound wave receiving unit on the basis of the output of the sound wave receiving unit obtained by providing the sound wave of the predetermined frequency to the monitoring space. In this case, the output fluctuations of the sound wave generating unit and sensitivity fluctuations of the sound wave receiving unit can be periodically canceled and smoke particles can be detected with stable sensitivity over a long period.

It is preferred that the sound wave generating unit be an ultrasound wave generating unit that generates an ultrasound wave when a thermal shock is provided to the air by temperature variations in a heat generating body caused by passing an electric current. In this case, the ultrasound wave generating unit has a flat frequency characteristic and can change the frequency of the generated ultrasound wave over a wide range. Furthermore, a single-pulse ultrasound wave with few reverberations can be provided from the ultrasound wave generating unit.

It is preferred that the ultrasound wave generating unit include a base substrate, a heat generating body layer provided on the base substrate, and a thermally insulating layer having a porous structure and provided between the heat generating body layer and the base substrate. In this case, because the thermally insulating layer is composed of a porous layer, thermal insulation property of the thermally insulating layer is improved, the ultrasound wave generating efficiency is increased, and power consumption is reduced by comparison with those in the case of a thermally insulating layer composed of a non-porous layer.

It is preferred that the control unit control the ultrasound wave generating unit so that a single-pulse ultrasound wave is provided to the monitoring space. In this case, the sound wave receiving unit is prevented from receiving the interference created by reflected waves from surrounding components and smoke density can be estimated with higher accuracy in the smoke density estimation unit.

It is further preferred that when an abnormality is detected by the signal processing unit, the control unit control the sound wave generating unit so as to generate an alarm sound at a frequency in an audible range that is different from the frequency of the ultrasound wave provided to the monitoring space. In this case, because the alarm sound can be generated from the sound wave generating unit, it is not necessary to provide a speaker or the like for outputting the alarm sound, and size and cost can be reduced.

It is preferred that the signal processing unit further include a sound velocity detection unit that determines a sound velocity based on a time required for a sound wave from the sound wave generating unit to reach the sound wave receiving unit, a temperature estimation unit that estimates a temperature of the monitoring space on the basis of the sound velocity, and a temperature determination unit that determines an abnormality of the monitoring space on the basis of a result obtained by comparing the temperature estimated by the temperature estimation unit with a predetermined threshold. In particular, it is preferred that the signal processing unit further include a fire determination unit that determines the presence of fire when the determination of at least one from among the smoke density determination unit and the temperature determination unit indicates an abnormality. In this case, when the smoke sensor is used as a fire sensor, the fire can be detected by the increase in temperature during fire occurrence, without using a separate temperature detection element, and the accuracy of fire detection is further increased by sensing both the smoke and the temperature. It is also preferred that a frequency correction unit be provided that corrects the frequency of the sound wave provided by the sound wave generating unit according to the temperature estimated by the temperature estimation unit by using the sound velocity found by the sound velocity detection unit. In this case, the apparatus configuration can be simplified by comparison with that in the case where separate means for finding the sound velocity is provided.

The smoke sensor of sound wave type in accordance with the present invention preferably includes a tubular body that is disposed between the sound wave generating unit and the sound wave receiving unit and narrows a diffusion range of the sound wave, an inner space of the tubular body being used as a propagation path of the sound wave. In this case, the diffusion of sound waves transmitted from the sound wave generating unit is inhibited because the sound waves pass inside the tubular body. As a result, the decrease in sound pressure caused by diffusion of sound waves between the sound wave generating unit and sound wave receiving unit can be inhibited. The advantage of such a configuration is that the sound pressure of the sound wave received by the sound wave receiving unit in a state in which no smoke particles are present in the monitoring space can be maintained at a high level, the variation amount of the output of the sound wave receiving unit becomes large in comparison with the variation amount of smoke density, and the SN ratio rises.

The sound wave generating unit preferably has a sound wave generating surface disposed so as to oppose a sound wave inlet port of the tubular body, and a surface area of the sound wave generating surface is preferably equal to or larger than an opening surface area of the sound wave inlet port. In this case, for example, when the tubular body has a straight shape, the sound wave provided from the sound wave generating surface of the sound wave generating unit propagates as a plane wave. Therefore, the reflection of sound wave on the side surface extending in the longitudinal direction of the tubular body and the interference between sound waves are prevented and the decrease in sound pressure can be avoided.

Further, the control unit preferably controls the sound wave generating unit so that an ultrasound wave of a resonance frequency inherent to the tubular body is continuously provided to the monitoring space over a transmission time that is longer than a propagation time required for the ultrasound wave to propagate between two ends in the longitudinal direction of the tubular body. In this case, because the tubular body functions as an acoustic tube, a resonance is induced inside the tubular body and the sound pressure of the sound wave from the sound wave generating unit increases. As a result, the variation amount of the output of the sound wave receiving unit related to the variation amount of smoke density increases and the SN ratio rises. Further, in the sound wave reflected by the end surfaces in the longitudinal direction of the tubular body due to resonance, the effective wave propagation distance extends correspondingly to the number of reflections and the variation amount of the output of the sound wave receiving unit related to the variation amount of smoke density further, increases.

It is also preferred that both end surfaces in the longitudinal direction of the tubular body be closed, the sound wave generating unit be disposed at one end surface, and the sound wave receiving unit be disposed in a location with a maximum pressure variation caused by the sound wave from the sound wave generating unit, on a side surface extending in the longitudinal direction. In this case, the output of the sound wave receiving unit related to the variation amount of smoke density can be remarkably increased. Furthermore, when a resonance is induced in an acoustic tube in which both end surfaces are closed, the resonance is caused by reflection of sound waves at the end surfaces. In particular, in the case of ultrasound waves, which have a short wavelength, the sound pressure decreases when the ultrasound wave is reflected at the end surface with even very small peaks and valleys present thereon, but providing the sound wave receiving unit on the side surface of the tubular body makes it possible to produce the end surface of the tubular body as a flat surface with fewer peaks and valleys than in the case in which the sound wave receiving unit is provided on the end surface of the tubular body. As a result, the sound pressure can be more effectively increased by the resonance, without suppressing the reflection of sound wave at the end surface of the tubular body by the sound wave receiving unit.

Further, it is preferred that the control unit control the sound wave generating unit so that a sound wave with a wavelength obtained by dividing a size of the inner space of the tubular body in the longitudinal direction by a natural number is provided to the monitoring space, and the sound wave receiving unit be disposed in a central portion in the longitudinal direction of the tubular body. In this case, because the sound wave generating unit produces a sound wave with a wavelength obtained by dividing a size of the inner space of the tubular body in the longitudinal direction by a natural number, the variations in pressure caused by the sound wave reach a maximum in the central portion in the longitudinal direction of the tubular body at all times. Therefore, where the above-described conditions relating to the wavelength are satisfied, the sound pressure can be detected in a position with a maximum pressure variation of the sound wave by the sound wave receiving unit disposed in the central portion in the longitudinal direction of the tubular body even when the frequency of the sound wave is different, and the cost can be reduced by comparison with the case in which sound wave receiving units are disposed in a plurality of locations.

The smoke sensor of sound wave type in accordance with the present invention preferably further includes a reflective member that reflects the sound wave from the sound wave generating unit toward the sound wave receiving unit. In this case, the sound wave from the sound wave generating unit is reflected at least once by the reflective surface, instead of reaching the sound wave receiving unit as a direct wave. Therefore, a resonance is easily induced between the sound wave generating unit and sound wave receiving unit. Further, it is preferred that the control unit control the sound wave generating unit so that the sound wave of a resonance frequency based on a propagation distance of the sound wave provided by the sound wave generating unit and received by the sound wave receiving unit is provided continuously to the monitoring space over an interval that is longer than a propagation time required for the sound wave to propagate from the sound wave generating unit to the sound wave receiving unit. The advantage of such a configuration is that a resonance is induced between the sound wave generating unit and sound wave receiving unit and the sound pressure rises, thereby increasing the SN ratio. Another merit is that the effective propagation distance of the sound wave reflected by the reflective member extends correspondingly to the number of reflections, and the variation amount of the output of the sound wave receiving unit related to the variation amount of smoke density further increases.

It is preferred that the reflective member include a first reflective plate disposed adjacently to the sound wave generating unit, and a second reflective plate disposed adjacently to the sound wave receiving unit so as to oppose the first reflective plate via the monitoring space. In this case, the sound wave from the sound wave generating unit is reflected by the reflective surface, and a resonance can be effectively induced between the sound wave generating unit and sound wave receiving unit. Further, it is preferred that at least one of the first reflective plate and second reflective plate has a concave curved surface facing the monitoring space. Because the sound wave from the sound wave generating unit is converged by the reflective surface onto the sound wave receiving unit, the decrease in sound pressure caused by diffusion of sound waves can be inhibited, the variation amount of the output of the sound wave receiving unit related to the variation amount of smoke density increases, and the SN ratio rises.

In the smoke sensor of another preferred embodiment of the present invention, the sound wave generating unit comprises a first sound wave generating unit that provides a sound wave to the monitoring space into which smoke can penetrate from an outer space, and a second sound wave generating unit that provides a sound wave to a reference space into which the smoke cannot penetrate, wherein the sound wave receiving unit comprises a first sound wave receiving unit that receives the sound wave from the first sound wave generating unit, and a second sound wave receiving unit that receives the sound wave from the second sound wave generating unit, and the signal processing unit detects an abnormality of the monitoring space by using the output of the first sound wave receiving unit and the output of the second sound wave receiving unit. In this case, the standard value corresponding to variations in ambient environment (for example, temperature) of the smoke sensor is compared with the actual measured output of the first sound wave receiving unit. Therefore, abnormalities of the monitoring space can be detected with better accuracy.

It is preferred that the smoke density estimation unit further include an output correction unit that estimates the smoke density in the monitoring space on the basis of a difference between the output of the first sound wave receiving unit and a standard value and corrects the output of the first sound wave receiving unit on the basis of variations with time in the output of the second sound wave receiving unit. In this case, even when the sound pressure of the sound wave from the first sound wave generating unit varies correspondingly to variations in the ambient environment of the smoke sensor or variations in the first sound wave generating unit or first sound wave receiving unit with time, or the attenuation ratio of sound wave during propagation in the air that is a propagation medium changes even when the smoke density is constant, or the sensitivity of the first sound wave receiving unit changes, the effect of output fluctuations of the first sound wave receiving unit caused by these variations and changes can be removed by correction with the output correction unit. Therefore, the occurrence rate of false detection can be inhibited and reliability of the smoke sensor can be increased.

In another preferred configuration, a tubular body is disposed between the sound wave generating unit and the sound wave receiving unit and has an inner space thereof used as a propagation path of the sound wave, wherein the tubular body has a partition wall that partitions the inner space into the monitoring space and the reference space, part of the tubular body that provides the monitoring space has a communication hole of a size allowing smoke to penetrate from an outer space into the monitoring space, the first sound wave generating unit and the second sound wave generating unit are configured by a single sound wave generating element disposed at one end of the tubular body so that sound waves are provided simultaneously to both the monitoring space and the reference space, and the first sound wave receiving unit and the second sound wave receiving unit are disposed at the other end of the tubular body so that the sound waves provided by the single sound wave generating element are received via the monitoring space and the reference space, respectively. In this case, because the first sound wave generating unit and second sound wave generating unit are composed of a single sound wave generating element, the first sound wave generating unit and second sound wave generating unit change in a similar matter with the passage of time. Therefore, even when the sound pressure of the sound wave from the first sound wave generating unit varies correspondingly to changes in the first sound wave generating unit with time, the effect of output fluctuations in the second sound wave generating unit caused by these variations can be reliably corrected by the above-described output correction unit and false detection is effectively reduced.

The reference space preferably has a smoke shielding portion having fine holes of a size so as to prevent the penetration of at least smoke. In this case, because the reference space communicates with the outer space via the fine holes, although the penetration of floating particles into the reference space is prevented, variations in the ambient environment of the fire sensor are reflected in the reference space via the fine holes. Therefore, the correction in the output correction unit can be adequately performed.

It is preferred that the control unit synchronously control the first sound wave generating unit and the second sound wave generating unit so that the output of the first sound wave receiving unit and the output of the second sound wave receiving unit have the same frequency and the same phase, and the signal processing unit detect an abnormality of the monitoring space by using a differential output equivalent to a difference between the output of the first sound wave receiving unit and the output of the second sound wave receiving unit. With such a configuration, the output fluctuations of the second sound wave receiving unit caused by variations in the ambient environment of the smoke sensor do not affect the differential output and, therefore, the accuracy of estimating the smoke density in the monitoring space is increased.

It is preferred that each of the first sound wave generating unit and the second sound wave generating unit have a function of providing a plurality of sound waves having different frequencies, the signal processing unit have a storage unit that stores data representing a relationship between the differential output and a frequency of the sound wave provided by the first sound wave generating unit that has been examined in advance under a plurality of test conditions that differ in a type of smoke present in the monitoring space and a smoke density, and a smoke particle determination unit that determines the type of smoke particles present in the monitoring space by using the data of the storage unit and the output of the first sound wave receiving unit obtained by providing each of the plurality of sound waves to an actual monitoring space, and the smoke density estimation unit estimate the smoke density in the monitoring space when smoke particles determined by the smoke particle determination unit are identical to particles determined in advance as a monitoring object. In such case, because the type of smoke particles present in the monitoring space is estimated in the smoke particle determination unit, for example, smoke particles can be distinguished from steam and a smoke sensor suitable for use in kitchens and bathrooms can be provided. Further, detailed properties of fire can be distinguished, for example, a case in which liquid particles of high viscosity, such as tar-like black smoke generated by fire in a fuel system, are generated can be discriminated from that of black smoke of typical fire. As a result, more accurate information can be provided with respect to the fire present in the monitoring space by comparison with the smoke sensors of a light scattering type and a light dimming type.

The data stored in the storage unit preferably include a relationship between a value obtained by dividing the differential output by the output of the second sound wave receiving unit, and the frequency of the sound wave outputted by the first sound wave generating unit. In this case, the fluctuations of the output of the second sound wave receiving unit can be prevented from affecting the estimation of the type of smoke particles present in the monitoring space.

In a preferred configuration, a partition is disposed between the monitoring space and the reference space, the monitoring space is defined between the first sound wave generating unit and one surface of the partition, the reference space is defined between the second sound wave generating unit and a surface on the opposite side of the partition, the first sound wave receiving unit and the second sound wave receiving unit are disposed at the partition and configured by a single differential sound wave receiving unit having a first wave receiving unit facing the monitoring space and a second wave receiving unit facing the reference space, and the differential sound wave receiving unit provides, as the differential output, a difference in sound pressure between a sound wave received by the first wave receiving unit and a sound wave received by the second wave receiving unit when the control unit synchronously controls the first sound wave generating unit and the second sound wave generating unit. The noise separately generated in the first sound wave receiving unit and second sound wave receiving unit, as in the case where the first sound wave receiving unit and second sound wave receiving unit are provided separately, is not superimposed on the differential output and the noise contained in the differential can be reduced, thereby increasing the SN ratio.

The signal processing unit preferably further includes an output correction unit that measures, as a reference value, the output of the differential sound wave receiving unit obtained when a sound wave is provided only from the second sound wave generating unit to the reference space and corrects the differential output on the basis of variations in the reference value with time. In this case, fluctuations of the variation amount of the differential output from the standard value can be removed by corrections in the output correction unit and smoke particles can be sensed with a stable accuracy over a long period even when the sensitivity of the differential sound wave receiving unit changes.

In the smoke sensor of yet another preferred embodiment of the present invention, the sound wave generating unit comprises a first sound wave generating unit that provides a first sound wave with a frequency that is higher than a fixed frequency at which the sound wave receiving unit has sensitivity and a second sound wave generating unit that provides a second sound wave with a frequency that is higher than the frequency of the first sound wave by the fixed frequency, the control unit controls the first sound wave generating unit and the second sound wave generating unit so that the first sound wave and the second sound wave are simultaneously provided to the monitoring space, and the sound wave receiving unit receives a beat wave produced by mutual interference between the first sound wave and the second sound wave in the monitoring space. In this case, the frequency of the beat wave received by the sound wave receiving unit can be made comparatively small, while setting a comparatively high frequency of the first sound wave and second sound wave. Thus, it is possible to increase the sensitivity by increasing the frequency of the dilatational wave received by the sound wave receiving unit, thereby increasing the SN ratio, while increasing the rate of sound pressure variations in the sound wave caused by smoke particles present in the monitoring space by raising the frequency of the sound wave from the sound wave generating unit.

Further, a configuration is preferred that has disposed therein a first tubular body that is disposed between the first sound wave generating unit and the sound wave receiving unit and narrows a diffusion range of the sound wave, an inner space of the first tubular body being used as a propagation path of the sound wave, and a second tubular body that is disposed between the second sound wave generating unit and the sound wave receiving unit and narrows a diffusion range of the sound wave, an inner space of the second tubular body being used as a propagation path of the sound wave, wherein the first tubular body and the second tubular body are so disposed with respect to the sound wave receiving unit that the sound wave provided from a sound wave emission port of the first tubular body and the sound wave provided from the sound wave emission port of the second tubular body mutually interfere before the sound wave receiving unit. In this case, the decrease in sound pressure caused by diffusion of the sound wave propagating in the monitoring space can be inhibited. Moreover, because the beat wave is induced outside the first tubular body and second tubular body, viscous resistance of the inner circumferential surface of each tubular body causes no attenuation of the beat wave even when the frequency of the beat wave received by the sound wave receiving unit is low. Therefore, the variation amount of the output of the sound wave receiving unit related to the variation of smoke density is increased and the SN ratio rises.

It is also preferred that a tubular body be included that is disposed between the sound wave receiving unit and one of the first sound wave generating unit and the second sound wave generating unit and narrows a diffusion range of the sound wave, an inner space of the tubular body being used as a propagation path of the sound wave, and the tubular body be so disposed with respect to the sound wave receiving unit that the sound wave provided from a sound wave emission port of the tubular body and the sound wave provided from the other of the first sound wave generating unit and the second sound wave generating unit mutually interfere before the sound wave receiving unit. In this case, by providing the tubular body, it is possible to inhibit the decrease in sound pressure caused by diffusion of the sound wave between the sound wave receiving unit and either of the first sound wave generating unit and the second sound wave generating unit. Furthermore, because the frequency of the sound wave from the other of the first sound wave generating unit and the second sound wave generating unit can be set without limitations imposed by the tubular body, the inherent frequency equivalent to the difference between the frequency of the sound wave from the first sound wave generating unit and the frequency of the sound wave from the second sound wave generating unit can be freely set. In other words, the advantage of such a configuration is that the beat wave frequency can be matched with a frequency at which the sensitivity of the sound wave receiving unit is high.

Other features of the present invention and effects thereof will be better understood from the following description of the best mode for carrying out the invention.

BRIEF DESCRIPTION OF THE DRAWINGS

FIG. 3 is a schematic cross-sectional view of an ultrasound wave generating element of the fire sensor;

FIGS. 4A and 4B are a schematic perspective view and a schematic cross-sectional view with a partial cut-out of a wave receiving element of the fire sensor;

FIG. 8 is a flowchart illustrating an operation example of the fire sensor of the second embodiment;

FIG. 37 is a schematic plan view of a fire sensor of yet another modification example of the eighth embodiment;

FIGS. 38A and 38B are a schematic side view and a schematic cross-sectional view of a fire sensor of a ninth embodiment of the present invention;

FIG. 45 is a schematic perspective view of a fire sensor of the twelfth embodiment;

FIG. 46 is a schematic perspective view of a fire sensor of a modification example the twelfth embodiment;

FIGS. 47A and 47B are a schematic cross-sectional view and a schematic plan view of a differential wave receiving element used in the twelfth embodiment;

BEST MODE FOR CARRYING OUT THE INVENTION

A fire sensor using ultrasound waves will be described below with reference to the appended drawings as a preferred embodiment of the smoke sensor of sound wave type in accordance with the present invention.

First Embodiment

Figure 1:
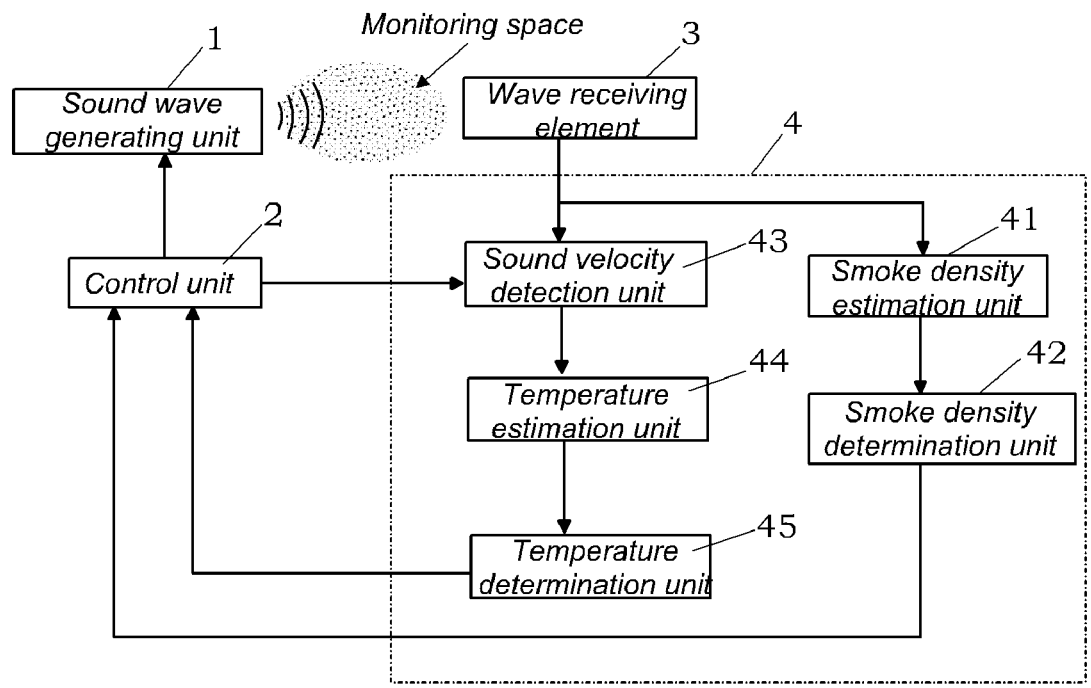
FIG. 1 is a block diagram of a fire sensor of a first embodiment of the present invention.

As shown in FIG. 1, the fire sensor of the present embodiment is mainly configured by a sound wave generating unit 1 that provides an ultrasound wave into a monitoring space, a control unit 2 that controls the sound wave generating unit 1, a wave receiving element 3 serving as an ultrasound wave receiving unit that detects a sound pressure of the ultrasound wave from the sound wave generating unit 1 via the monitoring space, and a signal processing unit 4 that determines whether fire is present based on the output of the wave receiving element 3.

Figure 2:
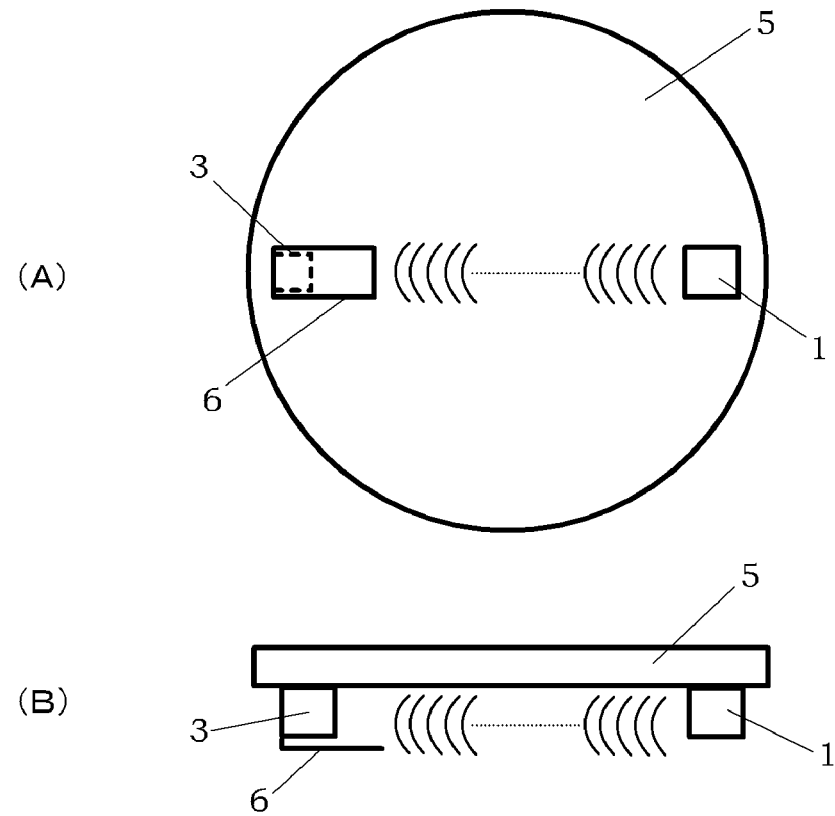
FIGS. 2A and 2B are a schematic plan view and a schematic side view of the fire sensor.

As shown in FIGS. 2A and 2B, the sound wave generating unit 1 and wave receiving element 3 are disposed opposite each other with a certain spacing therebetween on a circuit substrate 5 composed of a disk-shaped printed circuit board. The control unit 2 and signal processing unit 4 are provided on the circuit substrate 5. In FIG. 2A, a reference numeral 6 stands for a sound shielding wall provided around the wave receiving element 3 in order to prevent ultrasound waves generated by a source other than the sound wave generating unit 1 to fall on the wave receiving element 3. Forming the sound shielding wall 6 is effective in reducing false alarms in fire detection. Furthermore, a sound absorbing layer (not shown in the figure) that prevents the reflection of ultrasonic waves is provided on the circuit substrate 5, and the ultrasound wave reflected by the circuit substrate 5 can be prevented from interfering, as a reflected wave, and falling on the wave receiving element 3. Forming the sound absorbing layer is effective when a continuous wave is used as the ultrasound wave transmitted from the sound wave generating unit 1.

An ultrasound generating element that generates ultrasound waves when a thermal impact is provided to the air is used as the sound wave generating unit 1 of the present embodiment, and the ultrasound wave can be provided with a reverberation time shorter than that of a piezoelectric element. Further, a microphone of an electrostatic capacity type with a short generation period of a reverberation component contained in the received signals and a Q value of a resonance characteristic sufficiently smaller than that of a piezoelectric element is used as the wave receiving element 3.

As shown in FIG. 3, the sound wave generating unit 1 is mainly composed of a base substrate 11 composed of a single-crystal p-type silicon substrate, a thermal insulation layer (heat insulating layer) 12 composed of a porous silicon layer formed on the surface (upper surface in FIG. 3) of the base substrate 11, a heat-generating body layer 13 composed of a thin metal film formed as a heat-generating body on the upper surface of the thermal insulation layer 12, and a pair of pads 14 electrically connected to the heat-generating body layer 13 on the upper surface of the base substrate 11. The base substrate 11 has a rectangular shape in a plan view thereof, and the thermal insulation layer 12 and heat-generating body layer 13 are also formed to have a rectangular shape in a plan view thereof. An insulating film (not shown in the figure) composed of a silicon oxide film is formed on the region of the upper surface of the base substrate 11 where the thermal insulation layer 12 is not formed.

In the sound wave generating unit 1, where an electric current flows between the pads 14 at both ends of the heat-generating body layer 13, abrupt temperature variations are induced in the heat-generating body layer 13 and abrupt temperature variations (thermal shock) are induced in the air (medium) that is in contact with the heat-generating body layer 13. Therefore, the air that is in contact with the heat-generating body layer 13 expands when the temperature of the heat-generating body layer 13 rises and contracts when the temperature of the heat-generating body layer 13 drops. As a result, an ultrasound wave propagating in the air can be generated by appropriately controlling the supply of electric current to the heat-generating body layer 13. The ultrasound wave generating element constituting the sound wave generating unit 1 essentially generates an ultrasound wave propagating in the medium by converting abrupt temperature variations in the heat-generating body layer 13 accompanying the supply of electric current to the heat-generating body layer 13 into expansion and contraction of the medium. Therefore, a single-pulse ultrasound wave with smaller reverberations than those in the case of generating ultrasound waves by mechanical oscillations, as in a piezoelectric element, can be provided to the monitoring space.

The porous silicon layer constituting the thermal insulation layer 12 has a porosity of about 60% to about 70% and can be formed by performing anodic oxidation of part of the silicon substrate used as the base substrate 11 in an electrolytic solution composed of a liquid mixture of an aqueous solution of hydrogen fluoride and ethanol. The porous silicon layer formed by anodic oxidation contains a large number of silicon nanocrystals composed of microcrystalline silicon with a crystal grain size of a nanosize order. Thermal conductivity and heat capacity of the porous silicon layer decrease with the increase in porosity. Therefore, by making the thermal conductivity and heat capacity of the thermal insulation layer 12 lower than the thermal conductivity and heat capacity of the base substrate 11 and by making the product of thermal conductivity and heat capacity of the thermal insulation layer 12 sufficiently small by comparison with the product of thermal conductivity and heat capacity of the base substrate 11, it is possible to transmit the temperature variations in the heat-generating body layer 13 to the air. Further, efficient heat exchange can be obtained between the heat-generating body layer 13 and the air, and the base substrate 11 can efficiently receive the heat from the thermal insulation layer 12 and absorb the heat of the thermal insulation layer 12. Therefore, the heat from the heat-generating body layer 13 is prevented from accumulating in the thermal insulation layer 12.

A porous silicon layer with a porosity of about 60% that is formed by anodic oxidation of a single-crystal silicon substrate with a thermal conductivity of 148 W/(m·K) and a heat capacity of $1.63 \times 10^6$ J/(m$^3$·K) has a thermal conductivity of about 1 W/(m·K) and a heat capacity of about $0.7 \times 10^6$ J/(m$^3$·K), and the porous silicon layer with a porosity of about 70% has a thermal conductivity of about 0.12 W/(m·K) and a heat capacity of about $0.5 \times 10^6$ J/(m$^3$·K). The thermal insulating layer 12 of the present embodiment is formed by a porous silicon layer with a porosity of about 70%.

The heat-generating body layer 13 is formed from tungsten, which is a metal with a high melting point, but the material of the heat-generating body layer 13 is not limited to tungsten, and tantalum, molybdenum, yttrium, aluminum, and the like may be also used. In the sound wave generating unit 1, the thickens of the base substrate 11 is 300 to 700 μm, the thickness of the thermal insulation layer 12 is 1 to 10 μm, the thickness of the heat-generating body layer 13 is 20 to 100 nm, and the thickness of each pad 14 is 0.5 μm, but these values are merely exemplary and place no limitation on the aforementioned thicknesses. Further, Si is employed as a material of the base substrate 11, but the material of the base substrate 11 is not limited to Si, and other semiconductor materials that can be made porous by anodic oxidation, such as Ge, SiC, GaP, GaAs, and InP, may be also used. With all these materials, a porous layer formed by obtaining a porous structure in part of the base substrate 11 can be used as the thermal insulation layer 12.

The sound wave generating unit 1 generates an ultrasound wave following temperature variations in the heat-generating body layer 13 occurring when an electric current is passed to the heat-generating body layer 13 via a pair of pads 14. When a drive input waveform composed of a drive voltage waveform or drive current waveform supplied to the heat-generating body layer 13 is a sine waveform, for example, with a frequency f1, the frequency of temperature fluctuations occurring in the heat-generating body layer 13 theoretically becomes a frequency f2 that is twice as high as the frequency f1 of the drive input waveform, and an ultrasound wave with a frequency about twice as high as that of the drive input waveform f1 can be generated. Thus, the sound wave generating unit 1 of the present embodiment has a flat frequency characteristic and can change the frequency of the generated ultrasound wave within a wide range. Further, when a half-period isolated wave of a sine waveform is supplied as a drive input waveform between the pair of pads 14, a single-pulse ultrasound wave of about one period with little reverberations can be generated. Where such single-pulse ultrasound wave is used, interference caused by reflection can hardly occur. Therefore, the aforementioned sound absorbing layer can be omitted. Furthermore, because the thermal insulation layer 12 is composed of a porous layer, thermal insulation properties of the thermal insulation layer 12 are improved, ultrasound wave generation efficiency increases, and power consumption can be reduced by comparison with those of the thermal insulation layer 12 composed of a non-porous layer (for example, a SiO$_2$ film or the like).

The control unit 2 that controls the sound wave generating unit 1 is composed of a drive circuit that supplies a drive input waveform to the sound wave generating unit 1 and drives the sound wave generating unit 1 and a control circuit composed of a microcomputer that controls the drive circuit (this configuration is not shown in the figures).

As shown in FIGS. 4A and 4B, the microphone of an electrostatic capacity type that constitutes the wave receiving element 3 includes a rectangular frame 30 provided with a window orifice 31 that passes through in the thickness direction to the silicon substrate and a cantilever-type pressure-receiving portion 32 disposed in a bridge-like configuration between two opposite sides of the frame 30. A thermal oxidation film 35 is formed on the upper surface of the frame 30, a silicon oxide film 36 is formed on the thermal oxidation film 35, and a silicon nitride film 37 is formed on the silicon oxide film 36. One end of the pressure-receiving portion 32 is supported by the frame 30 via the silicon nitride film 37, and the other end is disposed so as to face the silicon nitride film 37 from above. A fixed electrode 34 composed of a thin metal film (for example, chromium film) is formed on the silicon nitride film 37 facing the other end of the pressure receiving portion 32, and a movable electrode 33 composed of a thin metal film (for example, a chromium film) is formed on the upper surface of the other end of the pressure receiving portion 32. A silicon nitride film 38 is formed on the lower surface of the frame 31. The pressure receiving portion 32 is formed by a silicon nitride film formed by a process different from that by which the silicon nitride films 37, 38 are formed.

In the wave receiving element 3 composed of the microphone of an electrostatic capacity type, a capacitor is formed by the fixed electrode 34 and movable electrode 33. Therefore, where the distance between the fixed electrode 34 and movable electrode 33 changes when the pressure receiving portion 32 receives a dilatational wave pressure, the electrostatic capacity between the electrodes also changes. Therefore, where a DC bias voltage is applied between pads (not shown in the figures) provided at the fixed electrode 34 and movable electrode 33, very small voltage variations are generated between the pads correspondingly to the sound pressure of the ultrasound wave, and the sound pressure of the ultrasound wave can be converted into an electric signal.

As shown in FIG. 1, the signal processing unit 4 includes a smoke density estimation unit 41 that estimates smoke density in the monitoring space between the sound wave generating unit 1 and wave receiving element 3 on the basis of the attenuation amount from the standard value of the output of the wave receiving element 3, a smoke density determination unit 42 that compares the smoke density estimated by the smoke density estimation unit 41 with a predetermined threshold and determines whether fire is present, a sound velocity detection unit 43 that finds a sound velocity on the basis of time required for the wave receiving element 3 to receive the ultrasound wave provided by the sound wave generating unit 1, a temperature estimation unit 44 that estimates the monitoring space temperature based on the sound velocity found by the sound velocity detection unit 43, and a temperature determination unit 45 that determines the presence of fire by comparing the temperature estimated by the temperature estimation unit 44 with an stipulated temperature. The signal processing unit 4 is configured by a microcomputer. Each of units 41 to 45 is realized by installing an appropriate program in the microcomputer. Further, the signal processing unit 4 is provided with an A/D converter or the like that performs analog-digital conversion of output signals of the wave receiving element 3.

The smoke density estimation unit 41 estimates smoke density on the basis of an attenuation amount from the standard value of the output of the wave receiving element 3. Where the frequency of the ultrasound wave from the sound wave generating unit 1 is constant, the attenuation amount increases almost proportionally to the smoke density in the monitoring space. Therefore, where relationship data (for example, a relationship equation of smoke density and attenuation amount) of smoke density and attenuation amount that have been measured in advance are stored, the smoke density can be estimated based on the attenuation amount.

The smoke density determination unit 42 determines that there is "No Fire" when the smoke density estimated by the smoke density estimation unit 41 is less than the threshold, and determines that "Fire is Present" when the estimated smoke density is equal to or higher than the threshold. In the latter case, the smoke density determination unit outputs a fire sensing signal to the control unit 2. When the control unit 2 receives the fire sensing signal, the control unit controls a drive input waveform to the sound wave generating unit 1 so that an alarm sound composed of an audible sound wave is generated from the sound wave generating unit 1. Because an alarm sound can thus be generated from the sound wave generating unit 1, it is not necessary to provide separately a speaker for outputting the alarm sound and the entire fire sensor can be reduced in size and cost.

The sound velocity detection unit 43 finds the sound velocity by using a time required for the wave receiving element 3 to receive the ultrasound wave provided by the sound wave generating unit 1 and the distance between the sound wave generating unit 1 and wave receiving element 3. The temperature estimation unit 44 estimates the temperature of the monitoring space from the sound velocity by using the well known equation describing the relationship between the sound velocity in the atmosphere and absolute temperature. The temperature determination unit 45 determines that there is "No Fire" when the temperature estimated by the temperature estimation unit 44 is less than the stipulated temperature. When the estimated temperature is equal to or higher than the stipulated temperature, the temperature determination unit determines that "Fire is Present" and outputs a fire sensing signal to the control unit 2. The control unit 2 controls the drive input waveform to the sound wave generating unit 1 so that an alarm sound is generated that is composed of an audible sound wave based on the fire sensing signal. In the present embodiment, a configuration is employed in which the fire sensing signal outputted by the fire density determination unit 42 or temperature determination unit 45 is outputted to the control unit 2, but this signal may be also outputted to an external notification device other than the control unit 2.

With the fire sensor of the above-described embodiment, the presence of fire is determined by comparing a smoke density estimated based on the attenuation amount from the reference value of the output of the wave receiving element 3 with the predetermined threshold. Therefore, the effect of background light that causes problems in smoke sensors of a light dimming type is eliminated and the occurrence rate of false alarm can be reduced. Furthermore, a labyrinth body that is necessary for smoke sensors of a light scattering type is unnecessary and smoke particles can easily diffuse into the monitoring space when fire occurs. Therefore, the responsiveness is increased by comparison with that of smoke sensors of a light scattering type. In addition, in the fire sensor of the present embodiment, the monitoring space temperature is estimated based on the sound velocity found by the sound velocity detection unit 43 and the presence of fire is determined based on the estimated temperature. Therefore, fire can be sensed by the rise in temperature when the fire occurs, without using a separate temperature detection element, and the occurrence of fire can be sensed more accurately.

Second Embodiment

Figure 5:
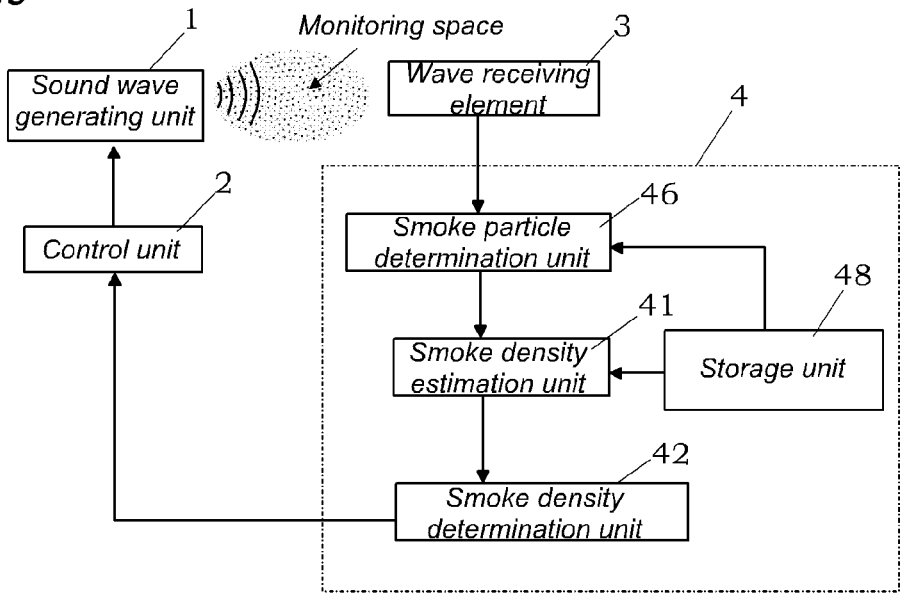
FIG. 5 is a block diagram of a fire sensor of a second embodiment of the present invention.

The fire sensor of the present embodiment is substantially identical to that of the first embodiment, except that the configurations of the control unit 2 and signal processing unit 4 are different, as shown in FIG. 5. Therefore, structural elements identical to those of the first embodiment are assigned with identical reference numerals and redundant explanation thereof is omitted.

Figure 6:
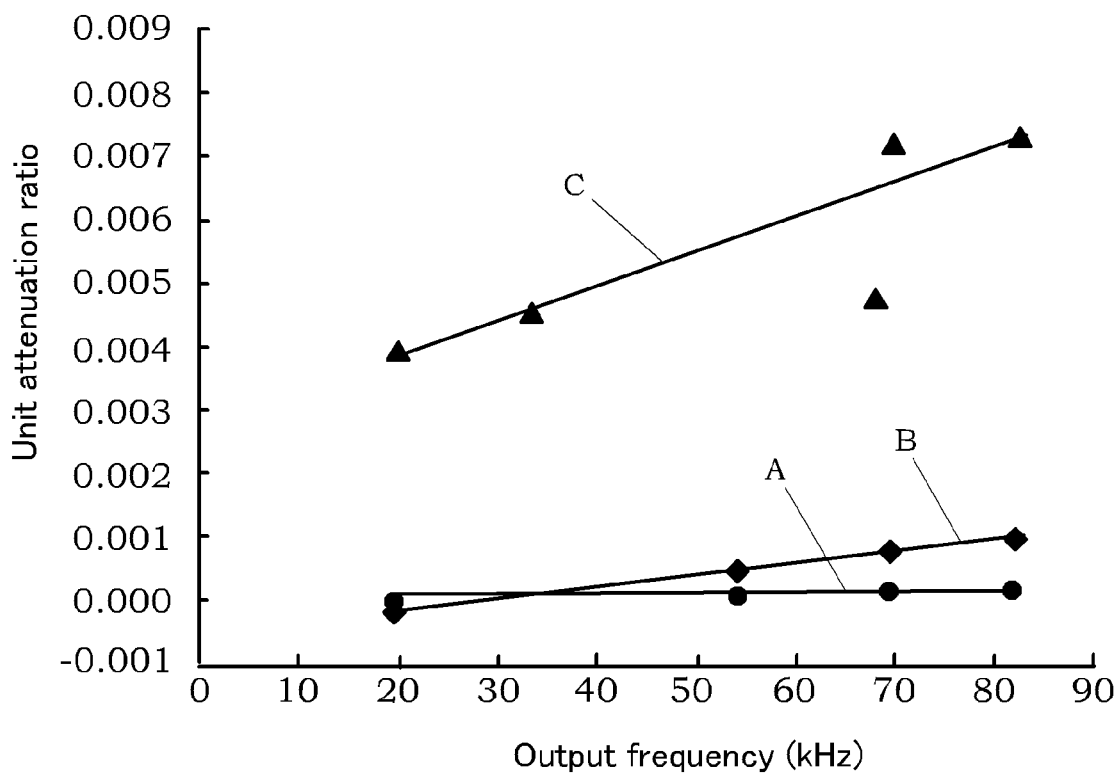
FIG. 6 is a graph illustrating the relationship between the output frequency of the ultrasound wave generating unit and the unit attenuation ratio of sound pressure received by the wave receiving element.
Figure 7:
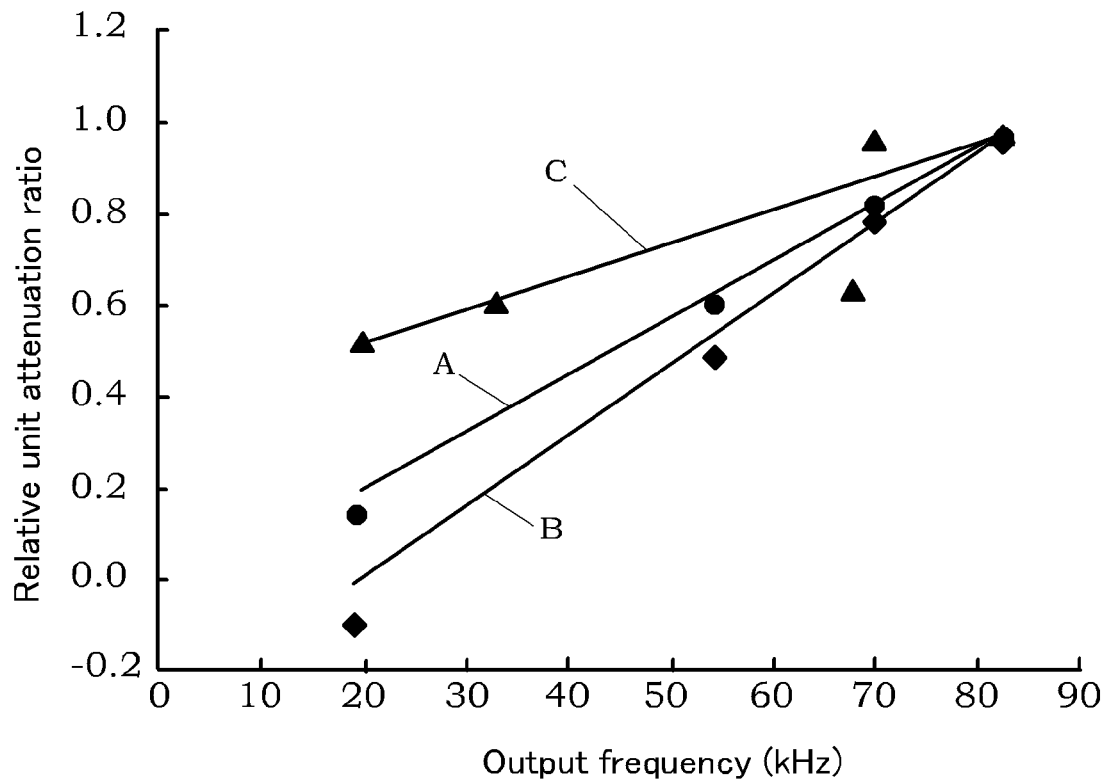
FIG. 7 is a graph illustrating the relationship between the output frequency of the ultrasound wave generating unit and the relative unit attenuation ratio of sound pressure received by the wave receiving element.

As shown in FIG. 6, preliminary experiments have confirmed that the relationship between the output frequency of the sound wave generating unit 1 and the unit attenuation ratio of sound pressure differs depending on the type of smoke particles present (floating) in the monitoring space. Here, the attenuation ratio of sound pressure will be defined as $(I_0-I_x)/I_0$, where $I_0$ stands for a sound pressure (referred to hereinbelow as "standard sound pressure") received by the wave receiving element 3 in a state in which smoke particles are not present in the monitoring space and $I_x$ is a sound pressure received by the wave receiving element 3 in a state in which smoke particles with a density of x %/m, as estimated by a smoke density meter of a light dimming type, is present in the monitoring space. In particular, the attenuation at x=1 is defined as a unit attenuation ratio. The standard sound pressure $I_0$ and sound pressure $I_x$ are assumed to be detected under identical conditions, with the exception of presence/absence of smoke particles in the monitoring space. In FIG. 6, "A" is an approximation curve (black circles are measurement data) representing the relationship between the output frequency and unit attenuation ratio of sound pressure in the case where black smoke particles are present in the monitoring space, "B" is an approximation curve (black circles are measurement data) representing the relationship between the output frequency and unit attenuation ratio of sound pressure in the case where white smoke particles are present in the monitoring space, and "C" is an approximation curve (black triangles are measurement data) representing the relationship between the output frequency and unit attenuation ratio of sound pressure in the case where steam particles are present in the monitoring space. The unit attenuation ratio shown herein represents data relating to the output frequency obtained when the distance between the sound wave generating unit 1 and wave receiving element 3 is 30 cm. The data at the right end in FIG. 6 correspond to an output frequency of 82 kHz. FIG. 7 shows the results obtained by taking the data at an output frequency of 82 kHz as 1 and normalizing the unit attenuation ratio for each output frequency. Thus, in FIG. 7, the output frequency is plotted against the abscissa and a relative unit attenuation ratio is plotted against the ordinate. The size of white smoke particles is about 800 nm, the size of black smoke particles is about 200 nm, and the size of steam particles is from several micrometers to about 20 μm.

In the present embodiment, the control unit 2 controls the sound wave generating unit 1 on the basis of the above-described relationship, so that a plurality of ultrasound waves of different frequencies are successively provided to the monitoring space. A specific feature of the signal processing unit 4 is that it includes a storage unit 48 that stores at least the standard output of the wave receiving element 3 (output of the wave receiving element 3 related to the standard sound pressure), data representing the relationship between the output frequency of the sound wave generating unit 1 corresponding to the smoke particle density and the type of smoke particles present in the monitoring space and the relative unit attenuation ratio of the output of the wave receiving element 3 (data extracted from the above-described FIG. 7), and a unit attenuation ratio at a specific frequency (for example 82 kHz) for the smoke particles (data extracted from the above-described FIG. 6) and a smoke particle determination unit 46 that evaluates the type of smoke particles present in the monitoring space on the basis of the output of the wave receiving element 3 for the ultrasound wave of each frequency provided from the sound wave generating unit 1 to the actual monitoring space and the relationship data stored in the storage unit 48. The smoke density estimation unit 41 evaluates the density of smoke in the monitoring space on the basis of the attenuation amount from the standard value of the output of the wave receiving element 3 relating to the ultrasound wave of a specific frequency (for example 82 kHz) with respect to the smoke particles estimated by the smoke particle determination unit 46. The smoke density determination unit 42 determines the presence or absence of fire by comparing the smoke density estimated by the smoke density estimation unit 41 with a predetermined threshold.

Figure 9:
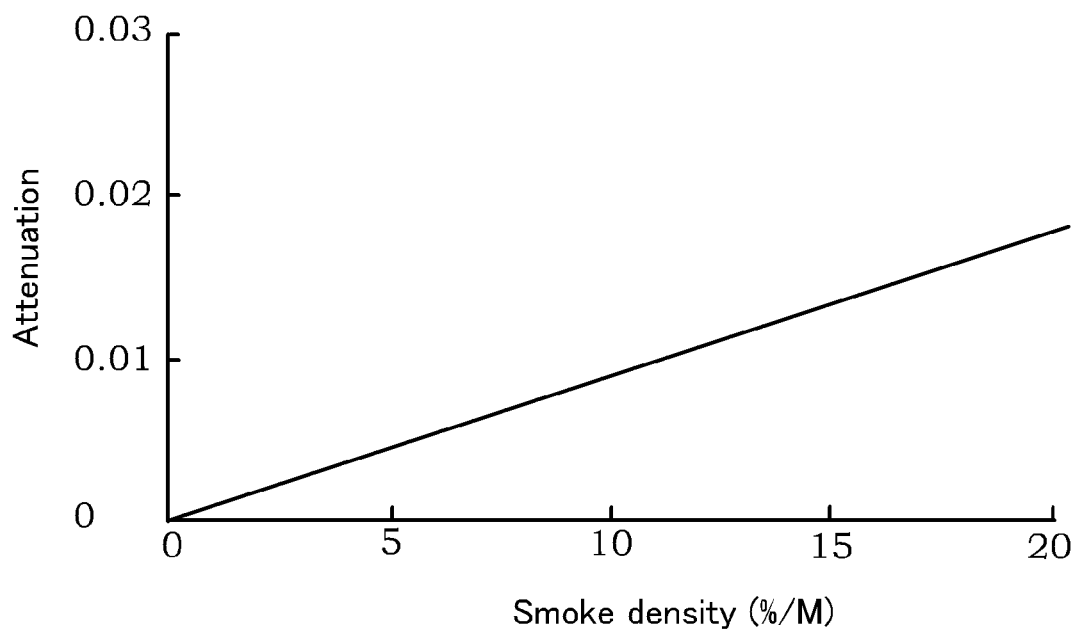
FIG. 9 is a graph illustrating the relationship between the smoke density and the attenuation ratio of an ultrasound wave of specific frequency.

An operation example of the fire sensor of the present embodiment will be explained below with reference to the flowchart shown in FIG. 8. First, a plurality of ultrasound waves are successively provided from the sound wave generating unit 1 to the monitoring space, and the output of the wave receiving element 3 corresponding to each ultrasound wave is measured with the signal processing unit 4 (step S11). The smoke particle determination unit 46 finds the attenuation ratio of sound pressure from the output of the wave receiving element 3 and the standard output stored in the storage unit 48 for each output frequency (step S12) and computes a ratio of the attenuation ratio of sound pressure at an output frequency of 20 kHz to the attenuation ratio of sound pressure at an output frequency of 82 kHz (step S13). A ratio of the relative unit attenuation ratio at an output frequency of 20 kHz to the relative unit attenuation ratio at an output frequency of 82 kHz (in the case shown in FIG. 7, this ratio is 0 for white smoke, 0.2 for black smoke, and 0.5 for steam) is stored in the storage unit 48 as data representing the relationship between the output frequency of the sound wave generating unit 1 and the relative unit attenuation ratio of the output of wave receiving element 3. The smoke particle determination unit 46 compares the computed attenuation ratio with the relationship data stored in the storage unit 48 and estimates the smoke particles of a type with the ratio of attenuation ratios closest to that in the relationship data as the smoke particles present in the monitoring space (step S14). For example, when the smoke particles are white smoke, as shown in FIG. 9, the relationship between the smoke density measured with the smoke density meter of a light dimming type and the attenuation ratio of sound pressure is shown by a straight line. In the present embodiment, where the estimated type of smoke particles is white smoke or black smoke (smoke particles that are the object of monitoring), the processing flow moves to the processing in the smoke density estimation unit 41 (step S15). Therefore, where the type of smoke particles is estimated as steam, because it is not fire, subsequent processing is omitted. The smoke density estimation unit 41 computes a ratio of the attenuation ratio of the output of the wave receiving element 3 relating to the ultrasound wave of a specific frequency (for example 82 kHz) to the unit attenuation ratio stored in the storage unit 48 for smoke particles of the estimated type, and where the value of this ratio is y, estimates that the smoke density in the monitoring space is equivalent to the smoke density y %/m in the evaluation performed with the smoke density meter of a light dimming type (step S16). The smoke density determination unit 42 compares the smoke density estimated in step S16 with a predetermined threshold (for example, a smoke density of 10%/m in the evaluation performed with the smoke density meter of a light dimming type), determines "No Fire" when the estimated smoke density is less than the threshold, or determines "Fire is Present" when the estimated smoke density is equal to or higher than the threshold and outputs a fire sensing signal to the control unit 2.

In the present explanation, the attenuation ratio at an output frequency of 82 kHz and the attenuation ratio at an output frequency of 20 kHz are used, but this combination of output frequencies is not limiting. Thus, the output frequencies of different combinations may be used or the attenuation ratio relating to a larger number of output frequencies may be used, and in this case the estimation accuracy of the type of smoke particles can be increased. Further, in the present embodiment, the smoke density estimation unit 41 performs estimation with respect to one specific frequency, but it is also possible to use a plurality of frequencies as specific frequencies and find an average value of smoke densities estimated for each specific frequency. In this case, the estimation accuracy of smoke density is also increased. Similarly to the smoke density estimation unit 41 and smoke density determination unit 42, the smoke particle determination unit 46 can be implemented by installing an appropriate program in a microcomputer constituting the signal processing unit 4.

In order to increase the estimation accuracy of smoke particle type in the smoke particle determination unit 46, the control unit 2 changes the frequency of the ultrasound wave provided from the sound wave generating unit 1 from a lower limit frequency (for example, 20 kHz) to an upper limit frequency (for example 82 kHz) in a predetermined frequency range (for example 20 kHz to 80 kHz). In the present embodiment, the control is so performed that ultrasound waves of four kinds with different frequencies are successively provided to the monitoring space, but the number of frequencies of ultrasound waves provided from the sound wave generating unit 1 is not limited to four, and ultrasound waves of a plurality of kinds may be provided. For example, when ultrasound waves of two kinds are provided, the load on the control unit 2 and signal processing unit 4 can be reduced and the control unit 2 and signal processing unit 4 can be simplified by comparison with those employed when ultrasound waves of three or more kinds are used.

In the present embodiment the ultrasound wave generating element explained in Embodiment 1 is used as the sound wave generating unit 1 and single-pulse ultrasound waves can be generated. Therefore, where the ultrasound waves provided successively to the monitoring space are in the form of single-pulse ultrasound waves with mutually different frequencies, the cost and power consumption can be reduced by comparison with the case in which a plurality of piezoelectric elements with different resonance frequencies are used as the sound wave generating unit 1 and an ultrasound wave is continuously provided from each piezoelectric element. Moreover, because a plurality of ultrasound waves are generated with one ultrasound wave generating element, the size and cost of the sound wave generating unit 1 can be reduced by comparison with those of the case in which a plurality of ultrasound wave generating elements are used for generating ultrasound waves of various kinds.

The relationship data stored in the storage unit 48 may represent the relationship between the output frequency of the sound wave generating unit 1 and the standard value of the output of the wave receiving element 3, or may be the relationship data employing the attenuation amount of the output of the wave receiving element 3 from the standard value, or the attenuation ratio obtained by dividing the attenuation amount of the output of the wave receiving element 3 from the standard value by the standard value ($I_0$), or a unit attenuation ratio, instead of the above-described relative unit attenuation ratio.

With the fire sensor of the present embodiment, for the same reasons as have been described with respect to the first embodiment, the responsiveness can be increased over that of a fire sensor of a light scattering type and the occurrence rate of false alarm can be reduced by comparison with that of a fire sensor of a light dimming type. Moreover, because solid smoke particles can be distinguished from steam by estimating the type of smoke particles present in the monitoring space with the smoke particle determination unit 46, the occurrence rate of false alarm caused by steam can be reduced by comparison with that of a fire sensor of a light scattering type and a fire sensor of a light dimming type, and the fire sensor can be also used in kitchens or bathrooms. Furthermore, because the smoke particle determination unit 46 makes it possible to distinguish white smoke particles from black smoke particles, information relating to properties of fire can be obtained. In addition, because dust that floats in the air when the inside of the room where the fire sensor is disposed is cleaned or when electric works are conducted at the ceiling can be distinguished from the smoke particles, the sensor effectively reduces the occurrence of error caused by dust and the like.

Figure 10:
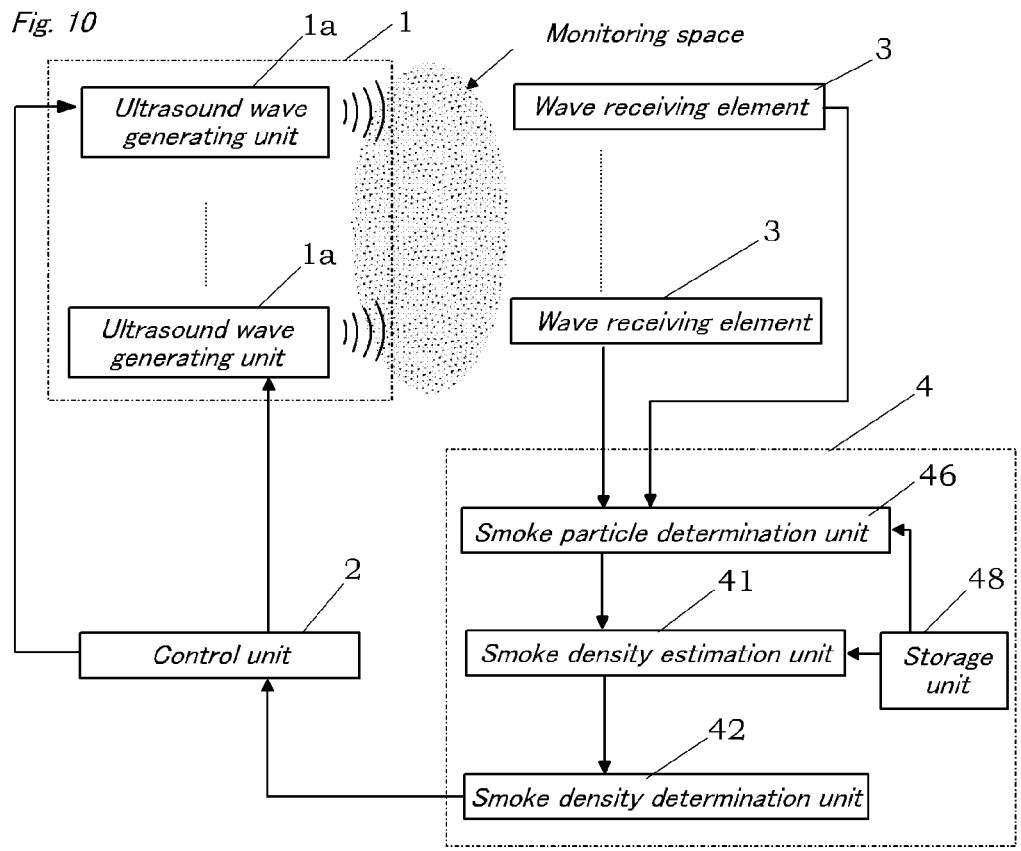
FIG. 10 is a block diagram of a fire sensor of a first modification example of the second embodiment.

As a first modification example of the present embodiment, the sound wave generating unit 1 may be configured by a plurality of ultrasound wave generating elements 1a that have mutually different output frequencies, as shown in FIG. 10. In this case, the sound pressure of ultrasound waves from the sound wave generating unit 1 can be increased by using elements generating ultrasound waves by mechanical oscillations, such as piezoelectric elements, as the ultrasound wave generating elements 1a and driving the ultrasound wave generating elements 1a at respective resonance frequencies. The advantage of increasing the sound pressure of ultrasound waves from the sound wave generating unit 1 is that the fluctuation range of the sound pressure of ultrasound waves received by the wave receiving element 3 expands, thereby increasing the variation amount of the output of the wave receiving element 3 related to the variation amount of smoke density and rising the S/N ratio. In this configuration, a plurality of wave receiving elements 3 corresponding to respective ultrasound wave generating elements 1a are provided and the wave receiving elements 3 receive ultrasound waves from corresponding ultrasound wave generating elements 1a. Therefore, by using a piezoelectric element with a comparatively large Q value of the resonance characteristic as each wave receiving element 3 and using the wave receiving elements 3 to receive ultrasound waves at respective resonance frequency, it is possible to increase the sensitivity of the wave receiving elements 3 and rise the SN ratio. In this case, it is also possible to drive a plurality of the ultrasound wave generating elements 1a at once and generate a plurality of ultrasound waves simultaneously, instead of driving the ultrasound wave generating elements 1a sequentially and transmitting a plurality of ultrasound waves sequentially. Where a plurality of the ultrasound waves are generated simultaneously, by detecting the attenuation of sound pressure of a plurality of ultrasound waves at the same time, it is possible to detect the attenuation amount of sound pressure of a plurality of ultrasound waves under identical conditions, this detection being unaffected by changes in the monitoring space with time (for example, changes in the density of smoke particles with time), and the type of smoke particles and smoke density can be estimated more accurately.

Figure 11:
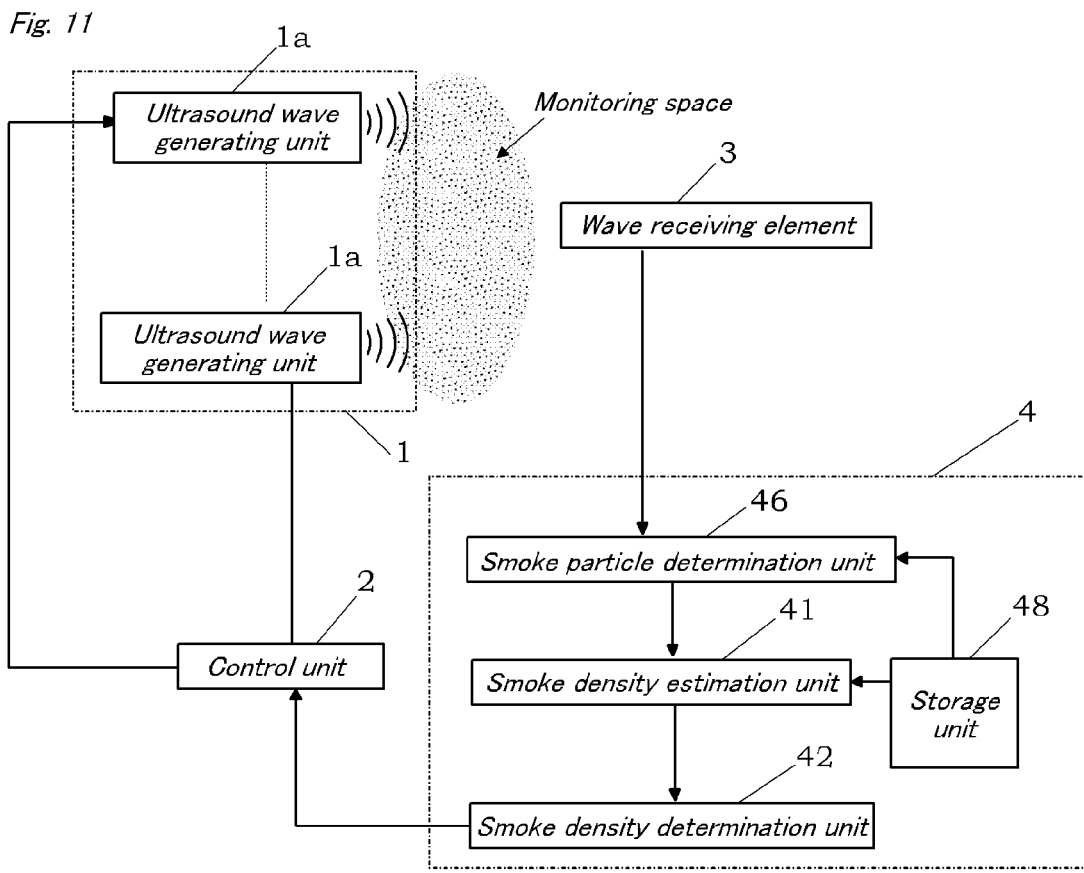
FIG. 11 is a block diagram of a fire sensor of a second modification example of the second embodiment.

In a second possible modification example of the present embodiment, as shown in FIG. 11, a single wave receiving element 3 is provided for the sound wave generating unit 1 composed of a plurality of ultrasound wave generating elements 1a, the ultrasound wave generating elements 1a are successively driven, a plurality of ultrasound waves are provided successively to the monitoring space, and this plurality of ultrasound waves are successively received by the signal wave receiving element 3. In this case, it is preferred that an element with a small Q value of resonance characteristic, for example, such as a microphone of an electrostatic capacity type explained in the first embodiment, be used as the wave receiving element 3. With the configuration shown in FIG. 11, the cost of the wave receiving elements 3 and the size of the fire sensor can be reduced by comparison with those of the configuration using a plurality of wave receiving elements 3.

Figure 12:
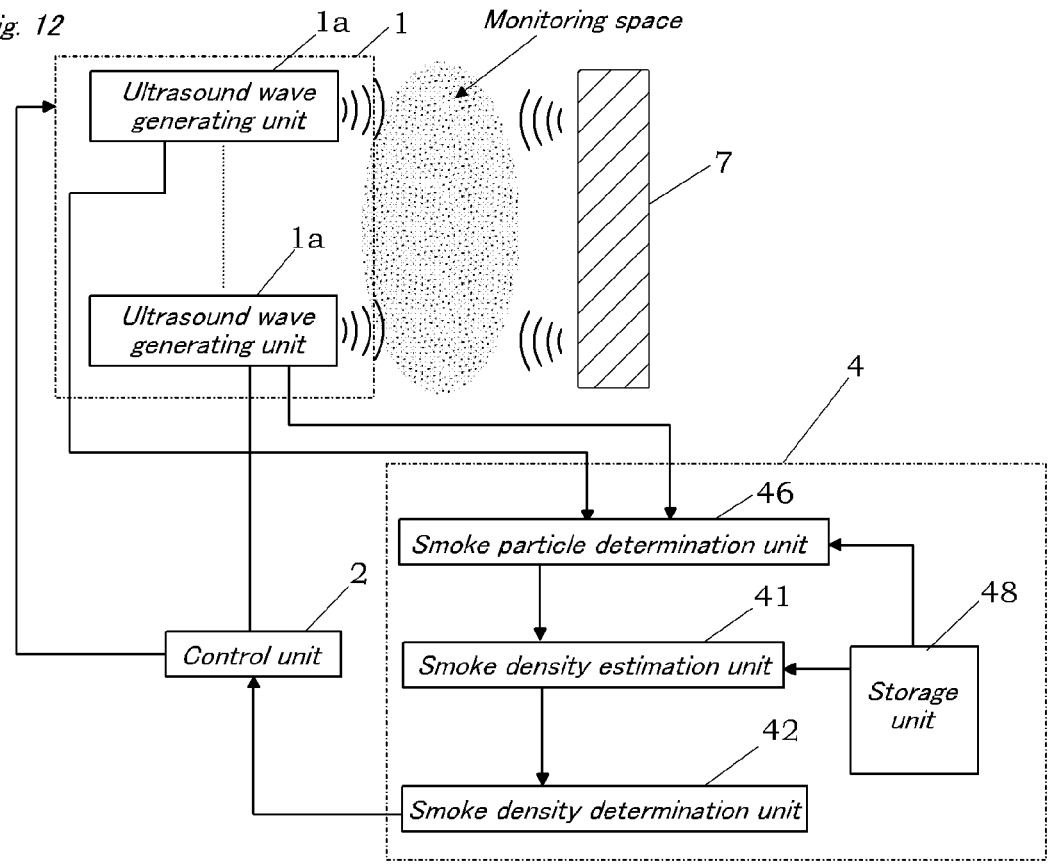
FIG. 12 is a block diagram of a fire sensor of a third modification example of the second embodiment.

In a third possible modification example of the present embodiment, as shown in FIG. 12, an ultrasound wave generating element 1a may be used also as the wave receiving element 3 by using an ultrasound wave generating element 1a that can be employed for both transmitting and receiving ultrasound waves, such as a piezoelectric ultrasound sensor, and connecting the ultrasound wave generating element 1a not only to the control unit 2, but also to the signal processing unit 4. In this modification example, the sound wave generating unit 1 is configured by a plurality of ultrasound wave generating elements 1a, and by disposing a reflective wall 7 that reflects the ultrasound waves provided from the ultrasound wave generating elements 1a toward the ultrasound wave generating elements 1a opposite the sound wave generating unit 1, it is possible to receive each reflected wave of ultrasound waves from the ultrasound wave generating elements 1a. In this case an ultrasound wave reciprocates between the reflective wall 7 and ultrasound wave generating elements 1a and is received by the ultrasound wave generating element 1a that functions as the wave receiving element 3. Therefore, the space between the ultrasound wave generating elements 1a and reflective wall 7 becomes the monitoring space. In this case, although the reflective wall 7 is necessary, the cost can be reduced due to the reduced number of elements.

Figure 13:
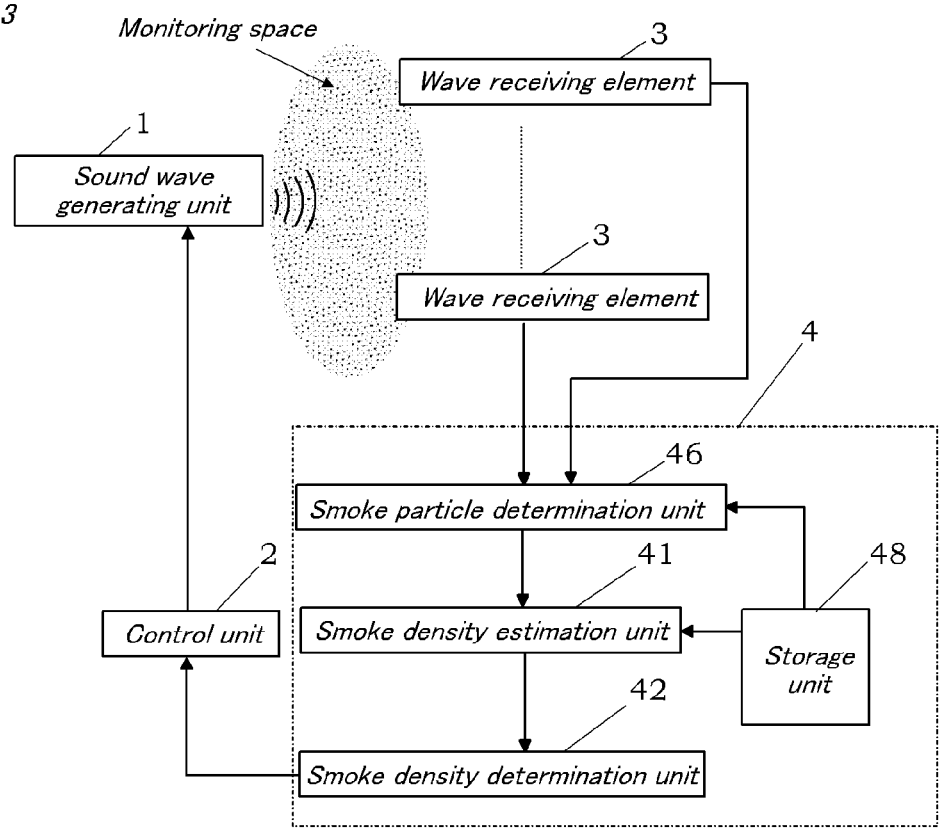
FIG. 13 is a block diagram of a fire sensor of a fourth modification example of the second embodiment.

In a fourth possible modification example of the present embodiment, as shown in FIG. 13, a single ultrasound wave generating element explained in the first embodiment is used as the sound wave generating unit 1, and the control unit 2 successively changes the frequency of the drive input waveform provided to the sound wave generating unit 1, thereby providing a plurality of ultrasound waves of different frequencies to the monitoring space, and a plurality of wave receiving elements 3 are provided. In this case, by using a piezoelectric element with a comparatively large Q value of resonance characteristic as the wave receiving element 3 and using each wave receiving element 3 for receiving the ultrasound wave of a respective resonance frequency, it is possible to improve the sensitivity of wave receiving element 3, thereby increasing the SN ratio. In a configuration in which a plurality of ultrasound waves are received by one wave receiving element 3, where the sensitivity of the wave receiving element 3 is different for each frequency, a spread in SN ratio occurs between the ultrasound waves, but in the above-described configuration in which the reception of ultrasound waves of each kind is performed with individual wave receiving elements 3, the uniformity of sensitivities of wave receiving elements 3 is improved, thereby inhibiting the spread in SN ratios between the ultrasound waves.

In the above-described embodiment, it is preferred that the signal processing unit 4 periodically change at least one set of conditions from among the conditions under which the control unit 2 controls the sound wave generating unit 1 and signal processing conditions of the output of wave receiving element 3, so as to cancel the sensitivity fluctuations of the wave receiving element 3 or output fluctuations of the sound wave generating unit 1, based on the output of the wave receiving element 3 corresponding to an ultrasound wave of a predetermined frequency (for example, a frequency of 82 kHz that is equal to the above-described specific frequency). The accuracy of fire determination with such fire sensor can be maintained over a long period.

In the fire sensor of the present embodiment, the signal processing unit 4 may be also provided with a sound velocity detection unit 43, temperature estimation unit 44, and temperature determination unit 45, in the same manner as in the first embodiment.

Further, in addition to an integrated fire sensor configuration in which the sound wave generating unit 1, control unit 2, wave receiving element 3, and signal processing unit 4 are provided at one circuit substrate 5 and accommodated in a case (not shown in the figure), a fire sensor of a detachable type may be configured by disposing opposite each other a sound wave generating unit including the sound wave generating unit 1 and control unit 2 and a sound wave receiving unit including the wave receiving element 3 and signal processing unit 4. Further, the sound wave generating unit 1 is not limited to the ultrasound wave generating element shown in FIG. 3, and it is also possible to use a thin aluminum plate as a heat generating body and generate ultrasound waves by thermal shocks induced by abrupt temperature variations in the heat generating body occurring when an electric current is passed through the heat generating body.

In the above-described embodiments, where the control unit 2 controls the sound wave generating unit 1 so as to generate an ultrasound wave at a frequency having an insect repellent effect, it is possible to prevent insects from penetrating into the monitoring space and reduce the occurrence rate of false alarm caused by insects. For example, ultrasound waves at a frequency having an insect repellent effect may be periodically generated separately from the ultrasound waves that are provided from the sound wave generating unit 1 for estimating the smoke density. Alternatively, the frequency of ultrasound waves transmitted from the sound wave generating unit 1 for estimating the smoke density may be set to a frequency having an insect repellent effect.

Third Embodiment

Figure 14:
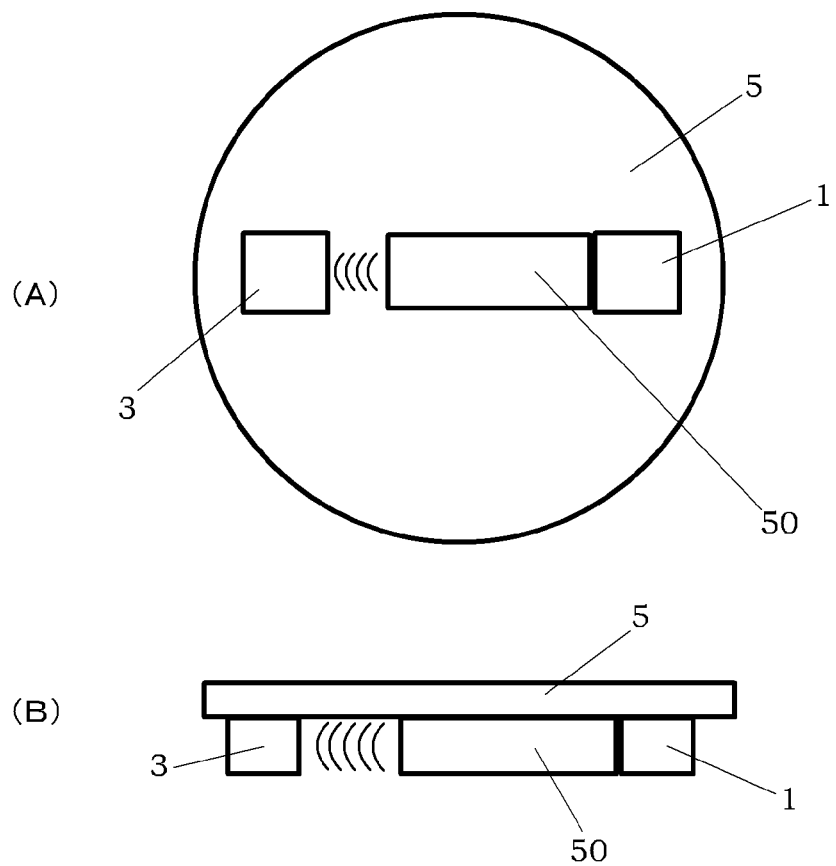
FIGS. 14A and 14B are a schematic plan view and a schematic side view of a fire sensor of the third embodiment of the present invention.

The fire sensor of the present embodiment is substantially identical to that of the first embodiment, except that a tubular body 50 that narrows the diffusion range of ultrasound waves and has the inner space thereof used as a propagation path for ultrasound waves is disposed between the sound wave generating unit 1 and wave receiving element 3, as shown in FIG. 14A and FIG. 14B. Therefore, structural elements identical to those of the first embodiment are assigned with identical reference numerals and redundant explanation thereof is omitted.

The tubular body 50 is disposed in at least part of the propagation path of ultrasound waves in the monitoring space. More specifically the tubular body 50 of the present embodiment has an angular tubular structure of an almost rectangular parallelepiped in which two end surface in the longitudinal direction are open, and one end surface in the longitudinal direction (right end surface in FIG. 14A) is disposed close to the sound wave generating unit 1. As a result, this end surface is closed by the sound wave generating unit 1. The other end surface (left end surface in FIG. 14A) is at a predetermined distance from the wave receiving element 3. By providing the tubular body 50, it is possible to prevent the diffusion of ultrasound waves transmitted by the sound wave generating unit 1 and the decrease in sound pressure.

Figure 15:
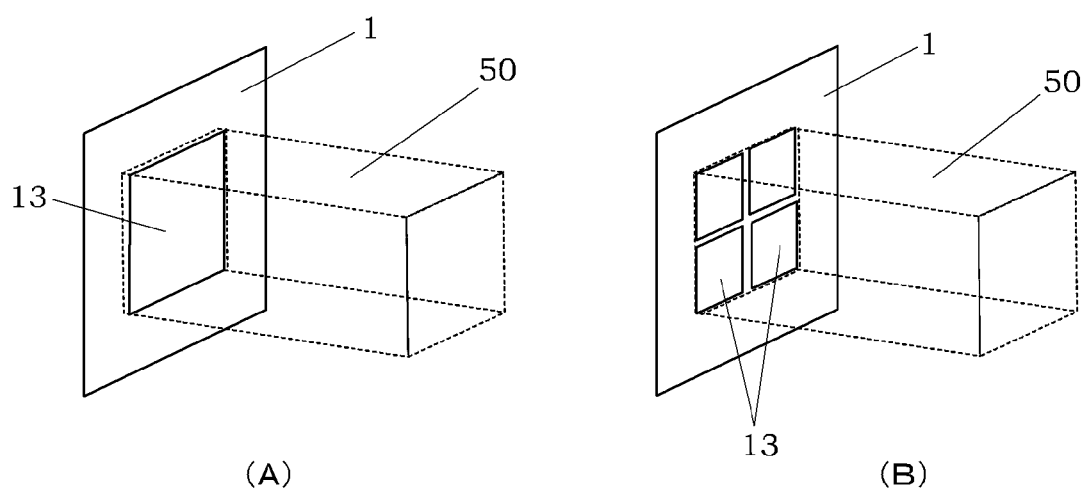
FIGS. 15A and 15B are schematic perspective views illustrating a tubular body disposed between a sound wave generating unit and a wave receiving element.

Further, in the fire sensor of the present embodiment, as shown in FIG. 15A, the surface of the heat-generating body layer 13 of the ultrasound wave generating element constituting the sound wave generating unit 1 (see FIG. 3) is disposed opposite an ultrasound wave inlet port of the tubular body 50 and formed in a shape identical to or larger than, preferably almost equal in size to the ultrasound wave inlet port. For example, when the opening surface of the ultrasound wave inlet port of the tubular body 50 has a square shape with a side of 10 mm, the surface of the heat-generating body layer 13 has a square shape with a side of 10 mm. With such a configuration, abrupt temperature variations of the heat-generating body layer 13 are uniformly transmitted to the entire area of the ultrasound wave inlet port of the tubular body 50. As a result, ultrasound waves from the sound wave generating unit 1 propagate as a planar wave inside the tubular body 50. Therefore, the decrease in sound pressure of ultrasound waves can be prevented without causing interference between the ultrasound waves reflected at the side surface of the tubular body 50.

Alternatively, when the sound wave generating unit 1 is configured by a plurality of ultrasound wave generating elements, as shown in FIG. 15B, and these ultrasound wave generating elements are driven synchronously, by disposing the ultrasound wave generating surface of the sound wave generating unit 1 formed by arranging the plurality of ultrasound wave generating elements side by side opposite the ultrasound wave inlet port of the tubular body 50 and forming this surface in a shape identical to or larger than, preferably almost equal in size to the ultrasound wave inlet port, it is possible to obtain the effect identical to that obtained with the above-described configuration shown in FIG. 15A. For example, when the opening surface of the ultrasound wave inlet port of the tubular body 50 has a square shape with a side of 10 mm, the heat-generating body layer 13 of each ultrasound wave generating element may have a square shape with a side of 5 mm and an ultrasound wave generating surface of a square shape with a side of 10 mm may be formed by arranging these four ultrasound wave generating elements side by side.

Figure 16:
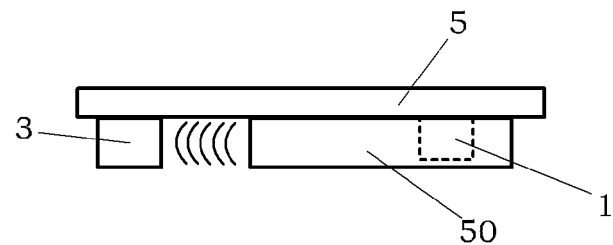
FIG. 16 is a schematic side view illustrating a mutual arrangement of the sound wave generating unit, wave receiving element, and tubular body.
Figure 17:
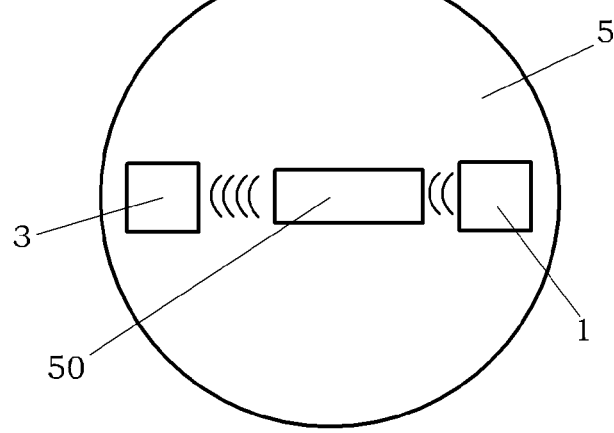
FIG. 17 is a schematic plan view illustrating another example of mutual arrangement of the sound wave generating unit, wave receiving element, and tubular body.
Figure 18:
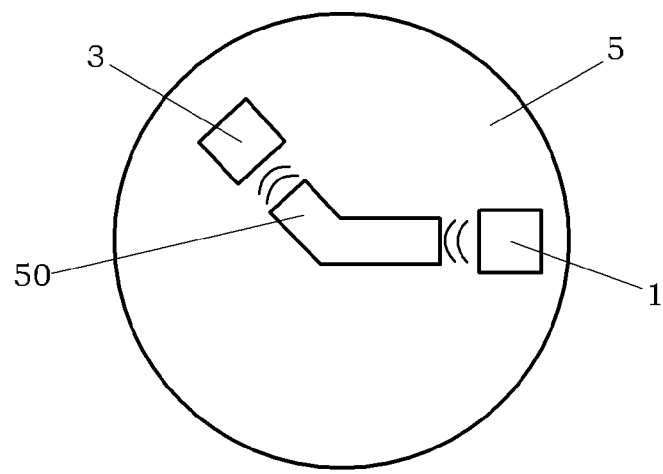
FIG. 18 is a schematic plan view illustrating another tubular body disposed between a sound wave generating unit and a wave receiving element.
Figure 19:
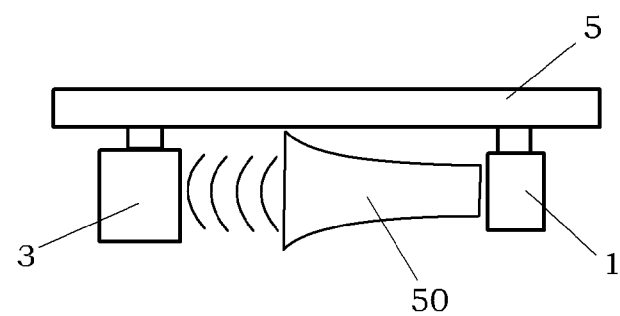
FIG. 19 is a schematic side view illustrating another tubular body disposed between a sound wave generating unit and a wave receiving element.

The tubular body 50 may have a configuration in which the sound wave generating unit 1 is covered with the tubular body 50, as shown in FIG. 16, or a configuration in which one end surface of the tubular body 50 is disposed opposite the sound wave generating unit 1 at a predetermined distance therefrom as shown in FIG. 17. Further, when the central axis of the sound wave generating unit 1 is not coaxial with the central axis of the wave receiving element 3, for example, when the wave receiving element 3 is disposed obliquely with respect to the central axis of the sound wave generating unit 1, the tubular body 50 that is curved along the propagation path may be disposed between the sound wave generating unit 1 and wave receiving element 3, as shown in FIG. 18. Furthermore, an acoustic horn in which a cross section perpendicular to the longitudinal direction increases in size along the propagation direction of ultrasound waves may be used as the tubular body 50, as shown in FIG. 19. The tubular body 50 is not limited to an angular tubular shape and may have a round shape.

With the fire sensor of the present embodiment, the effect obtained in addition to the effects identical to those described in the first embodiment is that the SN ratio can be increased because the decrease in sound pressure caused by diffusion of ultrasound waves can be inhibited by providing the tubular body 50. Further, it is especially preferred that the surface of the heat-generating body layer 13 of the sound wave generating unit 1 be formed to a size almost identical to that of the ultrasound wave inlet port of the tubular body 50 because such a configuration makes it possible to avoid the decrease in sound pressure caused by interference between ultrasound waves inside the tubular body 50.

Fourth Embodiment

Figure 20:
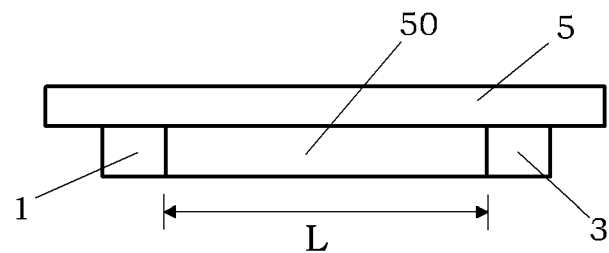
FIG. 20 is a schematic side view of a fire sensor of a fourth embodiment of the present invention.

The fire sensor of the present embodiment is substantially identical to that of the first embodiment, except that the tubular body 50 having a length equal to the distance between the sound wave generating unit 1 and wave receiving element 3 is disposed so that both ends of the tubular body 50 in the longitudinal direction are closed by the sound wave generating unit 1 and wave receiving element 3, as shown in FIG. 20. Therefore, structural elements identical to those of the first embodiment are assigned with identical reference numerals and redundant explanation thereof is omitted.

Figure 21:
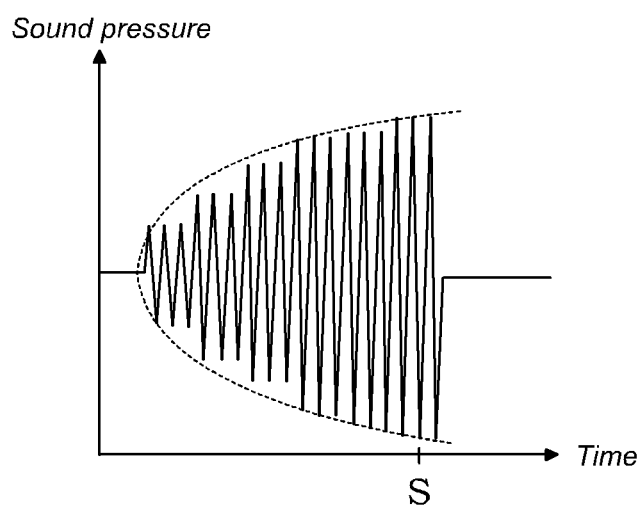
FIG. 21 is a graph illustrating the variation in sound pressure inside the tubular body with time.

The tubular body 50 disposed as shown in FIG. 20 has an inherent resonance frequency similarly to an acoustic tube closed at both ends. In other words, where the size of the tubular body 50 in the longitudinal direction is denoted by L, a frequency f corresponding to a wavelength $\lambda$ satisfying the relationship $L=(n/2)\times\lambda$ (here, n is a natural number) will be the resonance frequency of the tubular body 50 (this frequency is defined as $f=c/\lambda$, where c stands for a propagation velocity of the ultrasound wave). Therefore, where a continuous ultrasound wave satisfying the relationship $L=(n/2)\times\lambda$ is introduced in the tubular body 50 from an end surface in the longitudinal diction thereof, at least part of the ultrasound wave will be repeatedly reflected at both end surfaces in the longitudinal direction of the tubular body 50. As a result, the reflected waves and the direct waves from the sound wave generating unit 1 will be superimposed, causing resonance, and the sound pressure of the ultrasound wave will increase inside the tubular body 50 with the passage of time, as shown in FIG. 21.

Accordingly, in the present embodiment, a resonance is induced inside the tubular body 50 and the sound pressure of ultrasound wave from the sound wave generating unit 1 is increased by controlling the sound wave generating unit 1 with the control unit 2 so that an ultrasound wave with an inherent resonance frequency is provided into the tubular body 50. In this case, in order to induce the resonance inside the tubular body 50, it is necessary to provide a ultrasound wave with a plurality of periods (referred to hereinbelow as m periods) exceeding $L/\lambda$ from the sound wave generating unit 1, rather than a single-pulse ultrasound wave. Accordingly, the control unit 2 controls the sound wave generating unit 1 so as to provide a continuous ultrasound wave of m ($>L/\lambda$) periods to the tubular body 50. In other words, the sound wave generating unit 1 is controlled by the control unit 2 so that a transmission time $t_p$ (in other words, $t_p=m\times\lambda/c$) of an ultrasound wave that is continuously transmitted from the sound wave generating unit 1 becomes longer than a propagation time $t_s$ (in other words, $t_s=L/c$) required for the ultrasound wave to propagate between the two ends in the longitudinal direction of the tubular body 50 (in other words, so that $t_p>t_s$). The wave receiving element 3 detects the sound pressure of the ultrasound wave at a timing (timing "S" in FIG. 21) at which a resonance is generated inside the tubular body 50 and the sound pressure of the ultrasound wave is saturated. The sound pressure of the ultrasound wave is usually saturated when the transmission of the ultrasound wave from the sound wave generating unit 1 is completed. Therefore, the sound pressure of the ultrasound wave may be detected in the wave receiving element 3, for example, at the same time as the transmission of the ultrasound wave from the sound wave generating unit 1 is completed.

Figure 22:
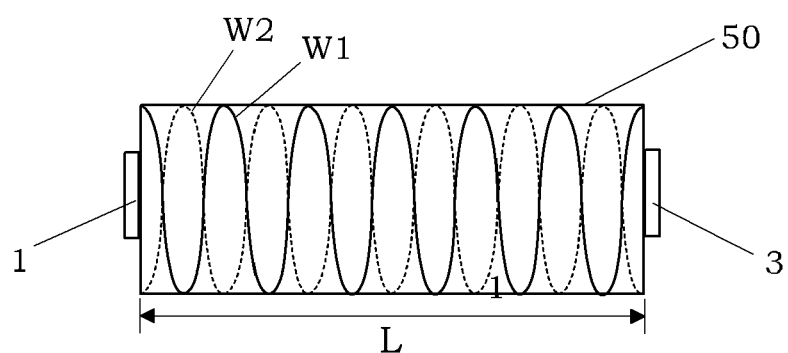
FIG. 22 is a schematic side view illustrating a sound wave generating unit and a wave receiving element disposed at both ends of the tubular body.
Figure 23:
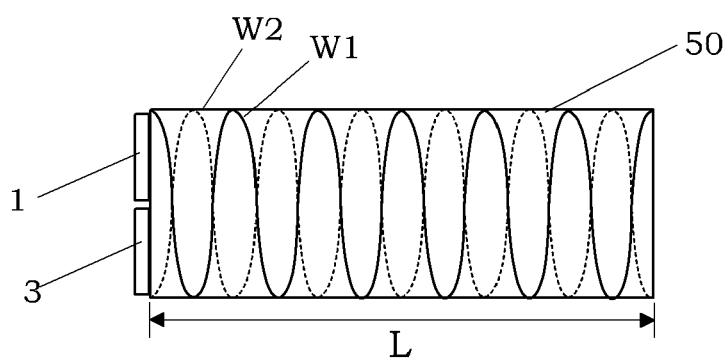
FIG. 23 is a schematic side view illustrating a sound wave generating unit and a wave receiving element disposed at one end of the tubular body.

In the present embodiment, as shown in FIG. 22, the sound wave generating unit 1 is disposed at one end surface of the tubular body 50, and the wave receiving element 3 is disposed at the other end surface. In an acoustic tube in which the two end surfaces are closed, the variation in pressure caused by the ultrasound wave reaches a maximum at both ends. Therefore, the wave receiving element 3 can detect the sound pressure of the ultrasound wave in a position in which the variation in pressure caused by the ultrasound wave is the largest. In other words, the wave receiving element 3 can detect the sound pressure of the ultrasound wave where a loop of sound pressure of the ultrasound wave (that is, a knot of air transfer speed) is located (in FIG. 22, the distance between the "W1" and "W2" in the longitudinal direction represents the amount of pressure variations). As a result, the variation amount of the output of the wave receiving element 3 related to the variation amount of smoke density can be greatly increased. Further, as shown in FIG. 23, even when the sound wave generating unit 1 and wave receiving element 3 are disposed side by side at one end surface of the tubular body 50 and the other end surface (right end surface in FIG. 23) in the longitudinal direction of the tubular body 50 is closed, the wave receiving element 3 can detect the sound pressure in a location where pressure variations caused by the ultrasound wave reach a maximum.

Figure 24:
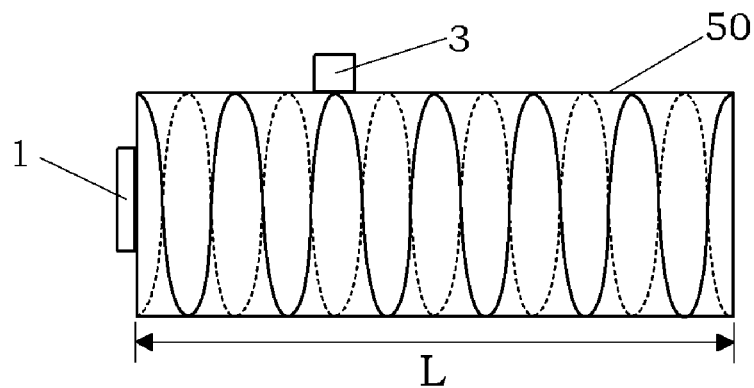
FIG. 24 is a schematic side view illustrating a sound wave generating unit disposed at one end of the tubular body and a wave receiving element disposed at the side surface of the tubular body.

Further, as shown in FIG. 24, it is also possible to dispose the sound wave generating unit 1 at one end surface of the tubular body 50 closed at both end surfaces and dispose the wave receiving element 3 in such a location on the side surface along the longitudinal direction in which pressure variations caused by the ultrasound wave from the sound wave generating unit 1 reach a maximum. A zone in which pressure variations caused by the ultrasound wave reach a maximum are not only at both ends in the longitudinal direction of the acoustic tube closed at both ends, but also at each $\lambda/2$ ($\lambda$ is a wavelength of ultrasound wave) from one end surface in the longitudinal direction. Where the wave receiving element 3 is disposed in such a location, the variation amount of the output of the wave receiving element 3 related to the variation amount of smoke density can be greatly increased.

Figure 25:
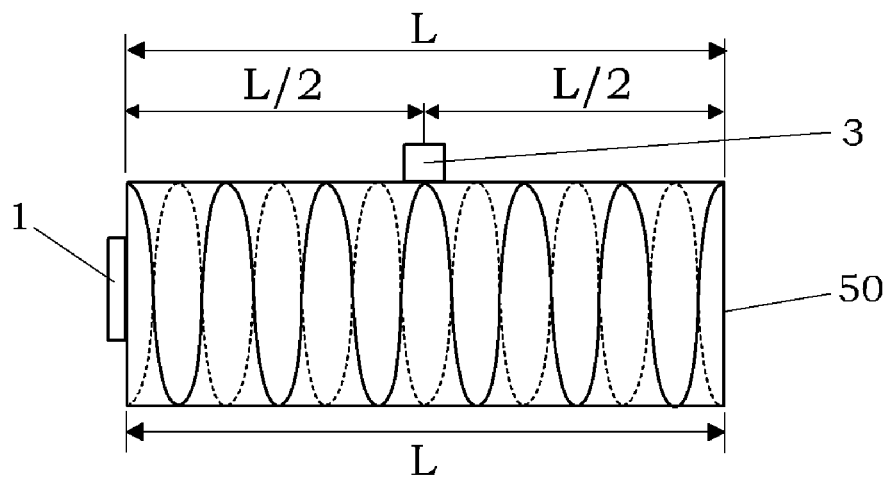
FIG. 25 is a schematic side view illustrating a sound wave generating unit disposed at one end of the tubular body and a wave receiving element disposed in the central portion of the side surface of the tubular body.

FIG. 25 illustrates another example in which the wave receiving element 3 is disposed in such a position at the side surface of the tubular body 50 in which pressure variations caused by the ultrasound wave from the sound wave generating unit 1 reach a maximum. More specifically, in this case, the wave receiving element 3 is disposed in the central portion in the longitudinal direction of the tubular body 50, under an assumption that the control unit 2 controls the sound wave generating unit 1 so that an ultrasound wave provided to the monitoring space has a wavelength $\lambda$ obtained by dividing the length L of the inner space of the tubular body 50 by a natural number n (that is, $\lambda=L/n$). Essentially, where an ultrasound wave with the wavelength $\lambda$ ($=L/n$) is provided from the sound wave generating unit 1, the central portion in the longitudinal direction of the tubular body 50 will necessarily be in a position at a distance from one end surface in the longitudinal direction that is equal the half wavelength $\lambda/2$ multiplied by n, and pressure variations caused by the ultrasound wave reach a maximum at all times. With such a configuration, where the above-described condition relating to the wavelength $\lambda$ ($=L/n$) is satisfied, even when the frequency of the ultrasound wave is different, the wave receiving element 3 disposed in the central portion in the longitudinal direction of the tubular body 50 can detect the sound pressure in a position in which pressure variations caused by the ultrasound wave reach a maximum, and the design of the tubular body 50 is simplified by comparison with the case in which the wave receiving element 3 is disposed in locations that differ correspondingly to the frequency of the ultrasound wave.

When an acoustic tube in which both end surfaces are closed is resonated, the resonance is caused by reflections of the ultrasound wave at the end surfaces in the longitudinal direction. In particular, where the ultrasound wave has a short wavelength, even very small concavities and concavities at the end surfaces can result in decreased sound pressure due to interference between the waves during reflection at the end surfaces. However, where the wave receiving element 3 is disposed at the side surface of the tubular body 50 as shown in FIG. 24, the end surface of the tubular body 50 can be made a flat surface with few concavities and convexities compared with a case in which the wave receiving element 3 is disposed at the end surface of the tubular body 50. As a result, the increase in sound pressure by resonance can be obtained without hindering the reflection of ultrasound waves at the end surface of the tubular body 50 with the wave receiving element 3. Further, in the configuration illustrated by FIGS. 22 to 25, because the inside of the tubular body 50 serves as a monitoring space, a hole (not shown in the figure) for guiding smoke and the like inside the tubular body is provided in the side surface along the longitudinal direction of the tubular body 50. From the standpoint of further facilitating the introduction of smoke, it is preferred that the hole be provided in the tubular body of another embodiment having a portion thereof opened. Further, the disposition of the hole is not limited to the side surface of the tubular body.

Because the sound velocity c, which is the propagation velocity of ultrasound wave, changes correspondingly to the absolute temperature of the medium, the resonance frequency of the tubular body 50 is not constant and fluctuates due to variations in sound velocity caused by variations in temperature of the medium. Therefore, in order to match accurately the frequency of the ultrasound wave from the sound wave generating unit 1 with the resonance frequency of the tubular body 50, it is necessary to correct the frequency of the ultrasound wave from the sound wave generating unit 1 correspondingly to the variations in sound velocity that follow the variations in temperature. In the present embodiment, the control unit 2 is provided with a frequency correction unit (not shown in the figure) that corrects the frequency of the ultrasound wave from the sound wave generating unit 1 correspondingly to variations in sound velocity that follow the variations in temperature. Therefore, although the resonance frequency of the tubular body 50 may fluctuate due to variations in sound velocity, because the frequency of the ultrasound wave from the sound wave generating unit is corrected by the frequency correction unit to the resonance frequency of the tubular body 50 after fluctuations, the resonance can be reliably induced inside the tubular body 50. Further, the frequency correction unit implements the frequency correction of the ultrasound wave from the sound wave generating unit 1 by using the sound velocity found based on the difference in time between the transmission of the ultrasound wave from the sound wave generating unit 1 and the reception thereof by the wave receiving element 3 in the sound velocity detection unit 43 explained in the first embodiment. As a result, the configuration of the smoke sensor can be simplified by comparison with that in the case in which separate means is provided for finding the sound velocity.

A specific example of the present embodiment will be described below. Where the sound velocity c is 340 m/sec, and the length L in the longitudinal direction of the tubular body 50 is 34 mm, the frequency f (=c/λ) of the ultrasound wave transmitted by the sound wave generating unit 1 may be set, for example, to 100 kHz (n=20) or 50 kHz (n=10) in order to satisfy the relationship L=(n/2)×λ. Thus, the frequency of 100 kHz or 50 kHz is a resonance frequency of the tubular body 50, and where an ultrasound wave of such frequency is generated from the sound wave generating unit 1, the sound pressure of the ultrasound wave is increased by the resonance correspondingly to the time elapsed, as shown in FIG. 21. In this case, as described hereinabove, it is necessary to provide a continuous ultrasound wave of m periods (>L/λ) to the monitoring space. Therefore, the control unit 2 controls the sound wave generating unit 1 so that an ultrasound wave of about 100 periods in the case of 100 kHz and about 50 periods in the case of 50 kHz is continuously provided from the wave generating unit 1. With such a configuration, the sound pressure of the ultrasound wave detected by the wave receiving element 3 at a timing (timing "S" in FIG. 21) at which a resonance is generated inside the tubular body 50 and the sound pressure of the ultrasound wave is saturated becomes several tens of times that in the configuration in which no tubular body 50 is present and a single-pulse ultrasound wave is transmitted and received.

As a modification example of the present embodiment, a configuration may be employed in which only one end surface in the longitudinal direction of the tubular body 50 is closed (other end surface is opened). In this case, the tubular body 50 also has an inherent resonance frequency similarly to the acoustic tube closed at one end. In other words, a frequency f (=c/λ) corresponding to the wavelength λ satisfying the relationship L=(¼+n/2)×λ (where n=0, 1, 2, 3, . . . ), where L stands for the size of the tubular body 50 in the longitudinal direction, becomes the resonance frequency of the tubular body 50. Therefore, where a continuous ultrasound wave satisfying the relationship L=(¼+n/2)×λ is introduced in the tubular body 50 from an end surface in the longitudinal direction, at least part of the ultrasound wave is repeatedly reflected by both end surfaces in the longitudinal direction of the tubular body 50. As a result, the reflected waves and the direct wave from the wave generating unit 1 are superimposed, causing resonance, and the sound pressure increases inside the tubular body 50 with the passage of time, as shown in FIG. 21. In this case, in order to generate a resonance inside the tubular body 50, the control unit 2 controls the sound wave generating unit 1 so as to transmit a continuous ultrasound wave of m (>L/λ) periods, rather than a single-pulse ultrasound wave. In other words, the sound wave generating unit 1 is controlled by the control unit 2 so that a transmission time $t_p$ (=m×λ/c) in which an ultrasound wave is continuously transmitted from the sound wave generating unit 1 becomes longer than a propagation time $t_s$ (=L/c) required for the ultrasound wave to propagate between the two ends in the longitudinal direction of the tubular body 50 (in other words, $t_p > t_s$). When one end surface of the tubular body 50 is an open end, a loop of sound pressure of the ultrasound wave (that is, a knot of air transfer speed) appears at a very small distance ΔL from the open end on the outside thereof. Therefore, where the length L used for finding the resonance frequency is corrected by ΔL (open end correction), a more accurate resonance frequency can be found.

With the above-described fire sensor of the present embodiment, the decrease in sound pressure between the wave generating unit 1 and wave receiving element 3 can be further inhibited by generating a resonance inside the tubular body 50, and the variation amount of the output of the wave receiving element 3 related to the variation amount of smoke density can be increased, thereby raising the SN ratio. Moreover, because an effective propagation path extends correspondingly to the number of reflections in an ultrasound wave that is repeatedly reflected by the end surfaces in the longitudinal direction of the tubular body 50 due to the resonance, this extension of the propagation path also contributes to the increase in the variation amount of the output of the wave receiving element 3 related to the variation amount of smoke density, and the attenuation amount of ultrasound wave becomes several times that in the configuration in which a non-resonant single-pulse ultrasound wave is received by the wave receiving element 3.

Fifth Embodiment

Figure 26:
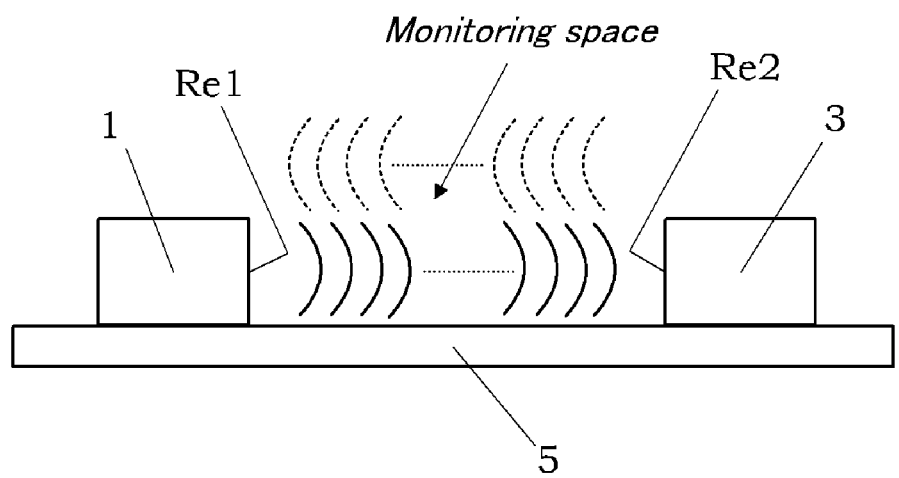
FIG. 26 is a schematic side view illustrating a fire sensor of a fifth embodiment of the present invention.

The fire sensor of the present embodiment is substantially identical to that of the first embodiment, except that the opposing surfaces of the wave generating unit 1 and wave receiving element 3 form respective first reflective surface Re1 and second reflective surface Re2, as shown in FIG. 26. Therefore, structural elements identical to those of the first embodiment are assigned with identical reference numerals and redundant explanation thereof is omitted.

In the present embodiment, the propagation path of an ultrasound wave between the wave generating unit 1 and wave receiving element 3 has an inherent resonance frequency, similarly to an air column having the first and second reflective surfaces Re1, Re2 at both ends. In other words, where the distance between the wave generating unit 1 and wave receiving element 3 is denoted by L, a frequency f corresponding to a wavelength λ satisfying the relationship L=(n/2)×λ (here, n is a natural number) will be the resonance frequency in the ultrasound wave propagation path between the wave generating unit 1 and wave receiving element 3 (this frequency is defined as f=c/λ, where c stands for a propagation velocity of the ultrasound wave). Therefore, where a continuous ultrasound wave satisfying the relationship L=(n/2)×λ is transmitted from the wave generating unit 1, at least part of the ultrasound wave will be reflected by the second reflective surface Re2 and will become a reflected wave (shown by a broken line in FIG. 26). This reflected wave is further reflected by the first reflective surface Re1, thereby producing a reflected wave, and these reflected waves are superimposed with the same phase on the subsequent ultrasound wave transmitted from the wave generating unit 1, thereby causing resonance. As a result, the sound pressure of ultrasound waves increases with the passage of time.

Therefore, the control unit 2 controls the sound wave generating unit 1 so that an ultrasound wave of a resonance frequency inherent to the propagation path of the ultrasound wave that is based on the distance L is provided to the monitoring space, whereby a resonance can be induced in the propagation path of the ultrasound wave between the wave generating unit 1 and wave receiving element 3 and the sound pressure of ultrasound wave can be increased. Further, similarly to the fourth embodiment, the sound wave generating unit 1 is controlled by the control unit 2 so that a transmission time $t_p$ at which an ultrasound wave is continuously transmitted from the ultrasound wave 1 becomes longer than a propagation time $t_s$ required for the ultrasound wave to propagate between the wave generating unit 1 and wave receiving element 3. As a result, the ultrasound wave from the wave generating unit 1 is superimposed at least on the reflected wave from the second reflective surface Re2, causing resonance. Therefore, the decrease in sound pressure of the ultrasound wave between the wave generating unit 1 and wave receiving element 3 can be inhibited. The wave receiving element 3 detects the sound pressure of ultrasound wave at a timing at which a resonance occurs between the wave generating unit 1 and wave receiving element 3 and the sound pressure is saturated.

Further, similarly to the fourth embodiment, a frequency correction unit (not shown in the figure) that corrects the frequency of ultrasound wave from the wave generating unit 1 in response to sound velocity variations that follow temperature variations is provided in the control unit 2. Therefore, a resonance can be reliably induced between the wave generating unit 1 and wave receiving element 3.

A specific example of the present embodiment will be described below. Where the sound velocity c is 340 m/sec, and the distance L between the sound wave generating unit 1 and wave receiving element 3 is 34 mm, the frequency f ($=c/\lambda$) of the ultrasound wave transmitted by the sound wave generating unit 1 may be set, for example, to 105 kHz (n=21) in order to satisfy the relationship $L=(n/2)\times\lambda$. Thus, the frequency of 105 kHz is a resonance frequency of the propagation path, and where an ultrasound wave of such frequency is provided from the sound wave generating unit 1, the sound pressure of the ultrasound wave is increased by the resonance. In this case, it is necessary to generate a continuous ultrasound wave of m periods ($>L/\lambda$) to the monitoring space. Therefore, the control unit 2 controls the sound wave generating unit 1 so that an ultrasound wave of at least about 11 periods in the case of an ultrasound wave of 105 kHz is continuously provided to the monitoring space. Where an ultrasound wave of 105 kHz is transmitted continuously over 105 periods from the wave generating unit 1, while the ultrasound wave reciprocates five times between the two reflective surfaces Re1, Re2, the reflected waves or the reflected waves and the direct wave from the sound wave generating unit 1 are superimposed, thereby increasing the sound pressure. With such a configuration, the sound pressure of the ultrasound wave detected by the wave receiving element 3 at a timing at which a resonance is generated and the sound pressure of the ultrasound wave is saturated becomes several tens of times that in the configuration in which a single-pulse ultrasound wave of a frequency other than the resonance frequency is transmitted and received.

With the fire sensor of the present embodiment, in addition to the effects identical to those attained in the first embodiment, the decrease in sound pressure during ultrasound wave propagation in the monitoring space can be inhibited by inducing a resonance in the propagation path of the ultrasound wave between the sound wave generating unit 1 and wave receiving element 3 and, therefore, the SN ratio can be increased. Moreover, an effective propagation path extends correspondingly to the number of reflections in an ultrasound wave that is reflected by the reflective surfaces Re1, Re2 due to the resonance and the ultrasound wave substantially reaches the wave receiving element 3 via the propagation path that is several time longer than the distance L between the sound wave generating unit 1 and wave receiving element 3. This result also contributes to the increase in the variation amount of the output of the wave receiving element 3 related to the variation amount of smoke density, and the attenuation amount of ultrasound wave becomes several times that in the configuration in which a non-resonant single-pulse ultrasound wave is received by the wave receiving element 3.

Sixth Embodiment

Figure 27:
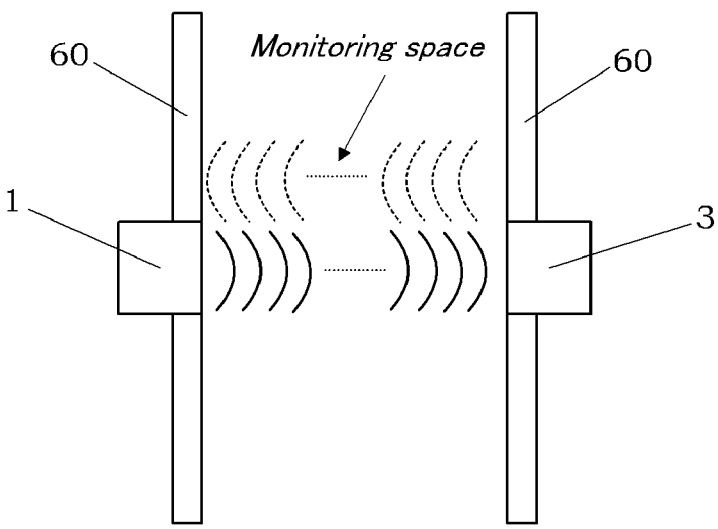
FIG. 27 is a schematic side view illustrating a fire sensor of a sixth embodiment of the present invention.

The fire sensor of the present embodiment is substantially identical to that of the fifth embodiment, except that reflective plates 60 increasing the reflectance of ultrasound waves are provided on opposing surfaces of the sound wave generating unit 1 and wave receiving element 3, as shown in FIG. 27. Therefore, structural elements identical to those of the fifth embodiment and embodiments cited by the fifth embodiment are assigned with identical reference numerals and redundant explanation thereof is omitted.

Thus in the present embodiment a pair of plate-shaped reflective plates 60 are disposed opposite each other, and the sound wave generating unit 1 and wave receiving element 3 are installed in almost central portions of respective reflective plates 60. The surface of the sound wave generating unit 1 that faces the wave receiving element 3 and the surface of the wave receiving element 3 that faces the sound wave generating unit 1 are flush with the surfaces of the reflective plates 60. With such a configuration, although the ultrasound wave expands due to diffusion in the propagation path between the sound wave generating unit 1 and wave receiving element 3, because the ultrasound wave is returned to the propagation path by reflection at the reflective plate 60 surrounding the wave receiving element 3 or sound wave generating unit 1, the decrease in sound pressure caused by diffusion of ultrasound wave can be inhibited, the variation amount of the output of the wave receiving element related to the variation amount of smoke density can be increased, and the SN ratio rises.

Figure 28:
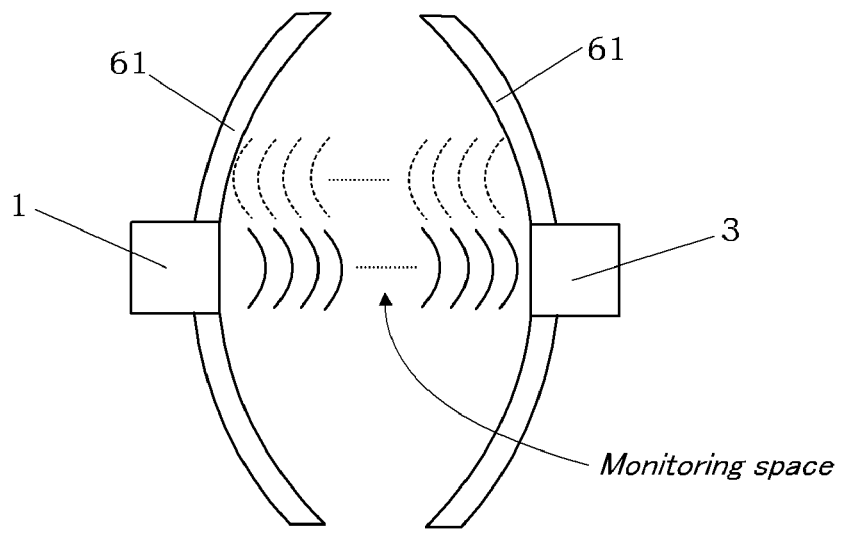
FIG. 28 is a schematic side view illustrating a fire sensor of the first modification example of the sixth embodiment.

As a first modification example of the present embodiment, a reflective plate 61 curved in a parabolic shape may be used, as shown in FIG. 28. Because the reflective plate 61 has a convex curved surface as a reflective surface, the ultrasound wave is converged on the wave receiving element 3 when the ultrasound wave is reflected by each reflective plate and the decrease in sound pressure caused by diffusion of the ultrasound wave can be further inhibited. The reflective plate 61 having a convex curved surface as an effective surface may be disposed only on either of the sound wave generating unit 1 and wave receiving element 3.

Figure 29:
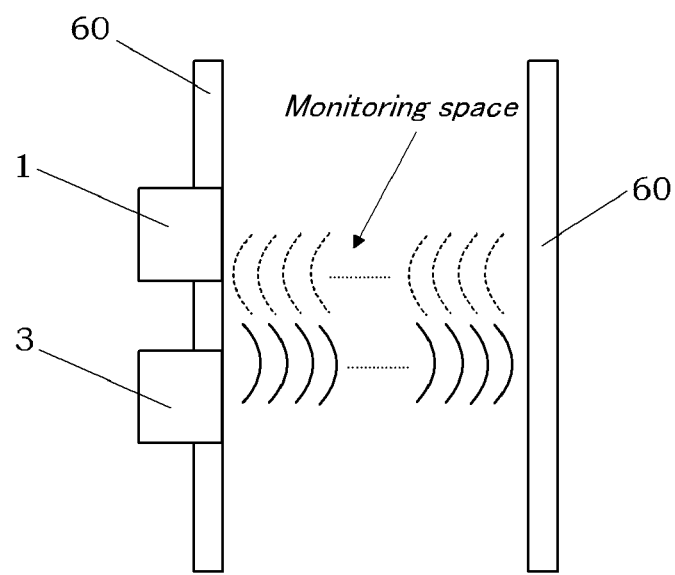
FIG. 29 is a schematic side view illustrating a fire sensor of the second modification example of the sixth embodiment.
Figure 30:
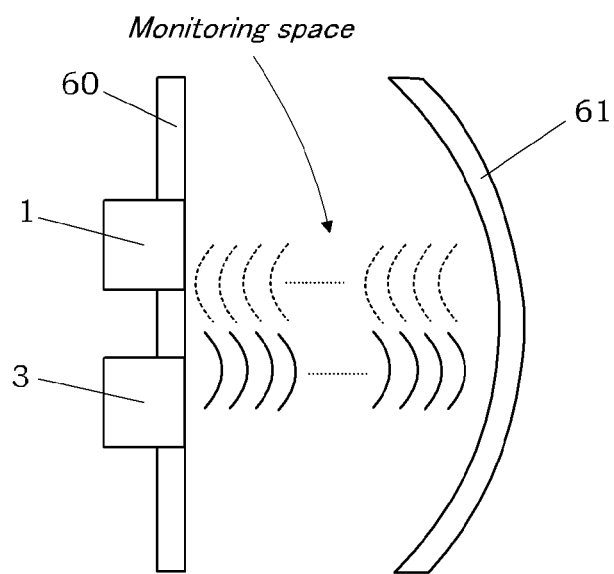
FIG. 30 is a schematic side view illustrating a fire sensor of the third modification example of the sixth embodiment.

As a second modification example of the present embodiment, the sound wave generating unit 1 and wave receiving element 3 may be disposed side by side on one of a pair of plate-shaped reflective plates 60 as shown in FIG. 29. In this case, the decrease in the number of elements results in cost reduction. Furthermore, in such a configuration, the ultrasound wave from the sound wave generating unit 1 is reflected at least once by the reflective plate 60 disposed opposite thereto, rather than reaches the wave receiving element 3 as a direct wave. Therefore, a resonance is easily induced between the sound wave generating unit 1 and wave receiving element 3. Alternatively, as shown in FIG. 30, a parabolic reflective plate 61 may be disposed instead of the plate-shaped reflective plate 60 disposed opposite the sound wave generating unit 1 and wave receiving element 3. In this case, the sound converging function is improved and the decrease in sound pressure caused by diffusion of the ultrasound wave can be further inhibited.

In the configuration shown in FIG. 29 or 30, the distance between the reflective plates is L/2, where L stands for the distance between the sound wave generating unit 1 and wave receiving element 3, and a frequency f corresponding to a wavelength $\lambda$ satisfying the relationship $L/2=(n/2)\times\lambda$ (here, n is a natural number) will be the resonance frequency in the propagation path of ultrasound wave between the sound wave generating unit 1 and wave receiving element 3.

Seventh Embodiment

Figure 31:
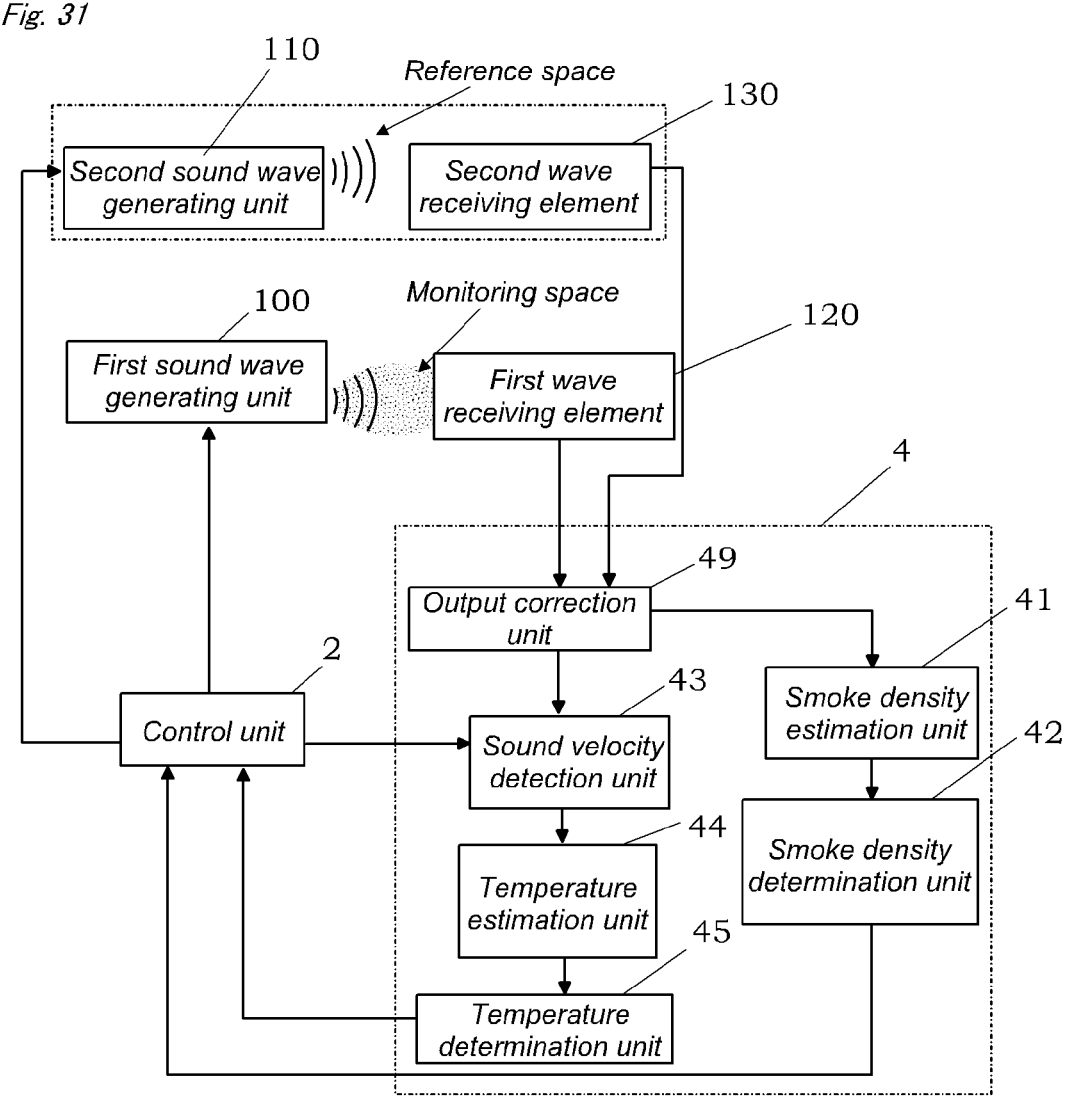
FIG. 31 is a schematic side view illustrating a fire sensor of a seventh embodiment of the present invention.

The fire sensor of the present embodiment is substantially identical to the fire sensor of the first embodiment, except that the sound wave generating unit that generates ultrasound waves is configured by a first sound wave generating unit 100 and a second sound wave generating unit 110, the sound wave receiving unit that receives the ultrasound waves is configured by a first wave receiving element 120 and a second wave receiving element 130, and the signal processing unit 4 includes the below-described output correction unit 49, as shown in FIG. 31. Therefore, identical structural elements are assigned with identical reference numerals and redundant explanation thereof is omitted.

Figure 32:
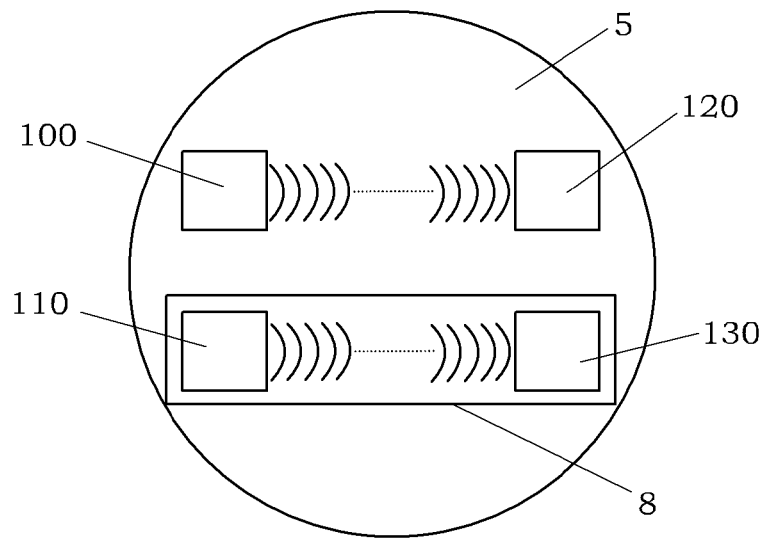
FIG. 32 is a schematic plan view of a fire sensor of the seventh embodiment.

In the present embodiment, as shown in FIG. 32, the first sound wave generating unit 100 and first wave receiving element 120 are disposed opposite each other via a monitoring space on the surface of a circuit board 5 configured by a disk-shaped printed board, and the second sound wave generating unit 110 and second wave receiving element 130 are disposed opposite each other via a reference space. The control unit 2 and signal processing unit 4 are provided on the circuit board 5.

The monitoring space located between the first sound wave generating unit 100 and first wave receiving element 120 communicates with the outer space (outer air) around the fire sensor in order to monitor the presence or absence of fire, whereas the reference space located between the second sound wave generating unit 110 and second wave receiving element 130 is enclosed by a shielding wall 8 that shields floating particles including at least smoke particles. In other words, the first sound wave generating unit 100 transmits an ultrasound wave to the monitoring space, and the second sound wave generating unit 110 transmits an ultrasound wave to the reference space.

An ultrasound wave generating element identical to that of the first embodiment can be used in each of the first sound wave generating unit 100 and second sound wave generating unit 110, and a microphone of an electrostatic capacity type that is identical to that of the first embodiment can be employed in each of the first wave receiving element 120 and second wave receiving element 130. On the other hand, the control unit 2 that controls the first sound wave generating unit 100 and second sound wave generating unit 110 is configured by a drive circuit that supplies a drive input waveform to drive the first sound wave generating unit 100 and second sound wave generating unit 110 and a control circuit configured by a microcomputer that controls the drive circuit.

A specific feature of the signal processing unit 4 is that it is provided with an output correction unit 49 for correcting the output of the first wave receiving element 120, in addition to the smoke density estimation unit 41, smoke density determination unit 42, sound velocity detection unit 43, temperature estimation unit 44, and temperature estimation unit 45.

Thus, the smoke density estimation unit 41 estimates smoke density on the basis of the attenuation amount from the standard value of the output of the first wave receiving element 120 that detects the sound pressure of ultrasound wave from the first sound wave generating unit 100. The smoke density determination unit 42 determines that there is "No Fire" when the smoke density estimated by the smoke density estimation unit 41 is less than a threshold. When the estimated smoke density is equal to or higher than the threshold, the smoke density determination unit 42 determines that "Fire is Present" and outputs a fire sensing signal to the control unit 2. When receiving the fire sensing signal, the control unit 2 generates an alarm sound composed of an audible sound wave from the first sound wave generating unit 100. The sound velocity detection unit 43 finds the sound velocity on the basis of the difference in time between the transmission of the ultrasound wave from the first sound wave generating unit 100 and the reception thereof by the first wave receiving element 120. The temperature estimation unit 44 estimates the temperature of the monitoring space on the basis of the sound velocity found by the sound velocity detection unit 43. The temperature determination unit 45 determines the presence of fire by comparing the temperature estimated by the temperature estimation unit 44 with a stipulated temperature and, similarly to the smoke density estimation unit 41, determines that "Fire is Present" and outputs a fire sensing signal to the control unit 2 when the determined temperature is equal to or higher than a predetermined threshold.

The signal processing unit 4 is configured by a microcomputer, and various components (40 to 45, 49) constituting the signal processing unit 4 are realized by installing appropriate programs on the microcomputer.

The output correction unit 49, which is a specific unit of the present embodiment, will be described below in greater detail. The output of the first wave receiving element 120 can fluctuate depending not only on the decrease or increase in smoke density in the monitoring space, but also on variations in the ambient environment in which the fire sensor is located (for example, variations in temperature, humidity, and atmospheric pressure), variations in sound pressure of the ultrasound wave from the first sound wave generating unit 100 caused by changes in the first sound wave generating unit 100 or first wave receiving element 120 with time (for example, deterioration with time), and also changes in sensitivity of the first wave receiving element 120. In the present embodiment, the output correction unit 49 corrects the output of the first wave receiving element 120 on the basis of the variation ratio from the initial value of output (reference value) of the second wave receiving element 130, eliminates the effect of the above-described output fluctuations, and sends the corrected output of the first wave receiving element 120 to the sound velocity detection unit 43 and smoke density estimation unit 41.

More specifically, the output correction unit 49 receives the output of the second wave receiving element 130 that detects the sound pressure of ultrasound wave generated from the second sound wave generating unit 110 in the reference space, finds a correction coefficient based on a variation ratio from the initial value of the output of the second wave receiving element 130 that has been determined in advance, and outputs the output of the first wave receiving element 120 that has been corrected by using the correction coefficient to the smoke density estimation unit 41. Here, the initial value of the output of the second wave receiving element 130 is the output value of the second wave receiving element 130 detected, for example, when the ambient environment (for example, variations in temperature, humidity, and atmospheric pressure) is set to a predetermined state and does not change with time (for example, prior to shipping) and this output is stored in advance in the output correction unit 49. Alternatively, the same initial value may be set by a program at the design stage of the fire sensor. The present embodiment is so configured that the second sound wave generating unit 110 is driven, the output of the second wave receiving element 130 is measured, and the correction coefficient is calculated each time before the first sound wave generating unit 100 is driven and the smoke density in the monitoring space is detected. Therefore, the correction coefficient is updated each time the smoke density in the monitoring space is detected.

As an example, in the present embodiment, the first sound wave generating unit 100 and second sound wave generating unit 110 are driven under the same conditions (for example, sound pressure and frequency of the generated ultrasound wave), the first wave receiving element 120 and second wave receiving element 130 are used under the same conditions (for example, a DC bias voltage), and the mutual arrangement of the first sound wave generating unit 100 and first wave receiving element 120 is set identically to that of the second sound wave generating unit 110 and second wave receiving element 130, thereby making the output of the first wave receiving element 120 substantially equal to that of the second wave receiving element 130 when floating particles do not penetrate in the monitoring space and the monitoring space and reference space are in the same state (for example, temperature, humidity, and atmospheric pressure). In this case, the initial value of the output of the second wave receiving element 130 is substantially equal to the standard value of the output of the first wave receiving element 120. Although the first sound wave generating unit 100 and second sound wave generating unit 110 are not required to be driven simultaneously, the control unit 2 controls them so that the cumulative total of the ultrasound wave generation time in the first sound wave generating unit 100 and second sound wave generating unit 110 is the same.

Because the reference space is enclosed by the shielding wall 8, although the outer space (outer air) and monitoring space are identical in terms of temperature, no smoke particles or steam penetrate therein and the attenuation of ultrasound waves caused by the presence of smoke particles or steam is prevented. Further, a filter (for example, a porous ceramic filter) having formed therein a large number of fine holes (not shown in the figure) of a size that prevents the passage of floating particles is provided in the shielding wall 8, and the reference space and outer space communicate via the fine holes. Therefore, the conditions in the reference space are identical to those of the outer space and monitoring space not only in terms of temperature, but also in terms of humidity and atmospheric pressure.

As a result, the variation ratio of the actual output of the second wave receiving element 130 from the aforementioned initial value is determined correspondingly to variations in ambient conditions (for example, temperature, humidity, and atmospheric pressure) or variations in the second sound wave generating unit 110 or second wave receiving element 130 with time (identical to variations in the first sound wave generating unit 100 or first wave receiving element 120 with time). Because the output of the first wave receiving element 120 is corrected using a correction coefficient based on this variation ratio, an output of the first wave receiving element 120 is obtained from which the effect of variations in ambient environment or variations with time is excluded, and subsequent fire determination is implemented by the smoke density determination unit 42 and temperature determination unit 45 by using this output. Thus, accurate fire determination can be carried out based on information reflecting only smoke density in the monitoring space, upon removal of disturbance factors.

Figure 33:
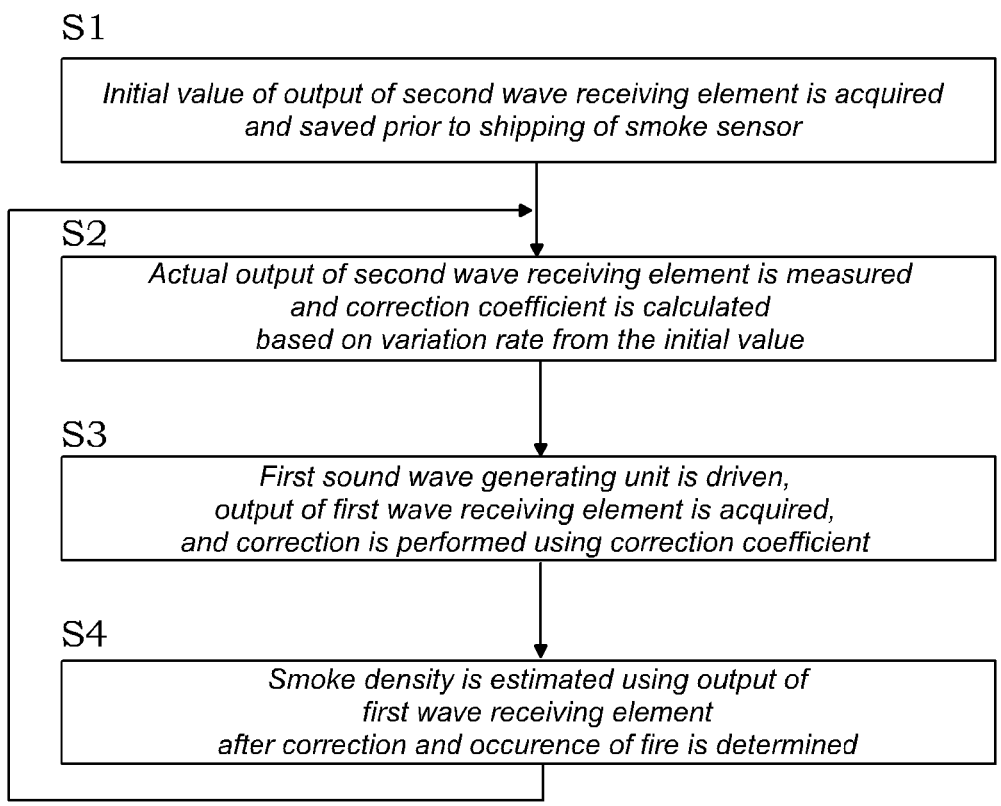
FIG. 33 is a flowchart illustrating an operation example of the fire sensor of the seventh embodiment.

An operation example of the fire sensor of the present embodiment will be specifically described below with reference to the flowchart shown in FIG. 33. First, the second sound wave generating unit 110 is driven before the fire sensor is shipped, the initial value of the output of the second wave receiving element 130 is acquired, and this initial value is stored in the output correction unit 49 (step S1). Then, after the fire sensor has been installed in the desired location and before the first sound wave generating unit 100 is driven, the second sound wave generating unit 110 is driven and the actual output of the second wave receiving element 130 is obtained. A correction coefficient is then calculated based on a variation ratio of the actual output of the second wave receiving element 130 from the initial value (step S2). Then, the first sound wave generating unit 100 is driven, an output from the first wave receiving element 120 is acquired, and this output is corrected using the correction coefficient in the output correction unit 49, whereby the effect of variations in ambient environment and variations with time is removed from the output of the first wave receiving element 120 (step S3). The smoke density in the monitoring space is then estimated by the smoke density estimation unit 41 by using the corrected output of the first wave receiving element 120 and the presence or absence of fire is determined by the smoke density determination unit 42 (step S4). Once step S4 has been completed, the processing flow returns to step S2 in which the correction coefficient is calculated and the operation of the above-described steps S2 to S4 is periodically repeated.

Figure 34:
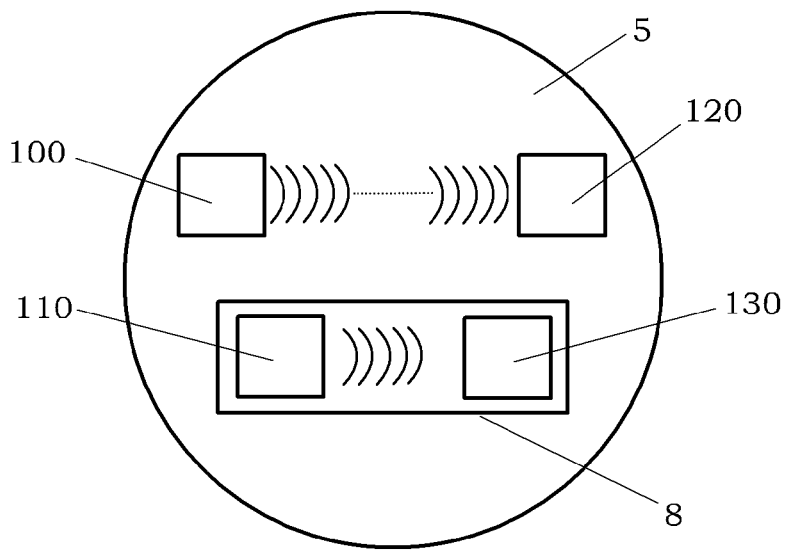
FIG. 34 is a schematic plan view of a fire sensor of a modification example of the seventh embodiment.

As a modification example of the present embodiment, the first sound wave generating unit 100 and second sound wave generating unit 110 and the first wave receiving element 120 and second wave receiving element 130 may be formed to have different configurations, the first sound wave generating unit 100 and second sound wave generating unit 110 may be driven under different conditions, and the first wave receiving element 120 and second wave receiving element 130 may be used under different conditions. Furthermore, as shown in FIG. 34, the mutual arrangement of the first sound wave generating unit 100 and first wave receiving element 120 may be different from that of the second sound wave generating unit 110 and second wave receiving element 130. In the case illustrated by FIG. 34, the distance between the first sound wave generating unit 100 and first wave receiving element 120 is set larger than that between the second sound wave generating unit 110 and second wave receiving element 130

Furthermore, a configuration may be employed in which the calculation of correction coefficient is performed once for a plurality of times the smoke density in the monitoring space is detected. For example, in an environment with small fluctuations of correction coefficient, the correction coefficient can be calculated (that is, updated) less frequently, thereby reducing power consumption.

With the fire sensor of the present embodiment, in addition to the effects identical to those described in the first embodiment, the occurrence rate of false alarm can be reduced and reliability of fire sensor operation can be further improved by performing fire determination after canceling the effect of output fluctuations of the first wave receiving element 120 with the output correction unit 49.

Eighth Embodiment

Figure 35:
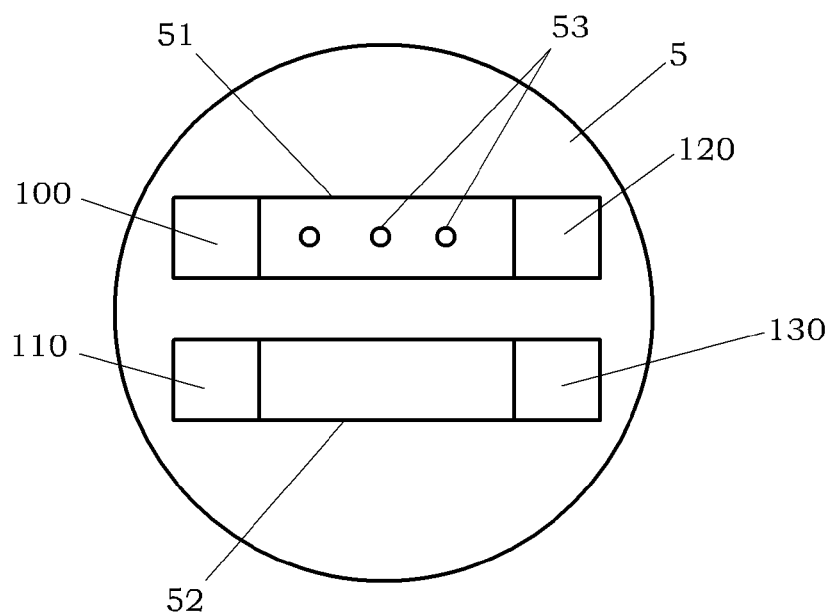
FIG. 35 is a schematic plan view of a fire sensor of a eighth embodiment of the present invention.

The fire sensor of the present embodiment is substantially identical to that of the seventh embodiment, except that a tubular body 51 is disposed between the first sound wave generating unit 100 and first wave receiving element 120 and a tubular body 52 is disposed between the second sound wave generating unit 110 and second wave receiving element 130, as shown in FIG. 35. Therefore, structural elements identical to those of the seventh embodiment and embodiments cited by the seventh embodiment are assigned with identical reference numerals and redundant explanation thereof is omitted.

Each of the tubular bodies 51, 52 is a linear angular tube, as shown in FIG. 35, and one end surface thereof in the longitudinal direction is closed by the first sound wave generating unit 100 and second sound wave generating unit 110, respectively. The other end surface is closed by the first wave receiving element 120 and second wave receiving element 130, respectively. Therefore, the inside of the tubular body 51 is a monitoring space and the inside of the tubular body 52 is equivalent to a reference space. A plurality of holes 53 having a size enabling the passage of floating particles including smoke particles are provided in the tubular body 51, and the monitoring space and an outer space communicate via the holes 53. On the other hand, the tubular body 52 also serves as a shielding wall 8 and has at least in part thereof a filter (for example, a porous ceramic filter) having formed therein a large number of fine holes (not shown in the figure) of a size such that floating particles cannot penetrate therethrough. Because ultrasound waves from the first sound wave generating unit 100 and second sound wave generating unit 110 thus pass inside the tubular bodies 51, 52, the decrease in sound pressure of ultrasound waves caused by diffusion can be prevented.

Where the length and opening shape of the tubular bodies 51, 52 are identical, when the monitoring space and reference space are under the same atmosphere (for example, temperature, humidity, and atmospheric pressure), the output of the first wave receiving element 120 matches that of the second wave receiving element 130 with a high degree of accuracy. As a result, the accuracy attained in correcting the output of the first wave receiving element 120 in the output correction unit 49 is further increased.

For example, let us assume that variations in ambient environment or variations with time in the first wave receiving element 120 and second wave receiving element 130 caused the decrease in sensitivity in an amount of Msens ($0 \leq Msens \leq 1$). In this case, the correction coefficient (1−Msens) can be calculated from a formula Pref=(1−Msens)×Pref0, and if Pmes' is calculated from Pmes'=Pmes×(1/(1−Msens)), the attenuation amount ΔPmes can be found from Pmes0−Pmes', where Pref stands for an output of the second wave receiving element 130, Pref0−an initial value of the output (reference value) of the second wave receiving element 130, Pmes−an output of the first wave receiving element 120, Pmes0−a standard value of the output of the first wave receiving element 120, Pmes' stands for Pmes after correction in the output correction unit 49, and ΔPmes−an attenuation amount of Pmes' from Pmes0.

Figure 36:
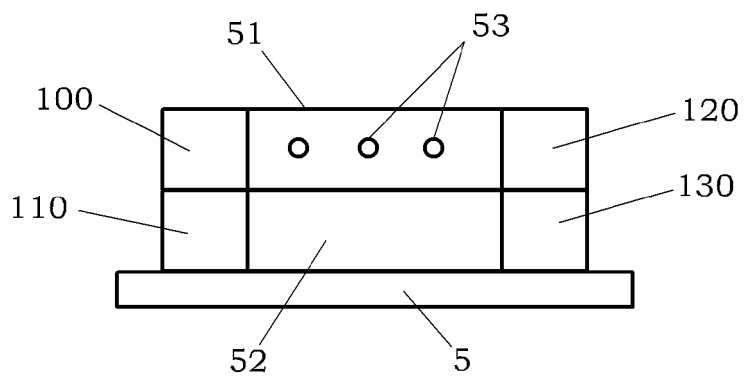
FIG. 36 is a schematic plan view of a fire sensor of a modification example of the eighth embodiment.

As a modification example of the present embodiment, tubular members 51, 52 may be disposed one on top the other on the surface of the circuit substrate 5, as shown in FIG. 36. Further, the tubular body 51 may be disposed only between the first sound wave generating unit 100 and first wave receiving element 120 as shown in FIG. 37. In the configuration illustrated by FIG. 37, the tubular body 51 is formed shorter than the distance between the first sound wave generating unit 100 and the first wave receiving element 120, and each end surface in the longitudinal direction is disposed at a respective distance from the first sound wave generating unit 100 and first wave receiving element 120, thereby opening both end surfaces in the longitudinal direction. In this case, the diffusion of ultrasound wave from the first sound wave generating unit 100 is also inhibited because the wave passes inside the tubular body 51. Therefore, the decrease in sound pressure of the ultrasound wave caused by diffusion can be inhibited. Because the monitoring space is located between the first sound wave generating unit 100 or the first wave receiving element 120 and the tubular body 51, the holes 53 may be eliminated.

With the fire sensor of the present embodiment, the effect obtained in addition to the effects described in the seventh embodiment is that the variation amount of the output of the first wave receiving element 120 related to the variation amount of smoke density becomes comparatively high and, therefore, the SN ratio increases because the decrease in sound pressure of the ultrasound wave between the first sound wave generating unit 100 and the first wave receiving element 120 that is caused by diffusion can be inhibited by disposing the tubular body 51.

Ninth Embodiment

The fire sensor of the present embodiment is substantially identical to that of the seventh embodiment, except that the monitoring space and reference space are formed by dividing the inner space of the tubular body 50 in two, upper and lower, spaces by a partition wall 54 and forming the first sound wave generating unit 100 and second sound wave generating unit 110 by a single ultrasound wave generating element 140, as shown in FIGS. 38A and 38B. Therefore, structural elements identical to those of the seventh embodiment and embodiments cited by the seventh embodiment are assigned with identical reference numerals and redundant explanation thereof is omitted.

In the tubular body 50 of the present embodiment, holes 53 through which the monitoring space communicates with the outer space and which have a size enabling the passage of floating particles including smoke particles are provided in the monitoring space side, and the first wave receiving element 120 and second wave receiving element 130 are disposed at one end of the monitoring space and reference space, respectively. A portion of the tubular body 50 that forms the reference space also serves as a shielding wall 8, and a filter (for example, a porous ceramic filter) having formed therein a large number of fine holes (not shown in the figure) of a size that prevents the passage of floating particles is provided in at least part of the shielding wall 8. The first sound wave generating unit 100 and second sound wave generating unit 110 are provided in the form of a single ultrasound wave generating element 140 that is disposed over the monitoring space and outer space at the other end thereof. In FIG. 38B, the first wave receiving element 120 and second wave receiving element 130 are omitted.

The features of the present embodiment will be described below in greater detail. The tubular body 50 is an angular tube having a square opening with a side of 10 mm. The inner space of the tubular body is divided in two equal spaces by the partition wall 54. As a result, the monitoring space and outer space have respective openings of 5 mm×10 mm. In the ultrasound wave generating element 140, an ultrasound wave generating surface that supplies vibrations into the air serving as a medium has a square shape with a side of 10 mm. The ultrasound wave generating element 140 is disposed so that ultrasound waves are generated equally in the monitoring space and outer space. In this case, the initial value of the output of the second wave receiving element 130 is equal to the standard value of the output of the first wave receiving element 120. When the ultrasound wave generating element 140 is not disposed so that ultrasound waves are generated equally in the monitoring space and outer space or when the shape of the monitoring space is different from that of the outer space, the correction coefficient may be calculated by using a ratio of the initial value of the output of the second wave receiving element 130 and the standard value of the output of the first wave receiving element 120.

With the fire sensor of the present embodiment, the effect obtained in addition to the effects described in the seventh embodiment is that the first sound wave generating unit 100 and second sound wave generating unit 110 change in the same manner with the passage of time and the effect of output fluctuations of the first wave receiving element 120 caused by sound pressure variations in the ultrasound wave transmitted from the first sound wave generating unit 100 can be reliably removed with the output correction unit 49 because the first sound wave generating unit 100 and second sound wave generating unit 110 are configured by a single ultrasound wave generating element 140.

Tenth Embodiment

Figure 39:
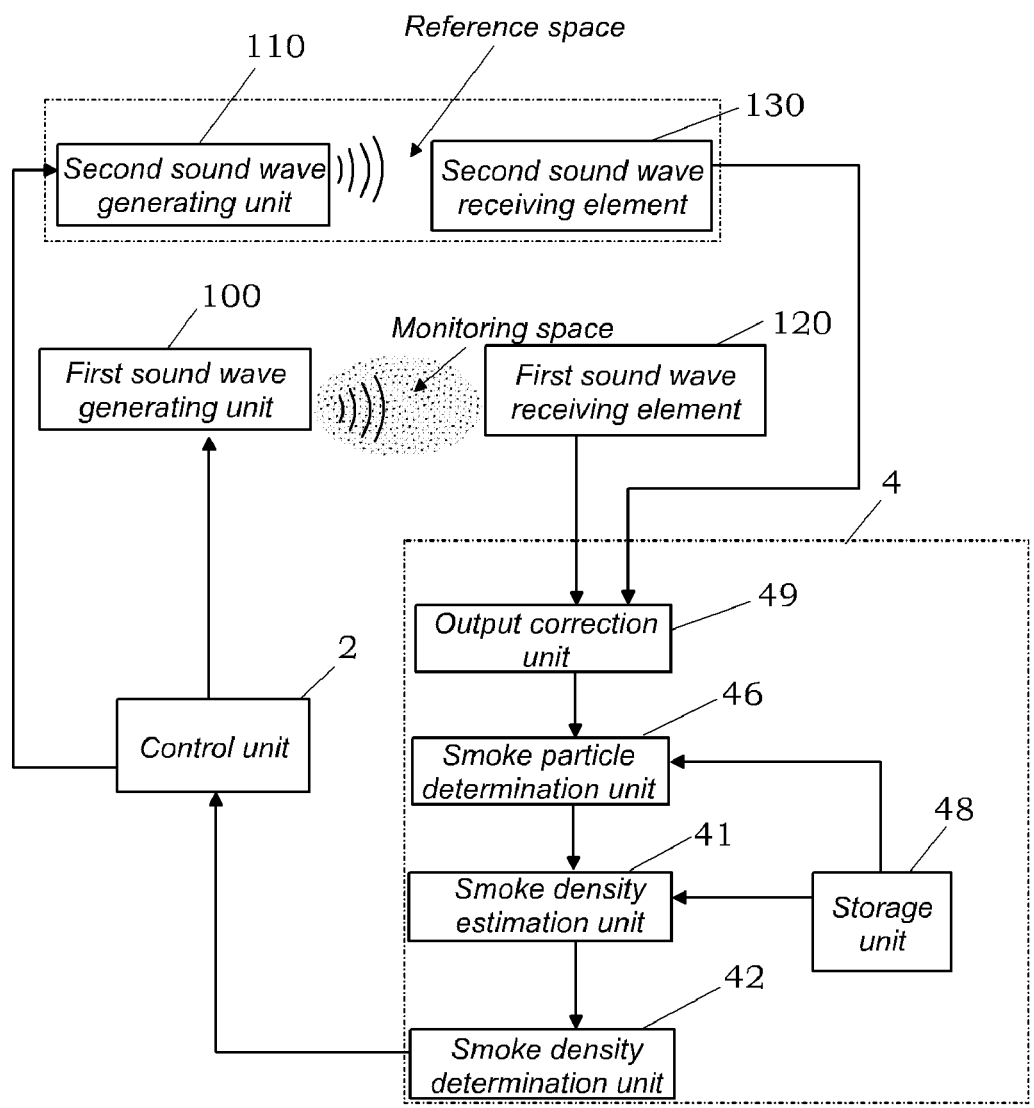
FIG. 39 is a block diagram of a fire sensor in a tenth embodiment of the present invention.

The fire sensor of the present embodiment is substantially identical to the smoke sensor of the second embodiment, except that the sound wave generating unit that generates ultrasound waves is composed of the first sound wave generating unit 100 and second sound wave generating unit 110, the sound wave receiving unit that receives the ultrasound waves is composed of the first wave receiving element 120 and second wave receiving element 130, and the signal processing unit 4 comprises the below-described output correction unit 49 as shown in FIG. 39. Therefore, structural elements identical to those of the second embodiment are assigned with identical reference numerals and redundant explanation thereof is omitted.

In the present embodiment, the control unit 2 controls the first sound wave generating unit 100 so that a plurality of ultrasound waves of different frequencies are successively provided to the monitoring space. The signal processing unit 4 has a storage unit 48 that stores data representing the relationship between the reference output (output of the first wave receiving element 120 related to a standard sound pressure) of at least the first wave receiving element 120, the output frequency of the first sound wave generating unit 100 corresponding to the type of floating particles present in the monitoring space and density of floating particles, and the relative unit attenuation ratio of the output of the first wave receiving element 120 and also a unit attenuation ratio at a specific frequency (for example, 82 kHz) for smoke particles, a smoke particle determination unit 46 that estimates the type of smoke particles floating in the monitoring space by using the output of the first wave receiving element 120 for an ultrasound wave of each frequency generated in the actual monitoring space from the first sound wave generating unit 100 and the relationship data stored in the storage unit 48, a smoke density estimation unit 41 that estimates smoke density in the monitoring space on the basis of the variation amount from a standard value of the output of the first wave receiving element 120 in the ultrasound wave of a specific frequency when the particles estimated by the smoke particle determination unit 46 are the particles determined in advance as a monitoring object, and a smoke density determination unit 42 that determines whether fire is present by comparing the smoke density estimated by the smoke density estimation unit and the predetermined threshold. Further, similarly to the seventh embodiment, the signal processing unit 4 is provided with the output correction unit 49 that corrects the output of the first wave receiving element 120 on the basis of the variation ratio of the output of the second wave receiving element 130 from the initial value, and the processing in the smoke particle determination unit 46 and smoke density estimation unit 41 is performed using the output of the first wave receiving element 120 after the correction in the output correction unit 49 (that is, after removing the effect of variations in ambient environment and variations with time).

The control unit 2 successively changes the frequency of the drive input waveform supplied to the first sound wave generating unit 100, thereby causing the first sound wave generating unit 100 to generate successively a plurality of ultrasound waves having different frequencies. For example, the frequency range of ultrasound waves generated by the first sound wave generating unit 100 is 20 kHz to 82 kHz. Further, in the present embodiment, the control unit 2 controls the first sound wave generating unit 100 so that ultrasound waves of four types having different frequencies are successively transmitted.

Further, in the present embodiment, before various ultrasound waves are transmitted from the first sound wave generating unit 100, ultrasound waves having frequencies identical to those of the waves from the first sound wave generating unit 100 are transmitted from the second sound wave generating unit 110 and the correction coefficient is calculated based on the variation ratio of the output of the second wave receiving element 130 from the initial value. Thus, the control unit 2 successively changes the frequency of the drive input waveform supplied to the second sound wave generating unit 110, thereby causing the second sound wave generating unit 110 to generate successively a plurality of ultrasound waves having different frequencies. For example, the frequency range of ultrasound waves generated by the second sound wave generating unit 110 is 20 kHz to 82 kHz.

The relationship data stored in the storage unit 48 may represent the relationship between the output frequency of the first sound wave generating unit 100 and the attenuation amount of the output of the first wave receiving element 120 from the standard value, or may be the relationship data employing the attenuation amount of the output of the first wave receiving element 120 from the standard value, or the attenuation ratio obtained by dividing the attenuation amount of the output of the first wave receiving element 120 from the standard value by the standard value, or a unit attenuation ratio, instead of the above-described relative unit attenuation ratio.

With the present embodiment, in addition to the effects described in the second embodiment, the effect produced by output correction described in the seventh embodiment can be also obtained. Therefore, it is possible to provide a fire sensor that excels in responsiveness and has few false alarms.

Figure 40:
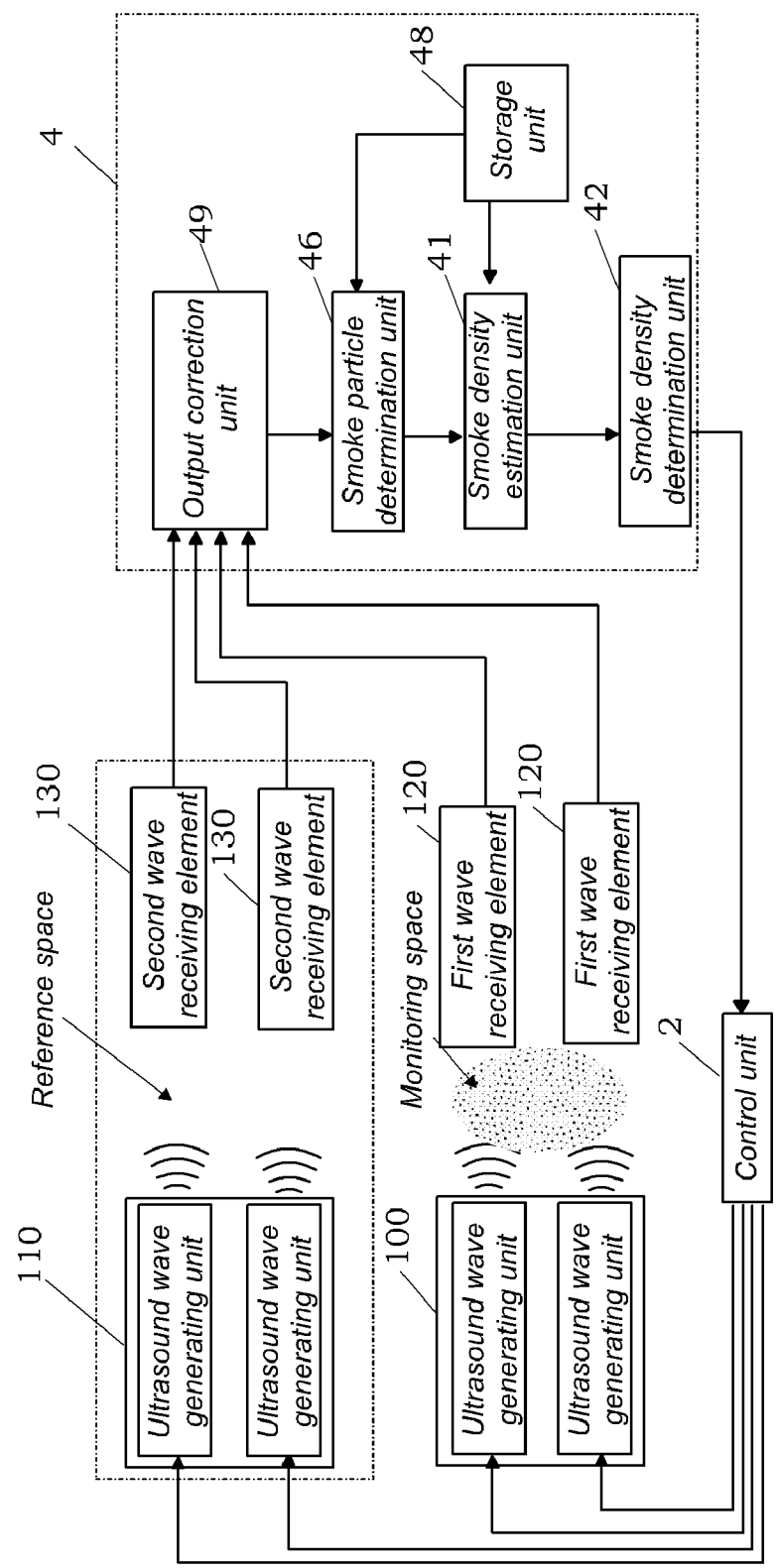
FIG. 40 is a block diagram of a fire sensor of a modification example of the tenth embodiment.

As a modification example of the present embodiment, each of the first sound wave generating unit 100 and second sound wave generating unit 110 may be configured by a plurality of ultrasound wave generating elements that have mutually different output frequencies as shown in FIG. 40. In this case, the sound pressure of ultrasound waves generated from each of the first sound wave generating unit 100 and second sound wave generating unit 110 can be increased and the SN ratio can be raised by using elements generating ultrasound waves by mechanical oscillations, such as piezoelectric elements, as the ultrasound wave generating elements and driving the ultrasound wave generating elements at respective resonance frequencies. Further, it is possible not only to drive the ultrasound wave generating elements sequentially and generate a plurality of ultrasound waves sequentially, but also to drive a plurality of the ultrasound wave generating elements at once and generate a plurality of the ultrasound waves simultaneously. In this case, the attenuation amount of sound pressure of a plurality of ultrasound waves can be detected at the same time, the attenuation amount of sound pressure of a plurality of ultrasound waves can be detected, without being affected by short-term variations in the monitoring space with time (for example, changes in density of floating particles), and the type of floating smoke particles and smoke density can be estimated more accurately.

Figure 41:
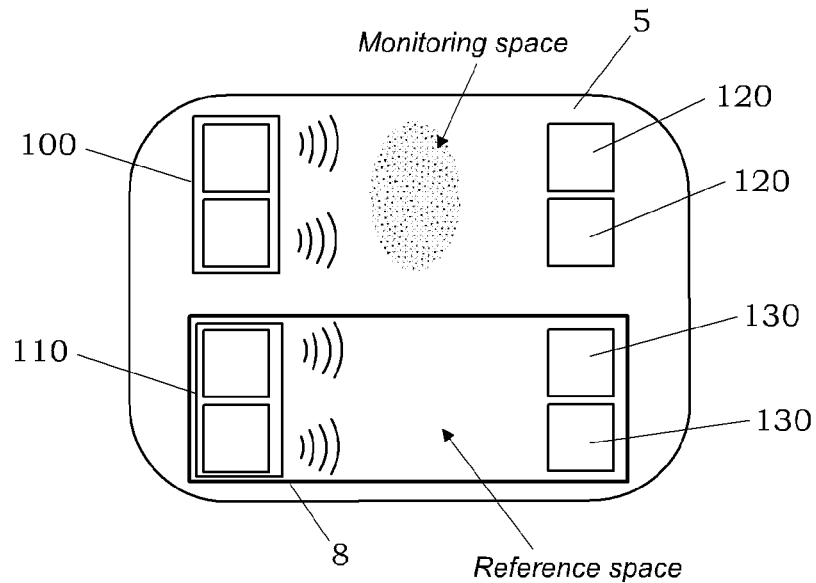
FIG. 41 is a schematic plan view of a fire sensor of a modification example of the tenth embodiment.

Further, in the case of the fire sensor shown in FIG. 40, a first wave receiving element 120 may be disposed for each of a plurality of ultrasound wave generating elements constituting the first sound wave generating unit 100 so as to face the ultrasound wave generating element, and a second wave receiving element 130 may be disposed for each of a plurality of the ultrasound wave generating elements constituting the second sound wave generating unit 110 so as to face the ultrasound wave generating element as shown in FIG. 41. In this case, the sensitivity of the first wave receiving element 120 and second wave receiving element 130 can be increased by using piezoelectric elements with a comparatively large Q value of resonance characteristic for each first wave receiving element 120 and each second wave receiving element 130 and use each first wave receiving element 120 and each second wave receiving element 130 for receiving the ultrasound wave of respective resonance frequency.

Alternatively, based on the technological concept identical to that of the fire sensor shown in FIG. 12, it is possible to use the first sound wave generating unit 100 and first wave receiving element 120 and also the second sound wave generating unit 110 and second wave receiving element 130 as ultrasound wave generating elements suitable both for generating and receiving ultrasound waves, such as piezoelectric ultrasound wave sensors. In this case, although it is necessary to provide a reflective surface that will reflect the ultrasound waves generated from each ultrasound wave generating element toward the ultrasound wave generating element, the cost can be reduced due to reduced number of elements.

Furthermore, a configuration may be employed in which the calculation of correction coefficient is performed once each time a plurality of ultrasound waves are generated from the first sound wave generating unit 100. For example, in an environment with small fluctuations of correction coefficient, the correction coefficient can be calculated (that is, updated) less frequently, thereby reducing power consumption. In this case, it is not necessary to transmit a plurality of ultrasound waves from the second sound wave generating unit 110, and the correction coefficient may be calculated based on the variation amount of the output of the second wave receiving element 130 from the initial value, this variation amount being related to an ultrasound wave of a specific frequency (for example, 82 kHz).

Further, similarly to the fire sensor of the seventh embodiment, the signal processing unit 4 of the fire sensor of the present embodiment may include the sound velocity detection unit 43, temperature estimation unit 44, and temperature estimation unit 45, thereby making it possible to increase further the fire estimation accuracy.

Eleventh Embodiment

Figure 42:
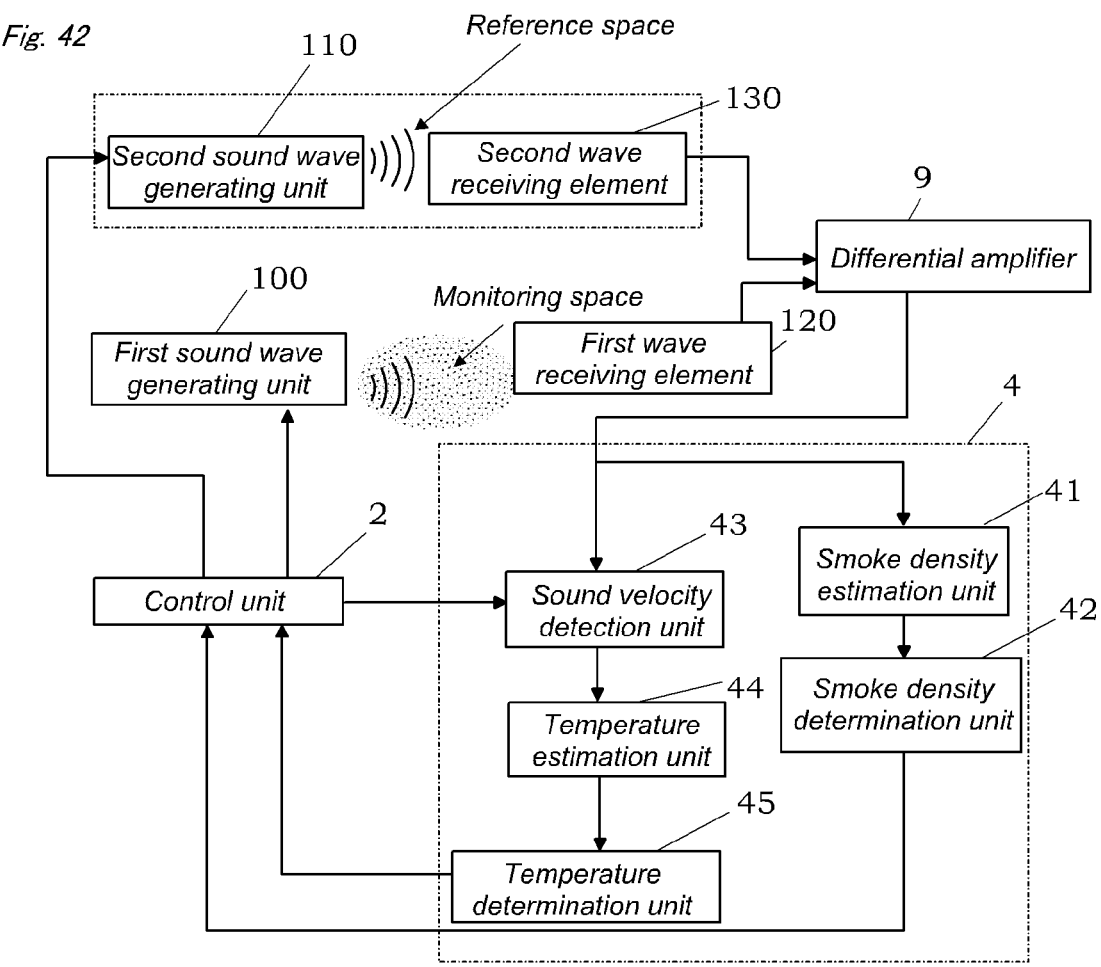
FIG. 42 is a block diagram of a fire sensor of an eleventh embodiment of the present invention.

The fire sensor of the present embodiment is substantially identical to the fire sensor of the first embodiment, except that the sound wave generating unit is configured by the first sound wave generating unit 100 and second sound wave generating unit 110, the sound wave receiving unit that receives the ultrasound waves is configured by the first wave receiving unit 120 and second wave receiving element 130, and a differential amplifier 9 is provided that amplifies and outputs the difference between the output of the first wave receiving element 120 and the output of the second wave receiving element 30, as shown in FIG. 42. Therefore, structural elements identical to those of the first embodiment are assigned with identical reference numerals and redundant explanation thereof is omitted.

In the present embodiments, the first sound wave generating unit 100 and first wave receiving element 120 are disposed opposite each other via a monitoring space and the second sound wave generating unit 110 and second wave receiving element 130 are disposed opposite each other via a reference space on the surface of a circuit substrate 5 composed of a disk-shaped printed circuit board, in the same manner as shown in FIG. 35. The control unit 2, differential amplifier 9, and signal processing unit 4 are provided on the circuit substrate 5. Further, the tubular body 51 is disposed between the first sound wave generating unit 100 and first wave receiving element 120, and the tubular body 52 is disposed between the second sound wave generating unit 110 and the second wave receiving element 130. Ultrasound waves provided by the first sound wave generating unit 100 and second sound wave generating unit 110 pass inside the tubular bodies 51, 52, thereby making it possible to prevent the sound pressure of the ultrasound waves from decreasing due to diffusion. A plurality of holes 53 having a size enabling the passage of floating particles including smoke particles are provided in the tubular body 51, and the monitoring space and an outer space communicate via the holes 53. The tubular body 52 also serves as a shielding wall and has at least in part thereof a filter (for example, a porous ceramic filter) having formed therein a large number of fine holes (not shown in the figure) of a size that prevents the passage of floating particles. As a result, the conditions in the reference space are identical to those of the outer space and monitoring space not only in terms of temperature, but also in terms of humidity and atmospheric pressure.

An ultrasound wave generating element identical to that of the first embodiment can be used in each of the first sound wave generating unit 100 and second sound wave generating unit 110, and a microphone of an electrostatic capacity type that is identical to that of the first embodiment can be employed in each of the first wave receiving element 120 and second wave receiving element 130. Further, the signal processing unit 4 has functions identical to those of the signal processing unit 4 of the first embodiment, except that the signal processing unit receives the output from the below-described differential amplifier 9.

The control unit 2 is configured by a drive circuit that supplies a drive input waveform to drive the first sound wave generating unit 100 and second sound wave generating unit 110 and a control circuit configured by a microcomputer that controls the drive circuit. The control unit 2 has two control modes: a synchronous mode in which ultrasound waves are generated from the first sound wave generating unit 100 and second sound wave generating unit 110 so that that the ultrasound wave generated from the first sound wave generating unit 100 has the same frequency and the same phase as the ultrasound wave generated from the second sound wave generating unit 110, and an asynchronous mode in which ultrasound waves are generated only from either the first sound wave generating unit 100 or the second sound wave generating unit 110.

In the present embodiment the first sound wave generating unit 100 and second sound wave generating unit 110 are driven under identical conditions (for example, sound pressure of ultrasound wave) and the first wave receiving element 120 and second wave receiving element 130 are used under the same conditions (for example, a DC bias voltage). Furthermore, the phase relationship of the first sound wave generating unit 100 and first wave receiving element 120 is set identically to that of the second sound wave generating unit 110 and second wave receiving element 130. Therefore, when the control unit 2 controls the first sound wave generating unit 100 and second sound wave generating unit 110 in the synchronous mode, if no floating particles penetrate into the monitoring space and the monitoring space and reference space are in the same state (for example, in terms of temperature, humidity, and atmospheric pressure), the output of the first wave receiving element 120 has not only the same frequency and phase, but also the same intensity as the output of the second wave receiving element 130.

The differential amplifier 9, which is a specific unit of the present embodiment, will be described below in greater detail. As described hereinabove, the differential amplifier 9 takes the difference between the output of the first wave receiving element 120 and the output of the second wave receiving element 130 and then amplifies and outputs this difference. The output of the differential amplifier 9 in the case where the control unit 2 controls the first sound wave generating unit 100 and second sound wave generating unit 110 in a synchronous mode will be referred to hereinbelow as "differential output". In other words, the differential output is equivalent to the difference in output between the first wave receiving element 120 and second wave receiving element 130 obtained when the control unit 2 synchronously controls the first sound wave generating unit 100 and second sound wave generating unit 110 so that the output of the first wave receiving element 120 and that of the second wave receiving element 130 have the same frequency and same phase. Therefore, the differential output is zero when no floating particles penetrate into the monitoring space and the monitoring space and reference space are in the same state (for example, in terms of temperature, humidity, and atmospheric pressure), as described hereinabove.

The differential output is sent to the smoke density estimation unit 41 of the signal processing unit 4. The smoke density estimation unit 41 estimates the density of smoke based on the variation amount of the differential output from the aforementioned initial value (zero), the differential output being the output of the differential amplifier 9 when the first sound wave generating unit 100 and second sound wave generating unit 110 are controlled by the control unit 2 in the synchronous mode. Thus, although the attenuation amount of the output of the first wave receiving element 120 that receives an ultrasound wave from the first sound wave generating unit 100 via the monitoring space increases almost proportionally to smoke density in the monitoring space, the output of the second wave receiving element 130 receiving an ultrasound wave from the second sound wave generating unit 110 via the reference space that is shielded from the penetration of floating particles is not changed by the variations in smoke density in the monitoring space. Therefore, the variation amount of the differential output corresponding to the difference in output between the first wave receiving element 120 and second wave receiving element 130 increases almost proportionally to smoke density in the monitoring space. Therefore, if an equation representing the relationship between smoke density and variation amount is found based on the data representing the relationship between smoke density and variation amount of differential output that have been measured in advance and this equation is stored, then smoke density can be estimated from the variation amount of the differential output. A feature of determining the presence of fire based on the output of smoke density estimation unit 41 and generating an alarm sound is identical to that of the first embodiment and the explanation thereof is herein omitted.

The sound velocity detection unit 43 finds the sound velocity by using the distance between the first sound wave generating unit 100 and first wave receiving element 120 and the difference in time between the transmission of the ultrasound wave from the first sound wave generating unit 100 and the reception thereof by the first wave receiving element 120. The control unit 2 may control the first sound wave generating unit 100 in an asynchronous mode and cause the first sound wave generating unit 100 to transmit periodically an ultrasound wave of the predetermined frequency, separately from the ultrasound wave from the first sound wave generating unit 100 that serves to estimate the smoke density, and the sound velocity detection unit 43 may find the sound velocity on the basis of difference in time between the transmission of this ultrasound wave of the predetermined frequency and the reception thereof by the first wave receiving element 120. Alternatively, an ultrasound wave may be generated from the second sound wave generating unit 110 and the sound velocity may be found based on the difference in time between the transmission of this ultrasound wave and the reception thereof by the second wave receiving element 130. The temperature estimation unit 44 estimates the temperature in the monitoring space from the sound velocity by using a well-known equation representing the relationship between sound velocity in the air and absolute temperature. A feature of determining the presence of fire based on the output of temperature estimation unit 44 and generating an alarm sound is identical to that of the first embodiment and the explanation thereof is herein omitted.

Figure 43:
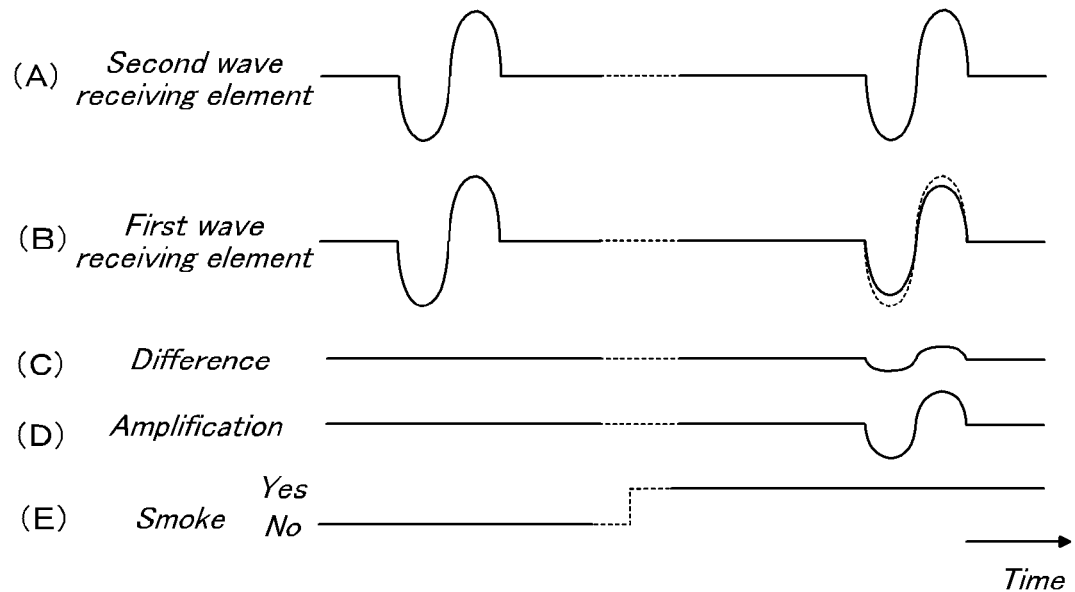
FIGS. 43A to 43E are explanatory drawings illustrating the operation of a fire sensor of the eleventh embodiment

The operation of the fire sensor of the present embodiment will be explained below with reference to FIG. 43. The control unit 2 periodically controls the first sound wave generating unit 100 and second sound wave generating unit 110 in the synchronous mode, whereby ultrasound waves are simultaneously generated from the first sound wave generating unit 100 and second sound wave generating unit 110. Where no smoke is present in the monitoring space ("No Smoke" in FIG. 5E), the output of the second wave receiving element 130 shown in FIG. 5A is identical to the output of the first wave receiving element 120 shown in FIG. 5B, and the difference between the two becomes zero, as shown in FIG. 5C. Therefore, the differential output shown in FIG. 5D that is the output of the differential amplifier 9 obtained by amplifying the output shown in FIG. 5C also becomes zero (initial value). In this case, the smoke density estimation unit 41 estimates the density of smoke in the monitoring space on the basis of the variation amount of the differential output from the initial value, but because the variation amount of the differential output from the initial value is zero, the estimated smoke density is less than the threshold and the smoke density determination unit 42 determines that there is "No Fire".

Where smoke is present in the monitoring space ("Smoke is Present" in FIG. 5E), although the output of the second wave receiving element 130 shown in FIG. 5A does not change, the output of the first wave receiving element 120 shown in FIG. 5B attenuates correspondingly to smoke density in the monitoring space and a difference between the two outputs, such as shown in FIG. 5C, is produced. Therefore, the differential output, which is the output of the differential amplifier 9 obtained by amplifying the difference shown in FIG. 5C, changes from zero (initial value) (FIG. 5D). The variation amount of the differential output from the initial value in this case increases almost proportionally to smoke density in the monitoring space. In this case, the smoke density estimation unit 41 estimates the smoke density in the monitoring space on the basis of the variation amount of the differential output from the initial value, and the smoke density determination unit 42 determines that "Fire is Present" when the smoke density estimated by the smoke density estimation unit 41 is equal to or higher than the threshold.

As a modification example of the present embodiment, the first sound wave generating unit 100 and second sound wave generating unit 110 may be driven under different conditions and the first wave receiving element 120 and second wave receiving element 130 may be used under different conditions. In this case, when floating particles do not penetrate in the monitoring space and the monitoring space and reference space are in the same state (for example, temperature, humidity, and atmospheric pressure), although the ultrasound waves of the same frequency and phase are transmitted from the first sound wave generating unit 100 and second sound wave generating unit 110, the differential output is not zero, but if the differential output in this case is taken as an initial value, smoke density in the monitoring space can be estimated based on the variation amount of the differential output from the initial value.

With the fire sensor of the present embodiment, in addition to the effects described in the first embodiment, because the differential amplifier 9 is provided, the density of smoke in the monitoring space is estimated based on the variation amount of the differential output from the initial value, rather than based on the output of the first wave receiving element 120 alone. Therefore, even when ambient conditions change, the density of smoke in the monitoring space can be estimated with good accuracy that is not affected by these changes. As a result, the operation reliability of the fire sensor can be further increased. Thus, the output of the first wave receiving element 120 can change, regardless of smoke density in the monitoring space, because the sound pressure of the ultrasound wave generated from the first sound wave generating unit 100 changes in response to variations in ambient environment (for example, variations in temperature, humidity, and atmospheric pressure), the attenuation ratio of ultrasound wave propagating in air, which is the medium, changes even when smoke density is constant, and the sensitivity of the first wave receiving element 120 changes, but because output fluctuations identical to the output fluctuations of the first wave receiving element 120 in this case also occur in the output of the second wave receiving element 130, the output fluctuations of the first wave receiving element 120 and output fluctuations of the second wave receiving element 130 cancel each other in the differential output equivalent to the difference in output between the first wave receiving element 120 and second wave receiving element 130, thereby making it possible to remove reliably the effect of output fluctuations.

Twelfth Embodiment

Figure 44:
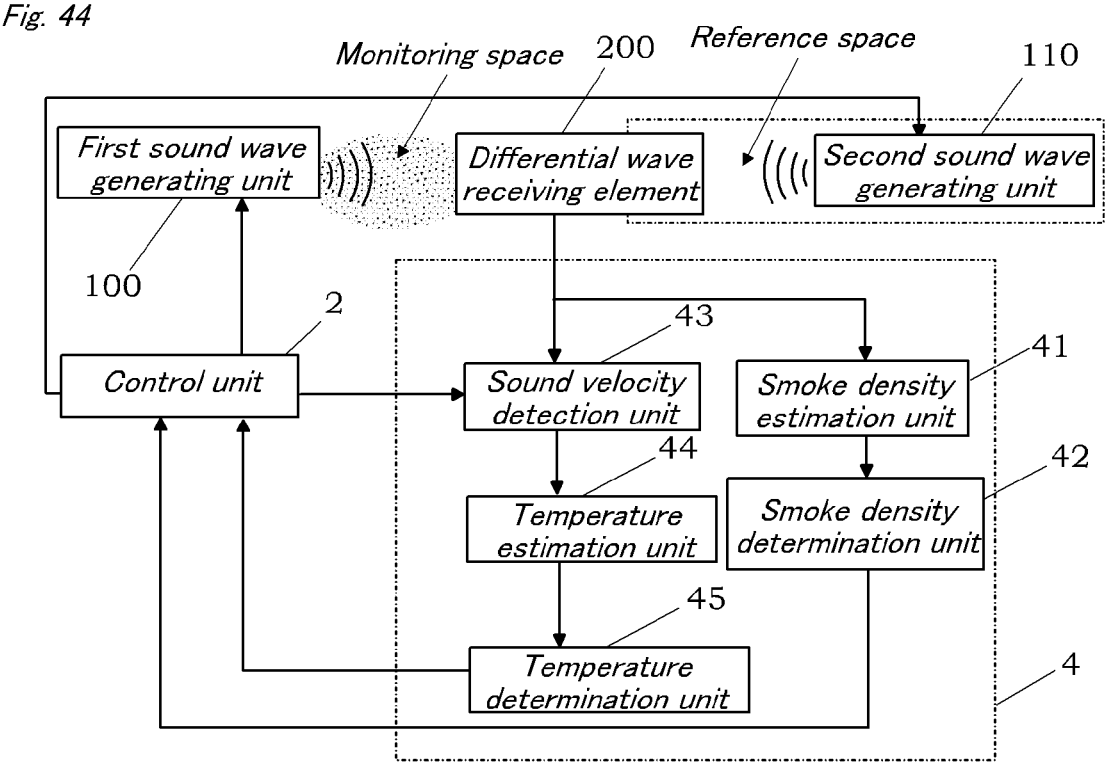
FIG. 44 is a block diagram of a fire sensor of a twelfth embodiment of the present invention.

The fire sensor of the present embodiment is substantially identical to that described in the eleventh embodiment, except that the first wave receiving element 120 and second wave receiving element 130 are configured by a single differential wave receiving element 200, as shown in FIG. 44. Therefore, structural elements identical to those of the eleventh embodiment and embodiments cited by the eleventh embodiment are assigned with identical reference numerals and redundant explanation thereof is omitted.

In the present embodiment, as shown in FIG. 45, the tubular body 51 forming a monitoring space and the tubular body 52 forming a reference space are arranged by stacking in the thickness direction of the circuit substrate 5. As a result, the monitoring space and reference space are adjacent to each other in the vertical direction and separated by a partition 55. The partition 55 may be a common side wall of the tubular body 51 and tubular body 52. The end surface of the tubular body 51 on the side opposite the first sound wave generating unit 100 in the longitudinal direction of the tubular body and the end surface of the tubular body 52 on the side opposite the second sound wave generating unit 110 in the longitudinal direction of the tubular body are open.

The differential wave receiving element 200 is provided in the aforementioned partition 55 that separates the monitoring space and reference space. In the differential wave receiving element 200, pressure receiving portions are formed that receive sound pressure on the side of the monitoring space, which is the inner space of the tubular body 51, and the side of the reference space, which is the inner space of the tubular body 52, and the difference between the sound pressures received by the two pressure receiving portions is detected. Further, although not shown in FIG. 44, an amplifier for amplifying the output of the differential wave receiving element 200 is provided between the differential wave receiving element 200 and signal processing unit 4. In this case, the output of the differential wave receiving element 200 obtained when the control unit 2 controls the first sound wave generating unit 100 and second sound wave generating unit 110 in the synchronous mode is amplified by the amplifier and the amplified output is taken as a differential output. In other words, where the first wave receiving element 120 and second wave receiving element 130 are thus combined in a single differential wave receiving element 200, a component equivalent to the difference in output between the first wave receiving element 120 and second wave receiving element 130 can be directly taken out from the differential wave receiving element 200. Therefore, the differential amplifier 9 that amplifies the difference in output between the first wave receiving element 120 and second wave receiving element 130, as explained in the eleventh embodiment, is unnecessary.

As a modification example of the present embodiment, the inner space of a single tubular body 50 may be equally divided into a monitoring space and a reference space by the partition 55 provided in the central portion in the longitudinal direction as shown in FIG. 46. This tubular body 50 has holes 53 formed to a size such that floating particles including smoke particles can pass through into the monitoring space, and these holes link the inside of the monitoring space with the outside. The first sound wave generating unit 100 and second sound wave generating unit 110 are disposed at both end surfaces in the longitudinal direction of the tubular body 50. A portion of the tubular body 50 that forms the reference space also serves as a shielding wall and has in at least part thereof a filter (for example, a porous ceramic filter) having formed therein a large number of fine holes (not shown in the figure) of a size that prevents the passage of floating particles. Because the reference space and outer space are linked to each other by these fine holes, although the penetration of floating particles into the reference space is prevented, variations in the ambient environment of the fire sensor, for example, humidity or atmospheric pressure, can be reflected in the reference space and the effect of output fluctuations caused by such variations can be removed from the differential output.

The differential wave receiving element 200 used in the present embodiment will be explained below. The differential wave receiving element 200 is composed of a microphone of an electrostatic capacity type that has a fixed electrode and a movable electrode disposed opposite each other and in which the distance between the fixed electrode and movable electrode changes correspondingly to the difference in sound pressure received by the two pressure receiving portions, and the electrostatic capacity between the electrodes changes accordingly. For example, as shown in FIGS. 47A and 47B, the differential wave receiving element 200 includes a pair of frames 210 of a rectangular shape having formed therein window holes 211 that pass therethrough in the thickness direction to a respective silicon substrate, a fixed plate 230 composed of an electrically conductive material and sandwiched between the two frames 210, and a pair of movable electrodes 220 composed of an electrically conductive material and formed in a shape that closes the respective window holes 211 at the surface of each frame 210 that is opposite the fixed plate 230. The fixed plate 230 has a fixed electrode 232 within the window hole 211, and each movable plate 220 has a respective movable electrode 222 in a location opposite the fixed electrode 232. In this case, a flexible portion 223 that is held so that the movable electrode 222 can oscillate in the thickness direction of the frame 210 is formed around the movable electrode 222 in the movable plate 220. Furthermore, the two movable electrodes 222 are joined together by joining pieces 224 composed of an electrically conductive material and passing through holes 233 provided in the fixed plate 232, and the movable electrodes operate integrally. Each movable plate 220 is electrically connected to a pad 221 formed around the respective window hole 211, and the fixed plate 230 is electrically connected to a pad 231 formed on one surface of one frame 210 by a through hole wiring 234 formed in the frame 210. Although not shown in FIG. 47A, the frame 210 has insulating films in contact locations of the fixed plate 230, movable plate 220, pads 221, 231, and through hole wiring 234. In the present embodiment, the movable plate 220 and fixed plate 230 are formed from respective metal thin films, but they may be also formed from other materials. The flexible portion 223 may have, for example, a corrugated structure.

In the differential wave receiving element 200 configured by a microphone of an electrostatic capacity type that has the configuration shown in FIGS. 47A and 47B, because a capacitor is formed that has the fixed electrode 232 and both movable electrodes 222 as electrodes, each movable electrode 232 functions as a respective pressure receiving portion, and where the distance between the fixed electrode 232 and movable electrodes 222 changes because a pressure of a dilatational wave is received, the electrostatic capacity between these electrodes changes. Since the two movable electrodes 222 operate integrally, the electrostatic capacity between the fixed electrode 232 and two movable electrodes 222 varies correspondingly to the difference between a sound pressure received by one movable electrode 222 and a sound pressure received by the other movable electrode 222. Therefore, where a DC bias voltage is applied between the pad 231 electrically connected to the fixed electrode 232 and the pad 221 electrically connected to each movable electrode 222, very small voltage variations occur correspondingly to the sound pressure of ultrasound wave between the pads, thereby making it possible to convert the sound pressure of ultrasound wave into an electric signal. In this case, because the two pads 221 are electrically connected via the joining pieces 224, the DC bias voltage may be applied to any one of the pad 221 and pad 231. By forming the joining pieces 224 from an electrically insulating material, a configuration can be obtained in which the two movable electrodes 222 are electrically separated, and variations in electrostatic capacity between the fixed electrode 232 and any one movable electrode 222 may be measured.

In the differential wave receiving element 200 of such a configuration, where one movable plate 220 is installed at the partition 55, which separates the monitoring space and the reference space, so as to face the monitoring space, and the other movable plate 220 is installed so as to face the reference space, then a difference between the sound pressure of ultrasound wave received from the first sound wave generating unit 100 in the monitoring space and the sound pressure of ultrasound wave received from the second sound wave generating unit 110 in the reference space is outputted. The advantage of such a configuration is that differential wave receiving element 200 has a flat frequency characteristic and the generation time period of a reverberation component in the output is short.

The signal processing unit 4 of the present embodiment has an output correction unit (not shown in the figure) that measures the output of the differential wave receiving element 200 in a state in which the control unit 2 controls the second sound wave generating unit 110 in the asynchronous mode and an ultrasound wave is transmitted only from the second sound wave generating unit 110 and corrects the differential output based on the variation amount of the output of the differential wave receiving element 200 from the initial value. Thus, the output correction unit stores a correction coefficient based on the variation ratio of the output of the differential wave receiving element 200 from the initial value and outputs the differential output that is corrected using this correction coefficient to the smoke density estimation unit 41. The initial value of the output of the differential wave receiving element 200 is an output value of the differential wave receiving element 200 detected when there are no changes in the fire sensor with time (for example, deterioration with time), for example, in the manufacturing process or prior to shipping, and this value is held in the output correction unit in advance. Alternatively, the initial value of the output of the differential wave receiving element 200 may be set by a program. In the configuration of the present embodiment, the control unit 2 and signal processing unit 4 are so configured that the second sound wave generating unit 110 is driven, the output of the differential wave receiving element 200 is measured, and the correction coefficient is calculated each time before the first sound wave generating unit 100 and second sound wave generating unit 110 are driven and smoke density in the monitoring space is measured. Therefore, the correction coefficient is updated each time the smoke density in the monitoring space is detected. The variation ratio of the output of the differential wave receiving element 200 from the initial value is determined according to variations in the first sound wave generating unit 100 and second sound wave generating unit 110 or differential wave receiving element 200 with time (for example, deterioration with time), and where the differential output is corrected using the correction coefficient based on the rate of these variations, a differential output from which the effect of variations with time and the like has been removed is obtained, thereby increasing the estimation accuracy of smoke density in the monitoring space.

Figure 48:
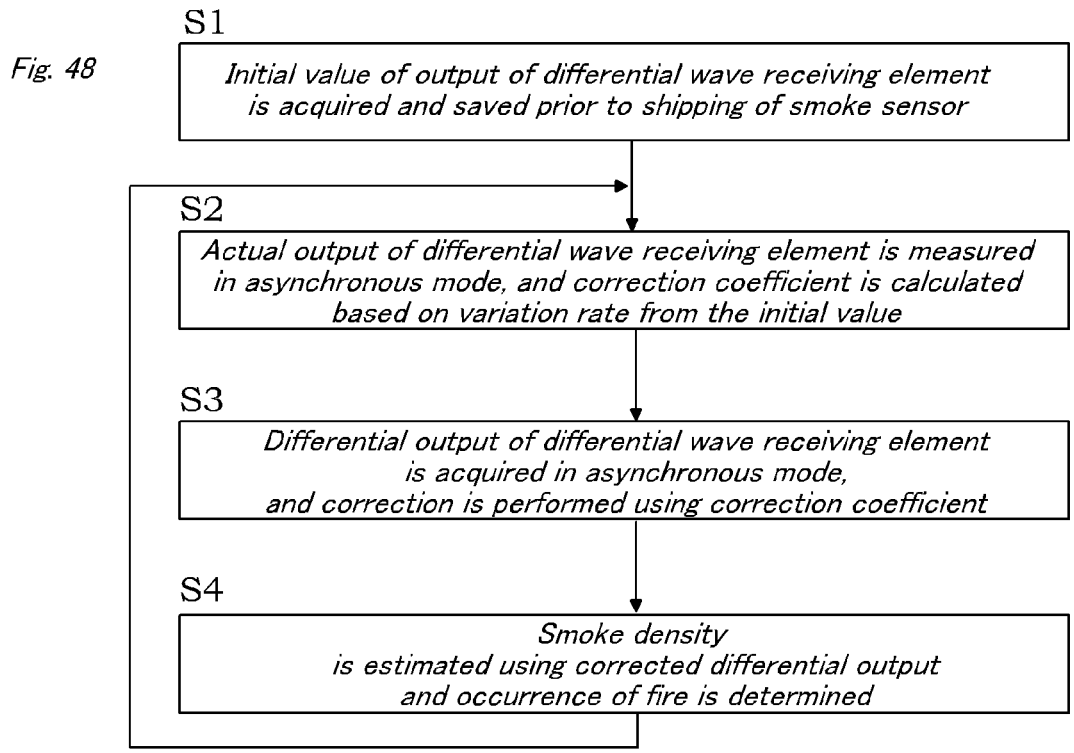
FIG. 48 is a flowchart illustrating an operation example of a fire sensor of the twelfth embodiment.

An operation example of the fire sensor in accordance with the present invention will be described hereinbelow with reference to a flowchart shown in FIG. 48. Before the fire sensor is shipped, the second sound wave generating unit 110 is driven in the asynchronous mode, the initial value of the output (reference value) of the differential wave receiving element 200 is acquired, and the initial value is held in the output correction unit (step S1). Then, after the fire sensor has been installed in the desired location and before the first sound wave generating unit 100 and second sound wave generating unit 110 are driven in the synchronous mode, the second sound wave generating unit 110 is driven in the asynchronous mode, the output of the differential wave receiving element 200 is measured, and the correction coefficient is calculated based on the variation ratio of the output of the differential wave receiving element 200 from the aforementioned initial value (step S2). The first sound wave generating unit 100 and second sound wave generating unit 110 are then driven in the synchronous mode, the differential output is acquired, and the differential output is corrected in the output correction unit by using the correction coefficient, thereby removing the effect of variations with time from the differential output (step S3). The differential output after the correction is used to estimate the smoke density in the monitoring space in the smoke density estimation unit 41 and the presence or absence of fire is determined in the smoke density determination unit 42 (step S4). If step S4 is completed, the processing flow is returned to step S2 in which the correction coefficient is calculated and the above-described steps S2 to S4 are periodically repeated.

For example, where a decrease in sensitivity in an amount of Msens ($0 \leq Msens \leq 1$) is caused by variations in the differential wave receiving element 200 with time, the differential correction unit can calculate the correction coefficient (1−Msens) from a formula Pref=(1−Msens)×Pref0, and the differential output (Pmes−Pref) can be corrected from Pmes0−Pref0=(1/(1−Msens))×(Pmes−Pref) by using the correction coefficient, where Pref stands for an output (reference value) of the differential wave receiving element 200 obtained when an ultrasound wave is generated only from the second sound wave generating unit 110, Pref0−an initial value of the output of the differential wave receiving element 200, Pmes−an output of the differential wave receiving element 200 obtained when an ultrasound wave is generated only from the first sound wave generating unit 100, and Pmes0−an initial value of the output of the differential wave receiving element 200.

Furthermore, a configuration may be employed in which the calculation of correction coefficient is performed once for a plurality of times the smoke density in the monitoring space is estimated. For example, in an environment with small fluctuations of correction coefficient, the correction coefficient can be calculated (that is, updated) less frequently, thereby reducing power consumption.

With the fire sensor of the present embodiment, the first wave receiving element 120 and second wave receiving element 130 are provided as a single differential wave receiving element 200. The resultant effect is that noise contained in the differential output can be reduced and the SN ratio rises. Furthermore, by periodically correcting the differential output with the output correction unit, it is possible to remove fluctuations of differential output occurring due to variations with time (for example, degradation with time) in the first sound wave generating unit 100 and second sound wave generating unit 110 or differential wave receiving element 200 and long-term operation reliability of smoke detection is increased.

Thirteenth Embodiment

Figure 49:
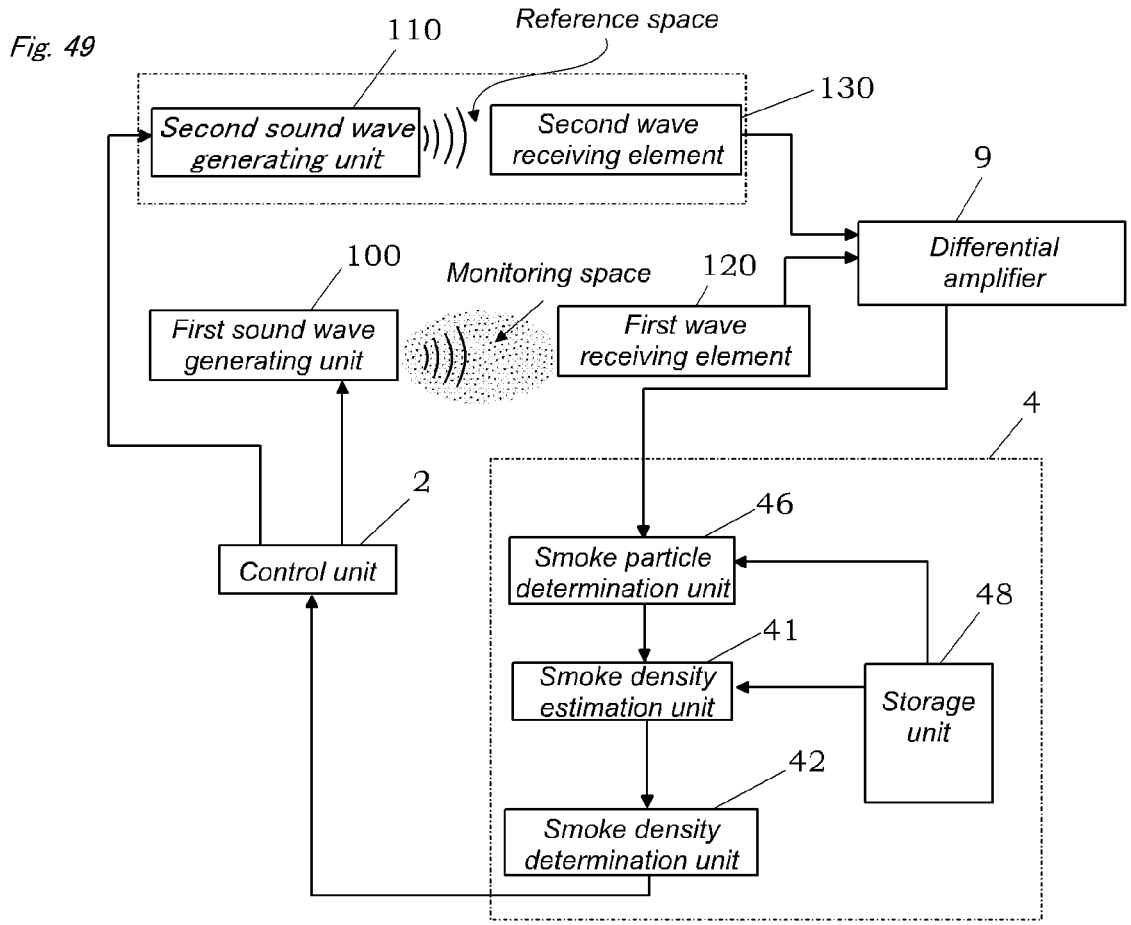
FIG. 49 is a block diagram of a fire sensor of a thirteenth embodiment of the present invention.

The fire sensor of the present embodiment is substantially identical to the fire sensor of the second embodiment, except that the sound wave generating unit that generates ultrasound waves is configured by the first sound wave generating unit 100 and second sound wave generating unit 110, the sound wave receiving unit that receives the ultrasound waves is configured by the first wave receiving element 120 and second wave receiving element 130, and the signal processing unit 4 includes the below-described differential amplifier 9, as shown in FIG. 49. Therefore, structural elements identical to those of the second embodiment are assigned with identical reference numerals and redundant explanation thereof is omitted.

In the present embodiment, the control unit 2 controls the first sound wave generating unit 100 and second sound wave generating unit 110 in the synchronous mode so that a plurality of ultrasound waves of different frequencies are successively generated from the first sound wave generating unit 100 and second sound wave generating unit 110. The storage unit 48 of the signal processing unit 4 stores data representing the relationship at least between the output of the second wave receiving element 130, the output frequency of the first sound wave generating unit 100 corresponding to the type of smoke particles present in the monitoring space and density of smoke particles, and a relative unit variation ratio (equivalent to the relative unit attenuation ratio of the output of the first wave receiving element 120) of the differential output, and also stores a unit variation ratio of the differential output at a specific frequency (for example, 82 kHz) relating to smoke particles. The particle determination unit 46 estimates the type of smoke particles present in the monitoring space by using the relationship data stored in the storage unit 48 and the differential output for ultrasound waves of each frequency generated from the first sound wave generating unit 100 in the actual monitoring space. Furthermore, when the estimated smoke particles are the smoke particles that have been set in advance as a monitoring object, the smoke density estimation unit 41 estimates the smoke density of the monitoring space on the basis of the variation amount of the differential output corresponding to the ultrasound wave of the specific frequency from the initial value. The smoke density determination unit 42 determines the presence or absence of fire by comparing the smoke density estimated in the smoke density estimation unit 41 with the predetermined threshold. A plurality of frequencies may be selected as the specific frequencies and an average value of smoke densities estimated for each specific frequency may be found. In this case, the estimation accuracy of smoke density is further increased.

The relationship data stored in the storage unit 48 may represent the relationship between the output frequency of the first sound wave generating unit 100 and the variation amount of the differential output from the initial value, or may be the relationship data employing the variation amount of the differential output from the initial value, the variation ratio obtained by dividing the variation amount of the differential output from the initial value by the output of the second wave receiving element 130, or a unit variation ratio, instead of the above-described relative unit variation ratio.

Similarly to the fire sensor of the eleventh embodiment, the signal processing unit 4 of the fire sensor of the present embodiment may include the sound velocity detection unit 43, temperature estimation unit 44, and temperature estimation unit 45, thereby making it possible to increase further the fire estimation accuracy.

Thus, with the present embodiment, in addition to the effects identical to those described in the second embodiment, it is also possible to obtain the effects resulting from the addition of the differential amplifier 9 described in the eleventh embodiment. As a result, it is possible to provide a fire sensor that excels in responsiveness and demonstrates very few false alarms.

Fourteenth Embodiment

Figure 50:
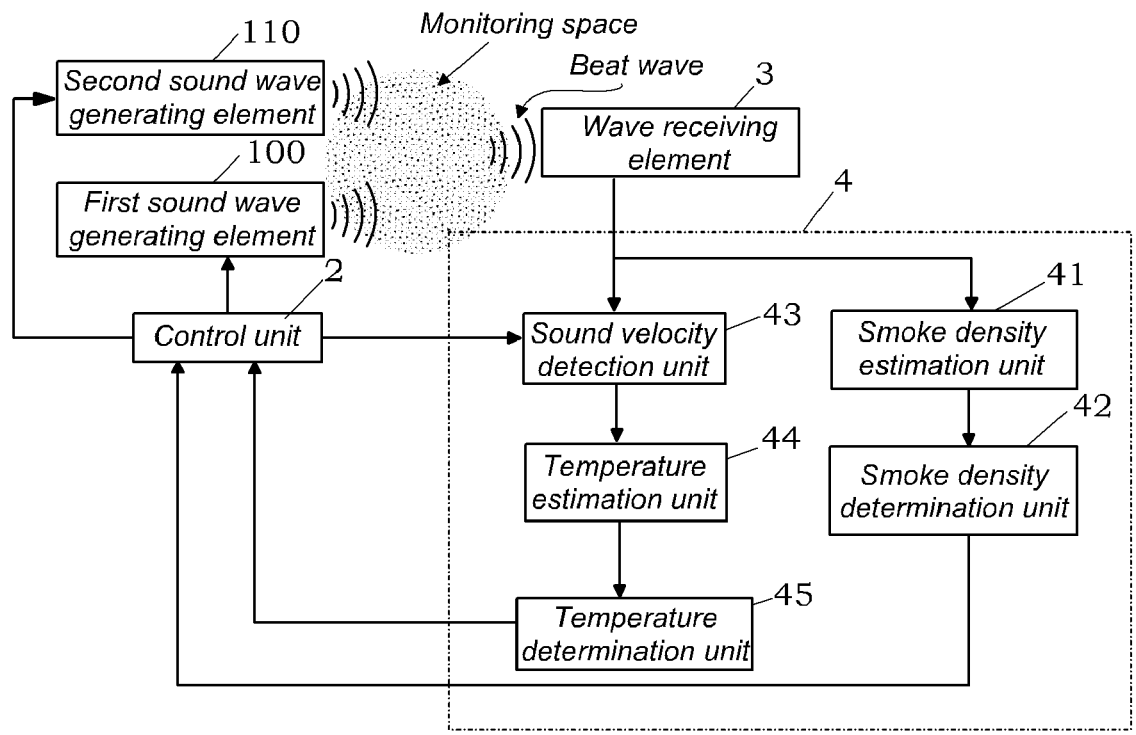
FIG. 50 is a block diagram of a fire sensor of a fourteenth embodiment of the present invention.

The fire sensor of the present embodiment is substantially identical to the fire sensor of the first embodiment, except that the first sound wave generating unit 100 and second sound wave generating unit 110 are provided as an ultrasound wave generating unit, and the wave receiving element 3 receives a dilatational wave (beat wave) having a frequency (fixed frequency) equivalent to the difference in ultrasound wave frequency between the first sound wave generating unit 100 and second sound wave generating unit 110, as shown in FIG. 50. Therefore, structural elements identical to those of the first embodiment are assigned with identical reference numerals and redundant explanation thereof is omitted.

An ultrasound wave generating element identical to that of the first embodiment can be used for each of the first sound wave generating unit 100 and second sound wave generating unit 110, and a microphone of an electrostatic capacity type identical to that of the first embodiment can be employed for the wave receiving element 3. The control unit 2 that controls the first sound wave generating unit 100 and second sound wave generating unit 110 is configured by a drive circuit that supplies a drive input waveform to the first sound wave generating unit 100 and second sound wave generating unit 110 and drives them and a control circuit configured by a microcomputer that controls the drive circuit. Similarly to the first embodiment, the signal processing unit 4 includes the smoke density estimation unit 41, smoke density determination unit 42, sound velocity detection unit 43, temperature estimation unit 44, and temperature estimation unit 45.

Figure 51:
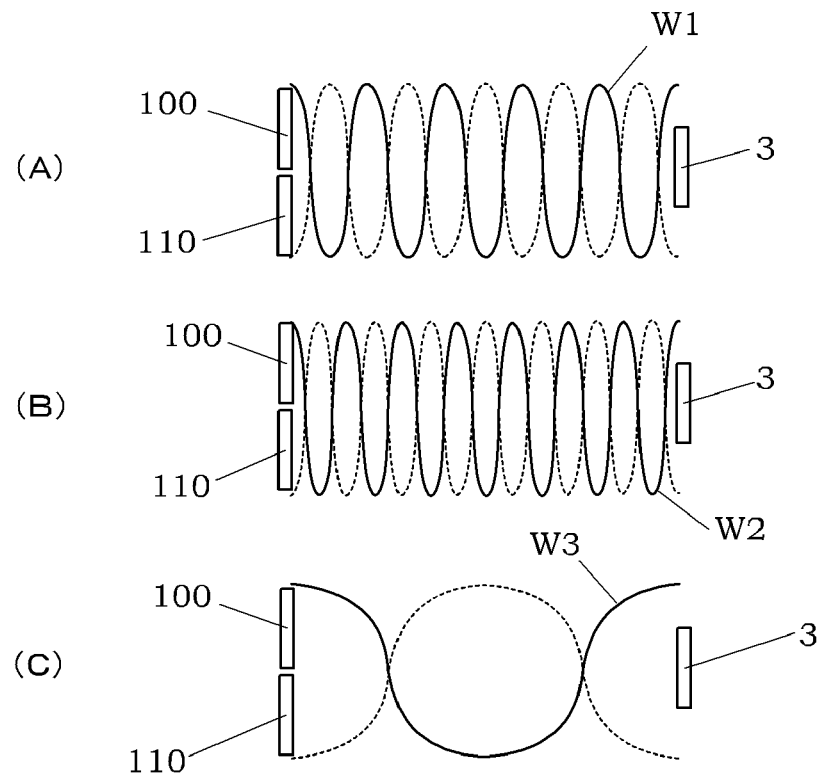
FIGS. 51A to 51C are explanatory drawings illustrating the operation of the fire sensor of the fourteenth embodiment.

In the present embodiment, the first sound wave generating unit 100 and second sound wave generating unit 110 are controlled by the control unit 2 so that the first sound wave generating unit 100 transmits an ultrasound wave of the first frequency (referred to hereinbelow as "first ultrasound wave"), as shown in FIG. 51A, and the second sound wave generating unit 110 transmits an ultrasound wave of the second frequency (referred to hereinbelow as "second ultrasound wave") that is higher than the first frequency, as shown in FIG. 51B. Both the first sound wave generating unit 100 and the second sound wave generating unit 110 are arranged side by side in the same plane so as to oppose the wave receiving element 3. In this case, the second frequency is set to be higher than the first frequency by a predetermined fixed frequency, and the fixed frequency is set lower than at least the first frequency. Furthermore, the control unit 2 controls the first sound wave generating unit 100 and second sound wave generating unit 110 so that ultrasound waves are transmitted from the first sound wave generating unit 100 and second sound wave generating unit 110 into the monitoring space at the same time. If the ultrasound waves transmitted from the first sound wave generating unit 100 and second sound wave generating unit 110 interfere with each other due to nonlinearity of the medium (air) of the monitoring space, a beat wave that is a dilatational wave having a frequency (fixed frequency) corresponding to the difference in frequency between the ultrasound waves is generated, as shown in FIG. 51C. "W1" in FIG. 51A and "W2" in FIG. 51B represent the first ultrasound wave and second ultrasound wave, respectively, and "W3" in FIG. 51C represents the beat wave. In other words, if the first ultrasound wave (W1) and second ultrasound wave (W2) enter the monitoring space as primary waves, the beat wave (W3) having a fixed frequency that is the difference between the second frequency and first frequency is generated as a secondary wave.

An element having sufficient sensitivity with respect to the dilatational wave of the above-described fixed frequency is employed as the wave receiving element 3, and the wave receiving element 3 detects not only the sound pressure of the ultrasound waves transmitted from the first sound wave generating unit 100 or second sound wave generating unit 110, but also the sound pressure of the beat wave. Therefore, with the configuration of the present embodiment, even if comparatively high first frequency and second frequency of ultrasound waves generated from the first sound wave generating unit 100 and second sound wave generating unit 110 are set, a low frequency of the beat wave received by the wave receiving element (that is, the fixed frequency) can be set.

A specific example of the present embodiment will be described below. Where the sound velocity c is 340 m/sec and the distance L between the first sound wave generating unit 100, second sound wave generating unit 110 and the wave receiving element 3 is 34 mm, the frequency of the first ultrasound wave from the first sound wave generating unit 100 is set to 200 kHz and the frequency of the second ultrasound wave from the second sound wave generating unit 110 is set to 220 kHz. In this case, the control unit 2 controls the first sound wave generating unit 100 and second sound wave generating unit 110 so that ultrasound waves each, for example, of about 100 periods are continuously transmitted. In this case, a beat wave with a fixed frequency (=20 kHz), which is the difference between the first frequency (=200 kHz) and second frequency (=220 kHz), is generated in the monitoring space. Therefore, in the wave receiving element 3, the sound pressure of a dilatational wave with a frequency of 20 kHz is detected, and the detection of sound pressure can be performed with sufficient sensitivity even with a typical wave receiving element 3 (not only with the above-described microphone of an electrostatic capacity type, but also, for example, with an electret capacitor microphone).

Further, in the sound velocity detection unit 43 of the signal processing unit 4, a dilatational wave of a predetermined frequency may be periodically transmitted separately from the ultrasound wave used for estimating the smoke density, and the sound velocity may be found based on the time elapsing till the dilatational wave is received by the wave receiving element 3 or on the sound velocity may be found by using the ultrasound wave transmitted to estimate the sound velocity. A feature of estimating the temperature of the monitoring space from the found sound velocity and determining the presence or absence of fire on the basis of the estimated temperature is identical to that of the first embodiment and the explanation thereof is herein omitted.

With the fire sensor of the present embodiment, in addition to the effects identical to those described in the first embodiment, it is possible to detect the sound pressure with sufficient sensitivity by using a typical wave receiving element because the beat wave having a low frequency is received by the wave receiving element 3. Another effect is that because the frequency of ultrasound waves transmitted from the first sound wave generating unit 100 and second sound wave generating unit 110 is high, the output attenuation amount of the wave receiving element 3 caused by smoke particles present in the monitoring space becomes comparatively large and, therefore, the SN value rises.

Fifteenth Embodiment

Figure 52:
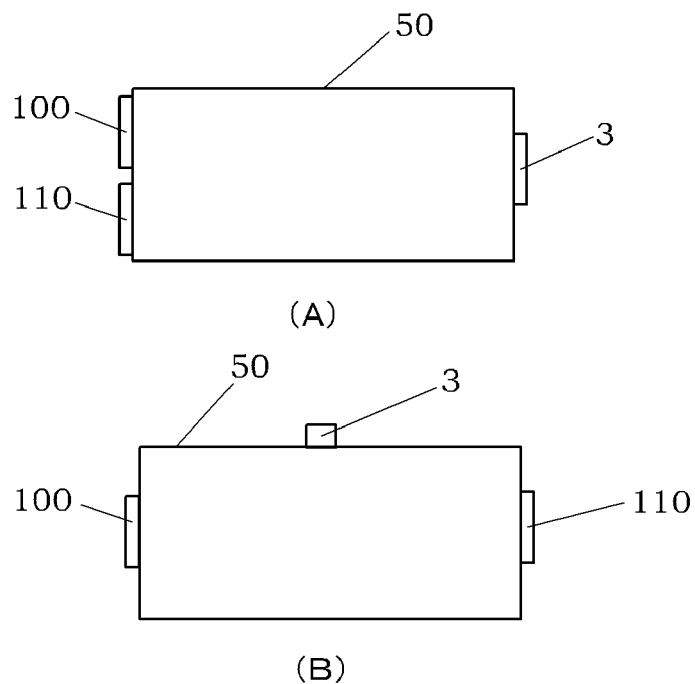
FIGS. 52A and 52B are schematic side views of a fire sensor of a fifteenth embodiment of the present invention.

The fire sensor of the present embodiment is substantially identical to that of the fourteenth embodiment, except that the tubular body 50 that narrows the diffusion range of ultrasound waves and has the inner space thereof used as a propagation path for ultrasound waves is disposed between the first sound wave generating unit 100, second sound wave generating unit 110 and wave receiving element 3, as shown in FIGS. 52A and 52B. Therefore, structural elements identical to those of the fourteenth embodiment and embodiments cited by the fourteenth embodiment are assigned with identical reference numerals and redundant explanation thereof is omitted.

The tubular body 50 shown in FIG. 52A is a straight angular tube, the first sound wave generating unit 100 and second sound wave generating unit 110 are disposed at one end surface in the longitudinal direction and the wave receiving element 3 is disposed at the other end surface. Because the tubular body 50 is provided, the ultrasound wave passes in the inner space of the tubular body 50 and the diffusion thereof is inhibited, thereby inhibiting the decrease in sound pressure of ultrasound wave. With such a configuration the inside of the tubular body 50 serves as the monitoring space. Therefore, a hole (not shown in the figure) that guides smoke and the like into the tube can be formed, for example, in the side surface of the tubular body 50.

The tubular body 50 has an inherent resonance frequency similarly to an acoustic tube closed at both ends in the longitudinal direction. In other words, where the size of the tubular body 50 in the longitudinal direction is denoted by L, a frequency f corresponding to a wavelength $\lambda$ satisfying the relationship $L=(n/2)\times\lambda$ (here, n is a natural number) will be the resonance frequency of the tubular body 50 (this frequency is defined as $f=c/\lambda$, where c stands for a propagation velocity of the ultrasound wave). In the present embodiment, the control unit 2 causes the first sound wave generating unit 100 and second sound wave generating unit 110 to transmit ultrasound waves at a resonance frequency inherent to the tubular body 50. As a result, a resonance is induced inside the tubular body 50 and the sound pressure of ultrasound waves can be increased. In this case, in order to induce the resonance inside the tubular body 50, it is necessary to provide an ultrasound wave with a plurality of periods (referred to hereinbelow as m periods) exceeding $L/\lambda$. Therefore, the control unit causes the first sound wave generating unit 100 and second sound wave generating unit 110 to transmit a continuous ultrasound wave of m ($>L/\lambda$) periods. In other words, the first sound wave generating unit 100 and second sound wave generating unit 110 are controlled by the control unit 2 so that a transmission time $t_p$ (in other words, $t_p=m\times\lambda/c$) of ultrasound waves continuously transmitted from the sound wave generating units becomes longer than a propagation time $t_s$ (in other words, $t_s=L/c$) required for the ultrasound waves to propagate between the two ends in the longitudinal direction of the tubular body 50 (in other words, so that $t_p>t_s$). The wave receiving element 3 detects the sound pressure of the beat wave at a timing at which a resonance is generated inside the tubular body 50 and the sound pressure of ultrasound waves is saturated. The sound pressure of ultrasound waves is usually saturated when the transmission of ultrasound wave from the sound source unit 1 is completed. Therefore, the sound pressure of the beat wave may be detected in the wave receiving element 3, for example, at the same time as the transmission of ultrasound waves from the first sound wave generating unit 100 and second sound wave generating unit 110 is completed.

As shown in FIG. 52B, the first sound wave generating unit 100 and second sound wave generating unit 110 may be disposed at different end surfaces in the longitudinal direction of the tubular body 50, and the wave receiving element 3 may be disposed in the central portion of the side surface extending in the longitudinal direction of the tubular body 50.

With the fire sensor of the present embodiment, in addition to the effects identical to those described in the fourteenth embodiment, by providing the tubular body 50 in the ultrasound wave propagation path between the first sound wave generating unit 100, second sound wave generating unit 110 and the wave receiving element 3, it is possible to inhibit the diffusion of ultrasound waves and prevent the decrease in sound pressure. Furthermore, because the sound pressure of ultrasound waves is increased by inducing a resonance in the tubular body 50, the SN ratio is further increased. In particular, in an ultrasound wave that is repeatedly reflected on the end surfaces in the longitudinal direction of the tubular body 50 due to the resonance, the effective transmission distance increases correspondingly to the number of reflections and the ultrasound wave substantially reaches the wave receiving element 3 via a transmission distance that is several times longer than the size L of the tubular body 50 in the longitudinal direction. As a result, the attenuation amount of ultrasound wave becomes several times that in the configuration in which a non-resonant single-pulse ultrasound wave is received by the wave receiving element 3.

Sixteenth Embodiment

The fire sensor of the present embodiment is substantially identical to that of the fifteenth embodiment, except that the mutual arrangement of the first sound wave generating unit 100, second sound wave generating unit 110, and wave receiving element 3 is different. Therefore, structural elements identical to those of the fifteenth embodiment and embodiments cited by the fifteenth embodiment are assigned with identical reference numerals and redundant explanation thereof is omitted.

Figure 53:
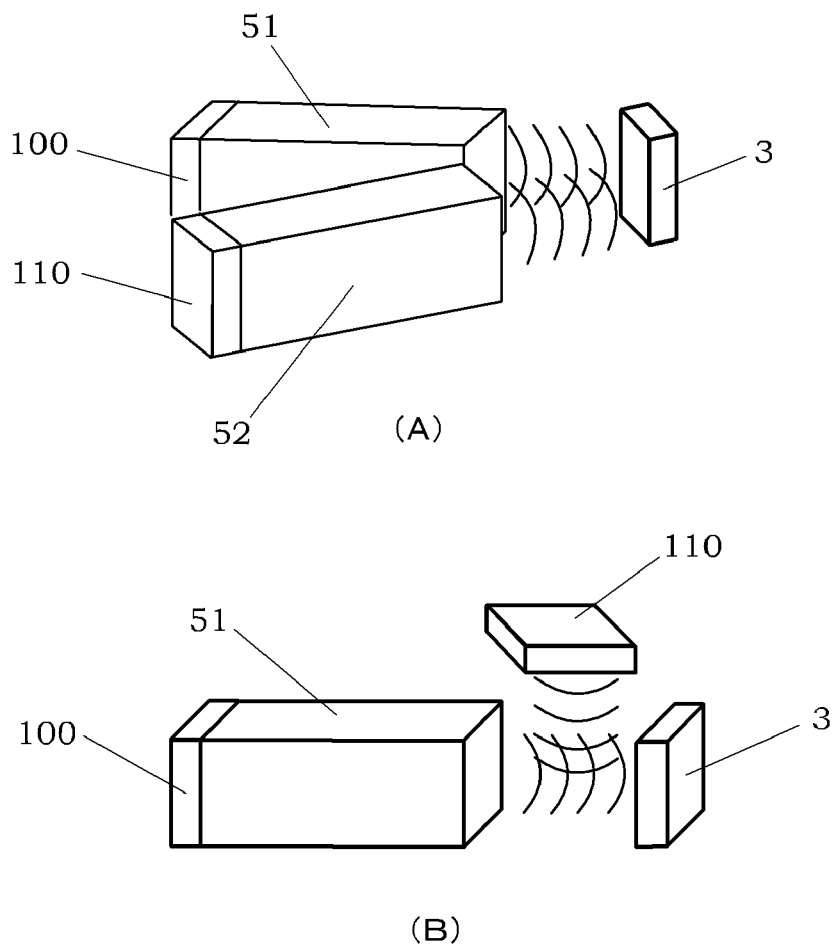
FIGS. 53A and 53B are schematic side views of a fire sensor of a sixteenth embodiment of the present invention.

The fire sensor shown in FIG. 53A uses a tubular body 51 in which one end in the longitudinal direction is open as an ultrasound wave emission end and the other end is connected to the first sound wave generating unit 100 and a tubular body 52 in which one end is open as an ultrasound wave emission end and the other end is connected to the second sound wave generating unit 110. The two tubular bodies (51, 52) are disposed in a V-shaped configuration such that the emission ends of the tubular bodies face the wave receiving element 3, the ultrasound waves emitted from both emission ends mutually intersect before the wave receiving element 3 (between the wave receiving element 3 and emission ends) and mutually interfere due to nonlinearity of the medium (air), and a beat wave is generated.

The two tubular bodies (51, 52) have inherent resonance frequencies similarly to an acoustic tube closed at one end surface in the longitudinal direction. In other words, a frequency $f(=c/\lambda)$ corresponding to the wavelength $\lambda$ satisfying the relationship $L=(\frac{1}{4}+n/2)\times\lambda$ (where n=0, 1, 2, 3, . . . ), where L stands for the size of the tubular bodies (51, 52) in the longitudinal direction, becomes the resonance frequency of the tubular bodies (51, 52). Therefore, where a continuous ultrasound wave satisfying the relationship $L=(\frac{1}{4}+n/2)\times\lambda$ is introduced in the tubular bodies (51, 52), at least part of the ultrasound wave is repeatedly reflected by both end surfaces of the tubular bodies. As a result, the reflected waves and the direct wave are superimposed, causing resonance, and the sound pressure of the ultrasound waves increases inside the tubular bodies. In this case, in order to generate a resonance inside the tubular bodies, the control unit 2 controls the first wave generating unit 100 and second sound wave generating unit 110 so as to transmit a continuous ultrasound wave of m ($>L/\lambda$) periods. In other words, the first sound wave generating unit 100 and second sound wave generating unit 110 are controlled by the control unit 2 so that a time $t_p$ ($=m\times\lambda/c$) in which an ultrasound wave is continuously transmitted from the first sound wave generating unit 100 and second sound wave generating unit 110 becomes longer than a time $t_s$ ($=L/c$) required for the ultrasound wave to propagate between the two ends in the longitudinal direction of the tubular bodies (51, 52) (in other words, $t_p>t_s$). When one end surface is an open end, a knot of sound pressure of the ultrasound wave (that is, a loop of air transfer speed) appears at a very small distance $\Delta L$ from the open end on the outside thereof. Therefore, where the length L used for finding the resonance frequency is corrected by $\Delta L$ (open end correction), a more accurate resonance frequency can be found.

A specific example of the present embodiment will be described below. Where the sound velocity c is 340 m/sec, and the length L in the longitudinal direction of the tubular bodies (51, 52) is 34 mm, the frequency of the first ultrasound wave transmitted from the first sound wave generating unit 100 may be set, for example, to 202.5 kHz (n=40) and the frequency of the second ultrasound wave transmitted from the second sound wave generating unit 110 may be set, for example, to 222.5 kHz (n=44) in order to satisfy the relationship L=(¼+n/2)×λ. In this case, as described hereinabove, the control unit 2 controls the first sound wave generating unit 100 and second sound wave generating unit 110 so that a continuous ultrasound wave of m (>L/λ) periods (for example, an ultrasound wave of about 100 periods) is transmitted. In the monitoring space, a beat wave having a fixed frequency (=20 kHz), which is the difference between the frequency of the first ultrasound wave (202.5 kHz) and the frequency of the second ultrasound wave (=222.5 kHz) is generated. Therefore, the wave receiving element 3 detects the sound pressure of a dilatational wave with a frequency of 20 kHz, and sound pressure can be detected with sufficient sensitivity even with a typical wave receiving element 3. Further, because the first ultrasound wave and second ultrasound wave have respective frequencies of 202.5 kHz and 222.5 kHz, where smoke particles are present in the monitoring space, the decrease in sound pressure occurs that is equivalent to that of the ultrasound wave with a frequency equivalent to 200 kHz and the attenuation amount of the output of the wave receiving element 3 becomes relatively large.

With the present embodiment, because the beat wave is induced outside the tubular bodies (51, 52), viscous resistance of the inner circumferential surface of each tubular body causes no attenuation of the beat wave even when the frequency of the beat wave received by the wave receiving element 3 is low. Thus, when the cross-sectional area (pipe diameter) of the tubular bodies (51, 52) is small, viscous resistance at the inner circumferential surface of the tubular bodies can decrease the sound pressure of the dilatational wave of a frequency equal to or lower than a certain level that passes inside the tubular bodies. However, with the configuration of the present embodiment, because the ultrasound wave passing inside the tubular bodies (51, 52) has a high frequency, the above-described problem can be avoided. Moreover, a resonance is induced and the sound pressure of the ultrasound wave is increased. Therefore, the variation amount of the output of the wave receiving element 3 related to the variation of smoke density increases and the SN ratio rises.

Further, only the tubular body 51 for passing inside thereof the ultrasound wave from the first sound wave generating unit 100 may be provided, as shown in FIG. 53B, and the ultrasound wave emitted from the emission end of the tubular body 51 and the ultrasound wave transmitted from the second sound wave generating unit 110 may be caused to interfere before the wave receiving element 3. In this case, the first sound wave generating unit 100, second sound wave generating unit 110, tubular body 51, and wave receiving element 3 are disposed so that the second sound wave generating unit 110 emits an ultrasound wave toward a space between the emission end of the tubular body 51 and the wave receiving element 3 from the side direction. With such a configuration, because the frequency of the ultrasound wave transmitted from the second sound wave generating unit 110 can be set without limitations imposed by the tubular body 51, the fixed frequency equivalent to the difference in frequency between this ultrasound wave and the ultrasound wave from the first sound wave generating unit 100 can be freely set. In other words, it is possible to match the frequency of the beat wave with the frequency ensuring the highest wave reception sensitivity of the wave receiving element 3.

The above-described effects will be further explained below with reference to the following specific example.

Where the sound velocity c is 340 m/sec, and the length L in the longitudinal direction of the tubular body 51 is 34 mm, the frequency of the first ultrasound wave transmitted from the first sound wave generating unit 100 may be set to 202.5 kHz (n=40) in order to satisfy the relationship L=(¼+n/2)×λ. The frequency of the second ultrasound wave transmitted from the second sound wave generating unit 110 is not required to match the resonance frequency of the tubular body 51 and, therefore, this frequency is preferably set based on the frequency characteristic of sensitivity in the wave receiving element 3. In other words, when the sensitivity of wave receiving element 3 reaches a maximum, for example, with respect to a dilatational wave with a frequency of 12 kHz, it is desirable that the second frequency be set to 214.5 kHz, which is by 12 kHz higher than the first frequency (=202.5 kHz). In this case, a beat wave of a fixed frequency (=12 kHz), which is the difference between the first frequency (=202.5 kHz) and second frequency (=214.5 kHz), is generated in the monitoring space. Therefore, the wave receiving element 3 detects the sound pressure of the dilatational wave with a frequency of 12 kHz and is operated at a frequency ensuring maximum sensitivity. In the configuration shown in FIG. 53B, the relationship between the first sound wave generating unit 100 and second sound wave generating unit 110 may be reversed.

Seventeenth Embodiment

Figure 54:
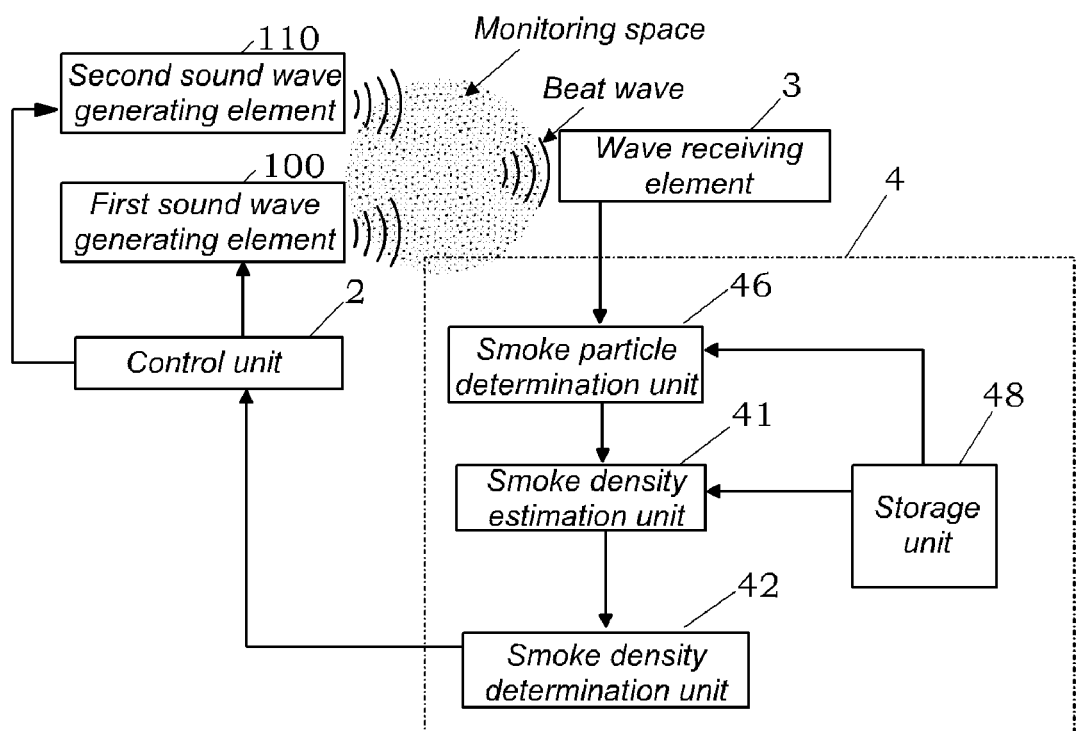
FIG. 54 is a block diagram of a fire sensor of a seventeenth embodiment of the present invention.

The fire sensor of the present embodiment is substantially identical to that of the second embodiment, except that the first sound wave generating unit 100 and second sound wave generating unit 110 are provided as ultrasound wave generating units and the wave receiving element 3 receives a dilatational wave (beat wave) of a frequency (fixed frequency) equivalent to a difference in frequency between the ultrasound waves generated by the first sound wave generating unit 100 and second sound wave generating unit 110, as shown in FIG. 54. Therefore, structural elements identical to those of the second embodiment are assigned with identical reference numerals and redundant explanation thereof is omitted.

An ultrasound wave generating element identical to that of the first embodiment can be used for each of the first sound wave generating unit 100 and second sound wave generating unit 110 employed in the present embodiment, a microphone of an electrostatic capacity type identical to that of the first embodiment can be employed in the wave receiving element 3.

The control unit 2 causes the first sound wave generating unit 100 and second sound wave generating unit 110 to transmit successively a plurality of ultrasound waves of different frequencies by successively changing the frequency of the drive input waveform supplied to the first sound wave generating unit 100 and second sound wave generating unit 110. Further, the control unit 2 changes the frequency of the ultrasound wave from the first sound wave generating unit 100 over a predetermined frequency range (for example, 20 kHz to 82 kHz). In this case, the second sound wave generating unit 110 transmits the ultrasound wave over a frequency range (for example, 32 kHz to 94 kHz) that is by a fixed frequency (for example, 12 kHz) higher than the frequency of the ultrasound wave from the first sound wave generating unit 100. The frequency of the ultrasound wave from the second sound wave generating unit 110 is higher by a fixed frequency than the frequency of the ultrasound wave from the first sound wave generating unit 100 at all times. In other words, a plurality of combinations of the first ultrasound wave from the first sound wave generating unit 100 and the second ultrasound wave from the second sound wave generating unit 110 having a frequency that is higher by a fixed frequency than the frequency of the first ultrasound wave are successively provided to the monitoring space.

The signal processing unit 4 employed in the present embodiment is configured identically to the signal processing unit 4 of the second embodiment. Thus, the signal processing unit 4 has the smoke particle determination unit 46, smoke density estimation unit 41, and smoke density determination unit 42 and is realized by installing an appropriate program on a microcomputer. The processing in the signal processing unit 4 is identical to that of the second embodiment, except that the processing is executed with respect to the output of the wave receiving element 3 that has received the dilatational wave.

With the present embodiment, similarly to the second embodiment, fire determination is performed based on the type of smoke particles present in the monitoring space and smoke density. Therefore, the occurrence rate of false alarm is reduced and a fire sensor with high operation reliability can be provided. Furthermore, because the wave receiving element 3 receives a dilatational wave (beat wave) of a frequency (fixed frequency) equivalent to the difference in frequency between the ultrasound waves from the first and second sound wave generating units, while the decrement ratio of the ultrasound wave caused by smoke particles present in the monitoring space is being increased by increasing the frequency of the ultrasound waves from the first sound wave generating unit 100 and second sound wave generating unit 110, the sound pressure can be detected with sufficient sensitivity even with a typical wave receiving element. The resultant merit is that the SN ratio rises.

In the above-described embodiments, fire sensors are explained in detail as the preferred embodiments of the smoke sensor in accordance with the present invention. In the case of fire sensors, fire is determined based on the decrease amount (attenuation amount) of the output of the ultrasound wave receiving unit that is caused by the increase in the number of smoke particles in the monitoring space, but the application of the smoke sensor in accordance with the present invention is not limited to such a determination. For example, in applications in which it is necessary to ensure the presence of smoke of a certain density in the monitoring space at all times, an abnormality of the monitoring space can be determined when the smoke density becomes lower than a predetermined value. Thus, it is also possible to take a monitoring space in which smoke of a certain density is present at all times as a standard state and detect an abnormality of the monitoring space on the basis of increment of the output of the ultrasound wave receiving unit occurring when the smoke density decreases.

In accordance with the present invention, a smoke density in the monitoring space is estimated based on a difference between a measured output of the wave receiving element that receives an ultrasound wave from a sound wave generating unit via the monitoring space and a standard value and an abnormality of the monitoring space is determined by comparing the estimated smoke density with the predetermined threshold. Therefore, a labyrinth body that is required in the smoke sensor of a light scattering type becomes unnecessary and the diffusion of smoke particles in the monitoring space is facilitated, thereby increasing responsiveness with respect to that of the smoke sensor of a light scattering type. Further, because the effect of background light that creates a problem in the smoke sensor of a light dimming type can be eliminated, the occurrence rate of false alarm can be reduced and reliability of smoke sensor can be increased. Moreover, when the type of smoke particles is determined, because the smoke particles that are the monitoring object can be distinguished from particles that are not the monitoring object, the occurrence rate of false alarm can be further reduced, and when the particles that are not the monitoring object are steam, a fire sensor suitable for use in kitchens and bathrooms can be provided.

Thus, the smoke sensor of sound wave type in accordance with the present invention can resolve the problems inherent to optical smoke sensors and, therefore, can be used in locations where smoke sensors have not been heretofore installed. Accordingly, a wide range of applications, for example as a fire sensor, can be expected.

The invention claimed is:

1. A smoke sensor of sound wave type, comprising:
   a sound wave generating unit that provides a sound wave to a monitoring space;
   a control unit that controls the sound wave generating unit;
   a sound wave receiving unit that receives the sound wave from the sound wave generating unit via the monitoring space; and
   a signal processing unit that detects an abnormality of the monitoring space by using an output of the sound wave receiving unit, wherein
   the signal processing unit comprises a smoke density estimation unit that estimates a smoke density in the monitoring space on the basis of a difference between the output of the sound wave receiving unit and a standard value, and
   a smoke density determination unit that determines the abnormality on the basis of a result obtained by comparing the smoke density found by the smoke density estimation unit with a predetermined threshold, wherein
   the sound wave generating unit has a function of providing a plurality of sound waves that have different frequencies,
   the signal processing unit comprises:
   a storage unit that stores data representing a relationship between the output of the sound wave receiving unit and a frequency of the sound wave provided by the sound wave generating unit that has been examined in advance under a plurality of test conditions that differ in a type of smoke present in the monitoring space and a smoke density; and
   a smoke particle determination unit that determines the type of smoke particles present in the monitoring space by using the data of the storage unit and the output of the sound wave receiving unit obtained by providing each of the plurality of sound waves to an actual monitoring space, and
   the smoke density estimation unit estimates the smoke density in the monitoring space when smoke particles determined by the smoke particle determination unit are identical to particles determined in advance as a monitoring object.

2. The smoke sensor of sound wave type according to claim 1, wherein the sound wave is an ultrasound wave with a frequency equal to or higher than 20 kHz.

3. The smoke sensor of sound wave type according to claim 1, wherein the data stored in the storage unit include a relationship between a frequency of the sound wave provided by the sound wave generating unit and an output variation amount defined as a difference between an output of the sound wave receiving unit in the case the sound wave is received via the monitoring space in a standard state and an output of the sound wave receiving unit in the case the sound wave is received via the actual monitoring space, or a relationship between an output variation ratio obtained by dividing the output variation amount by a predetermined standard value and a frequency of the sound wave provided by the sound wave generating unit.

4. The smoke sensor of sound wave type according to claim 1, wherein the sound wave generating unit comprises a single sound wave generating element having a function of providing a plurality of sound waves having different frequencies, and the control unit controls the sound wave generating element so that the plurality of sound waves are provided successively to the monitoring space.

5. The smoke sensor of sound wave type according to claim 1, wherein the sound wave generating unit periodically provides a sound wave of a predetermined frequency to the monitoring space, and the signal processing unit changes at least one from among a control condition of the sound wave generating unit and a signal processing condition of the output of the sound wave receiving unit on the basis of the output of the sound wave receiving unit obtained by providing the sound wave of the predetermined frequency to the monitoring space.

6. The smoke sensor of sound wave type according to claim 2, wherein the sound wave generating unit is an ultrasound wave generating unit that generates an ultrasound wave when a thermal shock is provided to the air by temperature variations in a heat generating body caused by passing an electric current.

7. The smoke sensor of sound wave type according to claim 6, wherein the ultrasound wave generating unit comprises a base substrate, a heat generating body layer provided on the base substrate, and a thermally insulating layer having a porous structure and provided between the heat generating body layer and the base substrate.

8. The smoke sensor of sound wave type according to claim 6, wherein the control unit controls the ultrasound wave generating unit so that a single-pulse ultrasound wave is provided to the monitoring space.

9. The smoke sensor of sound wave type according to claim 2, wherein when an abnormality is detected by the signal processing unit, the control unit controls the sound wave generating unit so as to generate an alarm sound at a frequency in an audible range that is different from the ultrasound wave provided to the monitoring space.

10. The smoke sensor of sound wave type according to claim 1, wherein
the signal processing unit further comprises:
a sound velocity detection unit that determines a sound velocity based on a time required for a sound wave from the sound wave generating unit to reach the sound wave receiving unit;
a temperature estimation unit that estimates a temperature of the monitoring space on the basis of the sound velocity; and
a temperature determination unit that determines an abnormality of the monitoring space on the basis of a result obtained by comparing the temperature estimated by the temperature estimation unit with a predetermined threshold.

11. The smoke sensor of sound wave type according to claim 10, wherein the signal processing unit further comprises a fire determination unit that determines the presence of fire when the determination of at least one from among the smoke density determination unit and the temperature determination unit indicates an abnormality.

12. The smoke sensor of sound wave type according to claim 10, further comprising a frequency correction unit that corrects the frequency of the sound wave provided by the sound wave generating unit according to the temperature estimated by the temperature estimation unit by using the sound velocity found by the sound velocity detection unit.

13. The smoke sensor of sound wave type according to claim 1, further comprising a tubular body that is disposed between the sound wave generating unit and the sound wave receiving unit and narrows a diffusion range of the sound wave, an inner space of the tubular body being used as a propagation path of the sound wave.

14. The smoke sensor of sound wave type according to claim 13, wherein the sound wave generating unit has a sound wave generating surface disposed so as to oppose a sound wave inlet port of the tubular body, and a surface area of the sound wave generating surface is equal to or larger than an opening surface area of the sound wave inlet port.

15. The smoke sensor of sound wave type according to claim 13, wherein the control unit controls the sound wave generating unit so that an ultrasound wave of a resonance frequency inherent to the tubular body is provided continuously to the monitoring space over a transmission time that is longer than a propagation time required for the ultrasound wave to propagate at least between two ends in the longitudinal direction of the tubular body.

16. The smoke sensor of sound wave type according to claim 15, wherein both end surfaces in the longitudinal direction of the tubular body are closed, the sound wave generating unit is disposed at one end surface, and the sound wave receiving unit is disposed in a location with a maximum pressure variation caused by the sound wave from the sound wave generating unit, on a side surface extending in the longitudinal direction.

17. The smoke sensor of sound wave type according to claim 16, wherein the control unit controls the sound wave generating unit so that a sound wave with a wavelength obtained by dividing a size of the inner space of the tubular body in the longitudinal direction by a natural number is provided to the monitoring space, and the sound wave receiving unit is disposed in a central portion in the longitudinal direction of the tubular body.

18. The smoke sensor of sound wave type according to claim 1, further comprising a reflective member that reflects the sound wave from the sound wave generating unit toward the sound wave receiving unit.

19. The smoke sensor of sound wave type according to claim 18, wherein the control unit controls the sound wave generating unit so that the sound wave of a resonance frequency based on a propagation distance of the sound wave provided by the sound wave generating unit and received by the sound wave receiving unit is provided continuously to the monitoring space over an interval that is longer than a propagation time required for the sound wave to propagate from the sound wave generating unit to the sound wave receiving unit.

20. The smoke sensor of sound wave type according to claim 18, wherein the reflective member comprises a first reflective plate disposed adjacently to the sound wave generating unit, and a second reflective plate disposed adjacently to the sound wave receiving unit so as to oppose the first reflective plate via the monitoring space.

21. The smoke sensor of sound wave type according to claim 20, wherein at least one of the first reflective plate and the second reflective plate has a concave curved surface facing the monitoring space.

22. The smoke sensor of sound wave type according to claim 1, wherein the sound wave generating unit comprises a first sound wave generating unit that provides a sound wave to the monitoring space into which smoke can penetrate from an outer space, and a second sound wave generating unit that provides a sound wave to a reference space into which the smoke cannot penetrate, wherein the sound wave receiving unit comprises a first sound wave receiving unit that receives the sound wave from the first sound wave generating unit, and a second sound wave receiving unit that receives the sound wave from the second sound wave generating unit, and the signal processing unit detects an abnormality of the monitoring space by using the output of the first sound wave receiving unit and the output of the second sound wave receiving unit.

23. The smoke sensor of sound wave type according to claim 22, wherein the smoke density estimation unit further comprises an output correction unit that estimates the smoke density in the monitoring space on the basis of a difference between the output of the first sound wave receiving unit and a standard value and corrects the output of the first sound wave receiving unit based on variations with time of the output of the second sound wave receiving unit.

24. The smoke sensor of sound wave type according to claim 22, further comprising a tubular body disposed between the sound wave generating unit and the sound wave receiving unit and having an inner space thereof used as a propagation path of the sound wave, wherein
the tubular body has a partition wall that partitions the inner space into the monitoring space and the reference space, part of the tubular body that provides the monitoring space has a communication hole of a size allowing smoke to penetrate from an outer space into the monitoring space, the first sound wave generating unit and the second sound wave generating unit are configured of a single sound wave generating element disposed at one end of the tubular body so that sound waves are provided simultaneously to both the monitoring space and the reference space, and the first sound wave receiving unit and the second sound wave receiving unit are disposed at the other end of the tubular body so that the sound waves provided by the single sound wave generating element are received via the monitoring space and the reference space, respectively.

25. The smoke sensor of sound wave type according to claim 22, wherein the reference space has a smoke shielding portion having fine holes of a size so as to prevent the penetration of at least smoke.

26. The smoke sensor of sound wave type according to claim 22, wherein the control unit synchronously controls the first sound wave generating unit and the second sound wave generating unit so that the output of the first sound wave receiving unit and the output of the second sound wave receiving unit have the same frequency and the same phase, and the signal processing unit detects the abnormality by using a differential output equivalent to a difference between the output of the first sound wave receiving unit and the output of the second sound wave receiving unit.

27. The smoke sensor of sound wave type according to claim 26, wherein
the first sound wave generating unit and the second sound wave generating unit have a function of providing a plurality of sound waves having different frequencies,
the signal processing unit comprises:
a storage unit that stores data representing a relationship between the differential output and a frequency of the sound wave provided by the first sound wave generating unit that has been examined in advance under a plurality of test conditions that differ in a type of smoke present in the monitoring space and a smoke density; and
a smoke particle determination unit that determines the type of smoke particles present in the monitoring space by using the data of the storage unit and the output of the first sound wave receiving unit obtained by providing each of the plurality of sound waves to an actual monitoring space, and
the smoke density estimation unit estimates the smoke density in the monitoring space when smoke particles determined by the smoke particle determination unit are identical to particles determined in advance as a monitoring object.

28. The smoke sensor of sound wave type according to claim 27, wherein the data stored in the storage unit include a relationship between a value obtained by dividing the differential output by the output of the second sound wave receiving unit, and the frequency of the sound wave outputted by the first sound wave generating unit.

29. The smoke sensor of sound wave type according to claim 26, wherein a partition is disposed between the monitoring space and the reference space, the monitoring space is defined between the first sound wave generating unit and one surface of the partition, the reference space is defined between the second sound wave generating unit and a surface on the opposite side of the partition, the first sound wave receiving unit and the second sound wave receiving unit are disposed at the partition and configured by a single differential sound wave receiving unit having a first wave receiving unit facing the monitoring space and a second wave receiving unit facing the reference space, and the differential sound wave receiving unit provides, as the differential output, a difference in sound pressure between a sound wave received by the first wave receiving unit and a sound wave received by the second wave receiving unit when the control unit synchronously controls the first sound wave generating unit and the second sound wave generating unit.

30. The smoke sensor of sound wave type according to claim 29, wherein the signal processing unit further comprises an output correction unit that measures, as a reference value, the output of the differential sound wave receiving unit obtained when a sound wave is provided only from the second sound wave generating unit to the reference space and corrects the differential output on the basis of the variation in the reference value with time.

31. The smoke sensor of sound wave type according to claim 1, wherein
the sound wave generating unit comprises:
a first sound wave generating unit that provides a first sound wave with a frequency that is higher than a fixed frequency at which the sound wave receiving unit has sensitivity; and
a second sound wave generating unit that provides a second sound wave with a frequency that is higher than the frequency of the first sound wave by the fixed frequency,
the control unit controls the first sound wave generating unit and the second sound wave generating unit so that the first sound wave and the second sound wave are simultaneously provided to the monitoring space, and
the sound wave receiving unit receives a beat wave produced by mutual interference between the first sound wave and the second sound wave in the monitoring space.

32. The smoke sensor of sound wave type according to claim 31, further comprising:
a first tubular body that is disposed between the first sound wave generating unit and the sound wave receiving unit and narrows a diffusion range of the sound wave, an inner space of the first tubular body being used as a propagation path of the sound wave; and
a second tubular body that is disposed between the second sound wave generating unit and the sound wave receiving unit and narrows a diffusion range of the sound wave, an inner space of the second tubular body being used as a propagation path of the sound wave, wherein the first tubular body and the second tubular body are so disposed with respect to the sound wave receiving unit that the sound wave provided from a sound wave emission port of the first tubular body and the sound wave provided from the sound wave emission port of the second tubular body mutually interfere before the sound wave receiving unit.

33. The smoke sensor of sound wave type according to claim 31, further comprising:

a tubular body that is disposed between the sound wave receiving unit and one of the first sound wave generating unit and the second sound wave generating unit and narrows a diffusion range of the sound wave, an inner space of the tubular body being used as a propagation path of the sound wave, wherein the tubular body is so disposed with respect to the sound wave receiving unit that the sound wave provided from a sound wave emission port of the tubular body and the sound wave provided from the other of the first sound wave generating unit and the second sound wave generating unit mutually interfere before the sound wave receiving unit.

* * * * *